US008642562B2

(12) United States Patent
Moe et al.

(10) Patent No.: US 8,642,562 B2
(45) Date of Patent: *Feb. 4, 2014

(54) POLYSIALIC ACID DERIVATIVES, METHODS OF PRODUCTION, AND USES IN ENHANCING CANCER ANTIGEN PRODUCTION AND TARGETING

(75) Inventors: Gregory R. Moe, Alameda, CA (US); Brent T. Hagen, Oakland, CA (US)

(73) Assignee: Children's Hospital & Research Center Oakland, Oakland, CA (US)

( * ) Notice: Subject to any disclaimer, the term of this patent is extended or adjusted under 35 U.S.C. 154(b) by 73 days.

This patent is subject to a terminal disclaimer.

(21) Appl. No.: 13/323,490

(22) Filed: Dec. 12, 2011

(65) Prior Publication Data

US 2012/0094952 A1  Apr. 19, 2012

Related U.S. Application Data

(63) Continuation of application No. 12/167,909, filed on Jul. 3, 2008, now Pat. No. 8,097,591.

(60) Provisional application No. 60/958,391, filed on Jul. 3, 2007.

(51) Int. Cl.
*A61K 31/715* (2006.01)
*A61K 31/7008* (2006.01)
*A61K 31/70* (2006.01)

(52) U.S. Cl.
USPC ............. 514/23; 514/53; 514/54; 514/61

(58) Field of Classification Search
None
See application file for complete search history.

(56) References Cited

U.S. PATENT DOCUMENTS

| 4,021,542 | A | 5/1977 | Schmidt et al. |
| 4,062,950 | A | 12/1977 | Frommer et al. |
| 4,175,123 | A | 11/1979 | Junge et al. |
| 4,216,208 | A | 8/1980 | DeBarbieri |
| 4,254,256 | A | 3/1981 | Otani et al. |
| 4,314,999 | A | 2/1982 | DeBarbieri |
| 4,656,159 | A | 4/1987 | Mcpherson et al. |
| 4,713,374 | A | 12/1987 | Della Valle et al. |
| 4,797,477 | A | 1/1989 | Yoshimura et al. |
| 4,803,303 | A | 2/1989 | Horii et al. |
| 4,840,941 | A | 6/1989 | Ueno et al. |
| 4,914,195 | A | 4/1990 | Ogura et al. |
| 4,965,198 | A | 10/1990 | Yamasaki et al. |
| 4,968,786 | A | 11/1990 | Ogawa et al. |
| 4,983,725 | A | 1/1991 | Miyaji et al. |
| 5,231,177 | A | 7/1993 | Saito et al. |
| 5,243,035 | A | 9/1993 | Nakabayashi et al. |
| 5,264,424 | A | 11/1993 | Della Valle et al. |
| 5,272,138 | A | 12/1993 | Hakomori et al. |
| 5,332,756 | A | 7/1994 | Mongelli et al. |
| 5,667,285 | A | 9/1997 | Seetharaman et al. |
| 5,674,988 | A | 10/1997 | Sabesan |
| 5,759,823 | A | 6/1998 | Wong et al. |
| 5,962,434 | A | 10/1999 | Schnaar et al. |
| 6,075,134 | A | 6/2000 | Bertozzi et al. |
| 6,110,897 | A | 8/2000 | Unverzagt et al. |
| 6,274,568 | B1 | 8/2001 | Schnaar et al. |
| 6,407,072 | B1 | 6/2002 | Valle et al. |
| 6,458,937 | B1 | 10/2002 | Bertozzi et al. |
| 6,548,476 | B1 | 4/2003 | Wu et al. |
| 6,680,054 | B1 | 1/2004 | Reece et al. |
| 6,697,251 | B1 | 2/2004 | Aisenberg |
| 6,936,701 | B2 | 8/2005 | Bertozzi et al. |
| 7,070,801 | B2 | 7/2006 | Yamazaki et al. |
| 2006/0029621 | A1 | 2/2006 | Granoff et al. |
| 2006/0035284 | A1 | 2/2006 | Granoff et al. |
| 2007/0010482 | A1 | 1/2007 | Moe et al. |
| 2009/0010944 | A1 | 1/2009 | Moe |
| 2009/0010949 | A1 | 1/2009 | Moe |
| 2009/0012043 | A1 | 1/2009 | Moe |
| 2010/0068728 | A1 | 3/2010 | Moe |
| 2010/0260762 | A1 | 10/2010 | Moe et al. |

FOREIGN PATENT DOCUMENTS

| WO | WO0109298 | 2/2001 |
| WO | WO0200974 | 1/2002 |
| WO | WO2006002402 | 1/2006 |
| WO | WO2007075921 | 7/2007 |
| WO | WO2009047792 | 4/2009 |

OTHER PUBLICATIONS

Angata, et al. 'Chemical diversity in the sialic acids and related a-keto acids: an evolution perspective' Chem. Rev., vol. 102, No. 2, pp. 439-469 (2002).
Bardor, et al. 'Mechanism of uptake and incorporation of the non-human sialic acid n-glycolyneuraminic acid into human cells' Biol. Chem.,vol. 280, No. 6, pp. 4228-4237 (2005).
Bertozzi and Kiessling 'Chemical glycobiology' Science Mag., vol. 291, pp. 2357-2364 (2001).
Chamas, et al. 'De-N-acetyl-gangliosides in humans: unusual subcellular distribution of a novel tumor antigen' Cancer Research, vol. 59, pp. 1337-1346 (1999).
Collins, et al. 'Conversion of cellular sialic acid expression from N-acetyl-to-N-glycolylneuraminic acid using a synthetic precursor, N-glycolymannosamine pentaacetate: inhibitition of myelin-associated glycoprotein binding to neural cells' Glycobiology, vol. 10, No. 1., pp. 11-20 (2000).
Dall'Olio 'Protein glycosylation in cancer biology: an overview' Clin. Pathol: Mol. Panthol.,vol. 49, M126-M135 (1996).
Djanashvili, et al. 'Molecular recognition of sialic acid end groups by phenylboronates' Chem. Eur J., vol. 11, pp. 4010-4018 (2005).
Fondy and Emlich 'Haloacetamido analogs of 2-amino-2-deoxy-D-mannose. Syntheses and Effects on Tumor-Bearing Mice' J. Med. Chem., vol. 124, No. 7, pp. 848-852 (1981).
Hakamori 'Tumor malignancy defined by aberrant glycosylation and sphingo(glyco)lipid metabolism' Cancer Res,pp. 56:5309-5318 (1996).

(Continued)

*Primary Examiner* — Karen Canella
(74) *Attorney, Agent, or Firm* — Carol L. Francis; Rudy J. Ng; Bozicevic, Field & Francis LLP

(57) ABSTRACT

The present invention relates to compositions and methods of their production and use, including use in increasing de-N-acetyl sialic acid antigen of a mammalian cell and methods that exploit the increase in deNAc sialic acid antigen on such cells.

19 Claims, 9 Drawing Sheets

(56) References Cited

OTHER PUBLICATIONS

Hanai, et al. 'A novel ganglioside, de-N-acetyl-GM3 (II3NeuNH2LacCer), acting as a strong promoter for epidermal growth factor Receptor Kinase and a Stimulator for cell growth' J. Biol. Chem.,vol. 236, No. 13, pp. 263:6296-6301 (1988).

Hirano, et al. 'Depolymerization and De-n-acetylation of glycosaminoglycuronans by the action of alkali in the presence of sodium borohydride' Conn. Tiss. Research, vol. 3, pp. 73-79 (1975).

Kayser, et al. 'Biosynthesis of a nonphyssiological sialic acid in different rat organs, using N-propanoyl-d-hexosamines as Precursors' J. Biol. Chem., vol. 267, No. 24, pp. 16934-16938 (1992).

Keppler, et al. 'Biochemical engineering of the N-acyl side chain of sialic acid: biological implications' Glycobiology, vol. 11, No. 2, pp. 11R-18R, (2001).

Luchansky, et al. 'Constructing azide-labeled cell surfaces using polysaccharide biosynthetic pathways' Meth. Enzymol., vol. 362, pp. 249-272 (2003).

Manzi, et al. 'Biosynthesis and turnover of O-acetyl and N-acetyl groups in the gangliosides of human melanoma cells' J. Biol. Chem., vol. 265, No. 22, pp. 13091-13103, (1990).

Moe, et al. 'Epitopes recognized by a nonautoreactive murine anti-N-Propionyl Meningococcal group B polysaccharide monoclonal antibody' Infect. Immun., vol. 73, No. 4, pp. 2123-2128 (2005).

Oetke, et al. 'Evidence for efficient uptake and incorporation of sialic acid by eukaryotic cells' Eur. J. Biochem, vol. 268, pp. 268:4553-4561 (2001).

Popa, et al. 'Purification and structural characterization of de-N-acetylated form of GDE ganglioside present in human melanoma tumors' Glycobiology, vol. 17, No. 4, pp. 367-373 (2007).

Shimamura,et al. 'Reductive cleavage of Xaa-proline peptide bonds by mild alkaline borohydride treatment employed to release o-glycosidically linked carbohydrate units of glycoproteins' Archives of Biochem, vol. 232, No. 2, pp. 699-706 (1984).

Sjoberg, et al. 'Expression of De-N-acetyl-gangliosides in human melanoma cells is induced by genistein or nocodazole' J. Biol. Chem, vol. 270 No. 7, pp. 2921-2930(1995).

Varki and Angata 'Siglecs—the major subfamily of I-type lectins' Glycobiology, vol. 16, No. 1 , pp. 1R-27R (2006).

Zinkernagle 'On Immunity Against Infections and Vaccines' Scand J Immunol, vol. 60, pp. 9-13 (2004).

Zou, et al. 'Biochengineering of surface GD3 ganglioside for immunotargeting human melonoma cells' J. Biol. Chem., vol. 279. No. 24, pp. 25390-25399 (2004).

POLYSIALIC ACID DERIVATIVES, METHODS OF PRODUCTION, AND USES IN ENHANCING CANCER ANTIGEN PRODUCTION AND TARGETING

CROSS-REFERENCE TO RELATED APPLICATION

This application claims priority benefit of U.S. provisional application Ser. No. 60/958,391, filed Jul. 3, 2007, and to U.S. patent application Ser. No. 12/167,909, filed on Jul. 3, 2008, which applications are incorporated herein by reference in their entirety.

STATEMENT REGARDING FEDERALLY SPONSORED RESEARCH

This invention was made with government support under grants no. AI64314 awarded by the National Institute of Allergy and Infectious Diseases, and the National Institute of Health. The government has certain rights in this invention.

TECHNICAL FIELD

This disclosure relates to polysialic acid derivatives, compositions, methods of their production and uses.

BACKGROUND

One goal of cancer immunotherapy is to identify antigens that are either uniquely expressed on tumor cells and/or are overexpressed (Carter et al Endocrine-Related Cancer, 2004, 11:659). The antigens exhibiting these properties can then be used as targets of antibodies elicited by vaccination or monoclonal antibodies and antibody conjugates administered therapeutically. Antibodies that are reactive with antigens that are uniquely expressed or are relatively overexpressed in cancer cells can limit growth and/or metastasis of the cells. The mechanisms include antibody dependent cellular cytotoxicity (ADCC), antibody dependent cytotoxicity (ADC), or complement-dependent cytotoxicity (CDC) (Carter et al Endocrine-Related Cancer, 2004, 11:659). Further, antibodies that are reactive with cell surface antigens can be internalized after binding to the cell surface antigen by endocytosis. Thus, attachment of cytotoxic drugs or toxins to the antibody can provide a means to specifically target the reagents to cancer cells.

Many human tumors have been shown to uniquely express or overexpress a derivative of poly alpha (2→8) N-acetyl neuraminic acid that contains de-N-acetyl residues using a murine monoclonal antibody, SEAM 3 (Moe et al, Infect. Immun., 2005, 73:2123). SEAM 3 binds to poly alpha (2→8) N-acetyl neuraminic acid that contains a mixture of N-acetyl and de-N-acetyl residues. SEAM 3 can be used to detect expression of this antigen both intracellularly and on the cell surface and has functional activity against tumor cells that express the antigen.

Sialic acids are N- and/or O-substituted derivatives of the nine carbon acidic sugar, neuraminic acid (Varki, A. Glycobiology, 1992, 2:25). In humans, the sugars are located on the terminal ends of a wide variety of cell surface glycoproteins and glycolipids and have an important role in many biological processes. In cancer, cells that can metastasize often have larger amounts of sialic acid-modified glycoproteins, which may help them enter the blood stream. Also, it has long been recognized that the sialic acid of tumor cells is modified in ways that differ from normal cells (Hakamori Cancer Res. 1996, 56:5309, Dall'Olio Clin. Mol. Pathol. 1996, 49:M126, Kim and Varki Glycoconj. J. 1997, 14:569). For instance, altered expression patterns of sialic acid and its derivatives have been used as markers for abnormal cellular processes such as cancer. (O'Kennedy et al., Cancer Lett., 1991 58:91; Vedralova et al. Cancer Lett. 1994 78:171; and Horgan et al., Clin. Chim. Acta., 1982 118:327; and Narayanan, S. Ann. Clin. Lab. Sci. 1994 24:376).

One sialic acid derivative thought to be uncommon in normal cells, but present on cancer cells is de-N-acetyl sialic acid (Hanai et al J. Biol. Chem. 1988, 263:6296, Manzi et al J. Biol. Chem. 1990, 265:1309, Sjoberg et al J. Biol. Chem. 1995, 270:2921, Chamas et al 1999, Cancer Res. 59:1337; and Popa et al Glycobiology. 2007 17:367).

Sialic acid derivatives that are recognized by specific antibodies and the level of expression of the derivative can be manipulated both in vitro and in vivo. Most often, the expression of a particular sialic acid derivative in human cells has been manipulated by providing derivatives of mannosamine (Bertozzi et al., "Chemical Glycobiology" Science (2001) 291:2357-2364). For example, it has been shown that providing exogenous N-propionyl mannosamine results in the production of N-propionyl polysialic acid (N—Pr PSA) derivatives that can be detected by anti-N—Pr PSA monoclonal antibodies and polyclonal antibodies elicited by immunization with an N—Pr PSA-tetanus toxoid conjugate vaccine (Zou et al J. Biol. Chem., 2004, 279:25390).

It has also been shown that eukaryotic cells can compensate for a block of internal sialic acid biosynthesis by acquiring another precursor of sialic acid biosynthesis, N-acetyl neuraminic acid, from extracellular sources (Oetke et al, Eur. J. Biochem., 2001, 268:4553). Cells also can acquire sialic acid derivatives, such as N-glycoyl sialic acid, from N-glycoyl sialic acid-containing glycoconjugates by pinocytosis (Bardor et al, J. Biol. Chem., 2006, 280:4228). It has been suggested that the sialic acid present on internalized glycoconjugates is hydrolyzed to N-acyl neuraminic acid when endocytotic vesicles fuse with lysozomes. The free N-acyl neuraminic acid is then transported first to the cytoplasm then to the nucleus by specific transport proteins where it is finally converted to the sialic acid transferase substrate, CMP-N-acyl neuraminic acid (Bardor et al, J. Biol. Chem., 2006, 280: 4228).

Literature

Amino sugars, derivatives and related literature of interest are reported in the following U.S. Pat. Nos. 4,021,542; 4,062,950; 4,175,123; 4,216,208; 4,254,256; 4,314,999; 4,656,159; 4,713,374; 4,797,477; 4,803,303; 4,840,941; 4,914,195; 4,968,786; 4,983,725; 5,231,177; 5,243,035; 5,264,424; 5,272,138; 5,332,756; 5,667,285; 5,674,988; 5,759,823; 5,962,434; 6,075,134; 6,110,897; 6,274,568; 6,407,072; 6,458,937; 6,548,476; 6,697,251; 6,680,054; 6,936,701; and 7,070,801, and in the following references: Angata and Varki Chem. Rev. 2002, 102:439; Hakamori Cancer Res. 1996, 56:5309; Dall'Olio Clin. Mol. Pathol. 1996, 49:M126; Kim and Varki Glycoconj. J. 1997, 14:569; Hanai et al J. Biol. Chem. 1988, 263:6296; Manzi et al J. Biol. Chem. 1990, 265:1309; Sjoberg et al J. Biol. Chem. 1995, 270:2921; Chamas et al Cancer Res. 1999, 59:1337; Popa et al Glycobiology. 2007 17:367; Kayser et al J. Biol. Chem. 1992 267:16934; Keppler et al Glycobiology 2001, 11:11R; Luchansky et al Meth. Enzymol. 2003, 362:249; Oetke et al Eur. J. Biochem. 2001, 268:4553; Collins et al Glycobiology 2000, 10:11; and Bardor et al J. Biol. Chem. 2005, 280:4228.

The antibody SEAM 3 is reported in Moe et al, Infect. Immun., 2005, 73:2123. Sodium borohydride reactions and related are reported in various references, such as Hirano et al, Connect Tissue Res, 1975, 3:73; Shimamura et al, Arch Biochem Biophys, 1984, 232:699; and Djanashvili et al, Chem Eur J, 2005, 11:4010.

Various references report on sialic acid precursors, derivatives, antigens and uses (Zou et al J. Biol. Chem., 2004, 279:25390; Oetke et al Eur. J. Biochem., 2001, 268:4553; Bardor et al, J. Biol. Chem., 2006, 280:4228; Bertozzi et al., "Chemical Glycobiology" Science (2001) 291:2357-2364). See also US 2007/0010482; U.S. application Ser. No. 11/645,255, filed Dec. 22, 2006; WO 2006/002402; and PCT application serial no. PCT/US2006/04885, filed Dec. 22, 2006.

SUMMARY

The present invention generally relates to compositions and methods of their production and use, including use in increasing de-N-acetyl sialic acid antigen of a mammalian cell and methods that exploit the increase in deNAc sialic acid antigen on such cells.

In one embodiment, the methods involve increasing antigen on the surface of a mammalian cell, particularly a cancer cell, by contacting the cell with an effective amount of a composition described herein, which method can be exploited to facilitate binding of an antibody to a cell, as well as to directly reduce the viability of a cell, particularly when applied at a higher concentrations than is necessary to elicit antibodies to the antigen.

Also provided are methods of eliciting antibodies to a cell in a subject having a deNAc sialic acid antigen by using an immunogenic composition disclosed herein.

The compositions disclosed herein include an isolated polysialic acid derivative that comprises a mixture of N-acetyl and de-N-acetyl residues and that is resistant to degradation by exoneuraminidase. These compositions also include polysialic acid derivatives having a non-reducing end that is enriched with de-N-acetyl residues, as well as compositions that are enriched with such derivatives. The compositions further include a substantially unoxidized isolated polysialic acid derivative having mixture of N-acetyl sialic acid and de-N-acetyl sialic residues, and a non-reducing end de-N-acetyl residue resistant to degradation by exoneuraminidase, where the composition is substantially free of polysialic acid having a non-reducing end N-acetyl sialic acid residue. The compositions also include an aggregate of an isolated polysialic acid derivative disclosed herein, including compositions enriched with an aggregate of polysialic acid derivatives having variable chain lengths, as well as compositions of an aggregate of a polysialic acid derivative having a defined degree of polymerization.

Methods for producing the compositions can involve: (i) treating a first composition with exoneuraminidase, where the first composition comprises a polysialic acid derivative having a mixture of N-acetyl and de-N-acetyl residues; and (ii) isolating from the first composition polysialic acid derivatives resistant to degradation by the exoneuraminidase. Another method of production involves: (i) providing a first composition comprising de-N-acetylated polysialic acid having a mixture of N-acetyl and de-N-acetyl residues; (ii) re-acetylating the de-N-acetylated polysialic acid to generate a second composition comprising partially re-acetylated polysialic acid; and (iii) isolating from the second composition polysialic acid derivative that is resistant to degradation by exoneuraminidase. Another method of production involves forming an aggregate of an isolated polysialic acid derivative by exposing the derivative to aggregating conditions to form an aggregate, and isolating the aggregate. An additional method for producing the compositions involves (i) providing a solution comprising a mixture of polysialic acid derivatives each having: a different degree of polymerization, a different mixture of N-acetyl residues and de-N-acetyl residues, and a non-reducing end N-acetyl sialic acid residue; (ii) subjecting the solution to ion exchange chromatography to generate fractions; and (iii) isolating from one or more of the fractions a polysialic acid derivative having a defined degree of polymerization and a non-reducing end de-N-acetyl residue resistant to degradation by exoneuraminidase.

The compositions and methods disclosed herein take advantage of the finding that the polysialic acid derivatives disclosed herein are capable of being exogenously applied to cells, and then taken up and presented on a cell surface as a substantially intact antigen that is observed on tumor cells but not on normal cells. This property extends from the finding that the compositions of the present disclosure are unexpectedly stable to degradation when applied exogenously to a cell or administered to a subject.

The compositions and methods disclosed herein can also take advantage of the finding that the amount of intact antigen on the cell surface is greatly increased relative to prior polysialic acid compositions that are susceptible to degradation by exoneuraminidase and/or deficient in a non-reducing end enriched for de-N-acetyl residues. The compositions and methods disclosed herein can also take advantage of the finding that the increased amount of antigen presented by the cells provides not only a novel target for antibodies to bind with great specificity and selectively, but can increase the immune response in a subject directed against cells that express the antigen relative to prior polysialic acid compositions that are susceptible to degradation by exoneuraminidase and/or deficient in a non-reducing end enriched for de-N-acetyl residues. The compositions and methods disclosed herein can also take advantage of the finding that aggregates of the polysialic acid derivatives are more readily taken up by cells and expressed on the cell surface compared to the corresponding non-aggregated derivative. The compositions and methods disclosed herein can also take advantage of the finding that substantially unoxidized and purified polysialic acid derivatives can be produced and characterized, and that smaller derivatives exhibit as much activity as longer derivatives, indicating the smallest derivatives contain the minimal features necessary for effective activity.

As such, the methods and compositions of the present disclosure find use in many applications, including in the treatment and/or prevention of bacterial infections and cancer.

Accordingly, in one aspect the present disclosure provides methods of increasing a de-N-acetylated antigen of a cancer cell comprising contacting a cancer cell having a de-N-acetyl sialic acid antigen with an effective amount of a composition comprising a polysialic acid derivative to increase the amount of the de-N-acetyl sialic acid antigen of said cell, wherein said polysialic acid derivative is substantially unoxidized and purified and comprises (i) a mixture of N-acetyl sialic acid and de-N-acetyl sialic acid residues, and (ii) a non-reducing end de-N-acetyl sialic acid residue that is resistant to degradation by exoneuraminidase.

In related embodiments, the cancer cell presents a de-N-acetyl sialic acid epitope and, in some embodiments, is a neuroblastoma cell, a leukemia cell, or a melanoma cell. In further related embodiments, the antigen comprises a de-N-acetyl sialic acid epitope. In related embodiments the cell is in a subject, and said contacting comprises administering to said subject an effective amount of said composition. In related embodiments administering is by infusion or by local injection. Administering can be prior to surgical intervention to remove cancerous cells, at the time of or after surgical intervention to remove cancerous cells, and/or with at least one of an immunotherapy, a cancer chemotherapy or a radiation therapy to the subject.

In another aspect, the present disclosure provides methods of facilitating binding of an antibody to a cell having a de-N-acetyl sialic acid antigen comprising contacting a cell having a de-N-acetyl sialic acid antigen with an effective amount of a composition comprising a polysialic acid derivative so as to increase the amount of said antigen on said cell, wherein said polysialic acid derivative is substantially unoxidized and purified and comprises (i) a mixture of N-acetyl sialic acid and de-N-acetyl sialic acid residues, and (ii) a non-reducing end de-N-acetyl sialic acid residue that is resistant to degradation by exoneuraminidase; and contacting said cell with an antibody specific for said antigen to facilitate binding of said antibody to said cell. In related embodiments, binding of the antibody to the cell facilitates uptake of said antibody by said cell. In related embodiments, the antigen comprises a de-N-acetylated sialic acid epitope. In some embodiments, binding of the antibody to said cell is cytotoxic to the cell. The antibody can be specific for a de-N-acetylated sialic acid epitope of said antigen, and in specific embodiments is the SEAM 3 monoclonal antibody.

In related embodiments, the cell is a cancer cell. In related embodiments, the antigen is extracellularly accessible cell during cell division. In further embodiments, the antibody can be provided as conjugate, e.g., where the conjugate comprises a detectable label or a cytotoxic drug (e.g., a toxin In another aspect the present disclosure provides methods of eliciting antibody to a cell having a de-N-acetyl sialic acid antigen in a subject, comprising administering to a subject an effective amount of an immunogenic composition comprising an antigen so as to increase expression of said antigen by said cell, wherein said antigen comprises a substantially unoxidized and purified polysialic acid derivative having (i) a mixture of N-acetyl sialic acid and de-N-acetyl sialic acid residues, and (ii) a non-reducing end de-N-acetyl sialic acid residue which is resistant to degradation by exoneuraminidase, and wherein said administering is effective to elicit production of an antibody in said subject that specifically binds said cell. In related embodiments, binding of the antibody to the cell is cytotoxic. In further related embodiments, the antibody is specific for a de-N-acetylated sialic acid epitope. In related embodiments, the cell is a cancer cell. In related embodiments, antigen is extracellularly accessible during cell division.

In another aspect, the present disclosure provides methods of reducing the viability of a cancer cell comprising contacting a cancer cell with an effective amount of a composition comprising a polysialic acid derivative so as to reduce the viability of said cell, wherein said polysialic acid derivative has a reducing end and a non-reducing end, and wherein said polysialic acid derivative is a substantially unoxidized and purified oligosaccharide comprising (i) a mixture of N-acetyl sialic acid and de-N-acetyl sialic acid residues, and (ii) a de-N-acetyl sialic acid residue at said non-reducing end that is resistant to degradation by exoneuraminidase. In related embodiments, intracellular uptake of the polysialic acid derivative is cytotoxic to the cancer cell. In related embodiments, the cancer cell is a neuroblastoma cell, a leukemia cell, or a melanoma cell.

In related embodiments, the polysialic derivative comprises at least one dimer of de-N-acetyl sialic acid and N-acetyl sialic acid linked through a glycosidic bond selected from $\alpha(2\rightarrow 8)$ and $\alpha(2\rightarrow 9)$, where the polysialic derivative can have a degree of polymerization of from about 2-10, from about 2-5, of about 2-4, and/or about 2. In further related embodiments, the mixture comprises de-N-acetyl sialic residues in an amount of about 10%-60%. In related embodiments, the polysialic derivative has about 1 de-N-acetyl sialic residue per polysialic acid derivative chain. The polysialic acid derivative can comprise a conjugate in related embodiments. In further related embodiments, the non-reducing end de-N-acetyl sialic acid is linked through a glycosidic bond to an adjacent N-acetyl sialic acid so as to form a de-N-acetyl sialic acid antigen at the non-reducing end of said polysialic acid derivative. In related embodiments, the de-N-acetyl sialic acid is neuraminic acid, and the N-acetyl sialic acid is N-acetyl neuraminic acid. In related embodiments, at least one of the neuraminic acid and said N-acetyl neuraminic acid comprises at least one O-acetylated group. In further related embodiments, the polysialic acid is obtainable from a capsular polysaccharide homopolymer of a bacterium selected from the group consisting of *Escherichia coli* K1, *Neisseria meningitidis* Serogroup B, and *Neisseria meningitidis* Serogroup C. In related embodiments, the cell is in a subject, and said contacting comprises administering to said subject an effective amount of said composition.

In another aspect, the present disclosure provides methods of producing an isolated polysialic acid derivative having a defined degree of polymerization and a non-reducing end de-N-acetyl residue resistant to degradation by exoneuraminidase comprising providing a solution comprising a mixture of polysialic acid derivatives each having (i) a different degree of polymerization, (ii) a different mixture of N-acetyl residues and de-N-acetyl residues, and (iii) a non-reducing end N-acetyl sialic acid residue; subjecting said solution to ion exchange chromatography to generate fractions; and isolating from one or more of said fractions a polysialic acid derivative having a defined degree of polymerization and a non-reducing end de-N-acetyl residue resistant to degradation by exoneuraminidase, whereby said isolated polysialic acid derivative is produced. In related embodiments, the ion exchange chromatography is anion exchange chromatography. In related embodiments, the isolated polysialic acid derivative has a degree of polymerization of about 2 to 10, of about 2 to 5, about 2-4, and/or about 2. In related embodiments, the isolated polysialic acid derivative is substantially unoxidized.

In related embodiments, the non-reducing end de-N-acetyl sialic acid residue of said isolated polysialic acid derivative is linked through a glycosidic bond to an N-acetyl sialic acid residue. In related embodiments, the glycosidic bond is selected from the group consisting of $\alpha(2\rightarrow 8)$ and $\alpha(2\rightarrow 9)$. In further related embodiments, the mixture comprises de-N-acetyl sialic residues in an amount of about 10%-60%. In related embodiments, the isolated polysialic derivative has about 1 de-N-acetyl sialic residue per polysialic acid derivative chain. In other related embodiments, the isolated polysialic acid derivative comprises a conjugate.

In other related embodiments, the de-N-acetyl sialic acid is neuraminic acid, and said N-acetyl sialic acid is N-acetyl neuraminic acid. In related embodiments, at least one of the neuraminic acid and the N-acetyl neuraminic acid comprises at least one O-acetylated group. In related embodiments, the polysialic acid derivative is derivable from a capsular polysaccharide homopolymer of a bacterium selected from the group consisting of *Escherichia coli* K1, *Neisseria meningitidis* Serogroup B, and *Neisseria meningitidis* Serogroup C. In related embodiments, the mixture of polysialic acid derivatives is produced by treating a first composition comprising a polysialic acid derivative having a mixture of N-acetyl and de-N-acetyl residues with exoneuraminidase. In further related embodiments, the mixture of polysialic acid derivatives is produced by re-acetylating a first composition comprising de-N-acetylated polysialic acid to generate a second composition comprising partially re-acetylated polysialic acid having a mixture of N-acetyl and de-N-acetyl residues and which is resistant to degradation by exoneuraminidase.

In another aspect, the present disclosure provides isolated polysialic acid derivatives produced according to the methods disclosed herein, as well as pharmaceutical compositions comprising such isolated polysialic acid derivatives.

In another aspect, the present disclosure provides compositions comprising an isolated polysialic acid derivative, said isolated polysialic acid derivative being substantially unoxidized and comprising (i) mixture of N-acetyl sialic acid and de-N-acetyl sialic residues, and (ii) a non-reducing end de-N-acetyl residue that is resistant to degradation by exoneuraminidase, wherein said composition is substantially free of polysialic acid having a non-reducing end N-acetyl sialic acid residue. In related embodiments, the isolated polysialic derivative comprises at least one dimer of de-N-acetyl sialic acid and N-acetyl sialic acid linked through a glycosidic bond selected from α(2→8) and α(2→9). In related embodiments, the isolated polysialic derivative has a degree of polymerization of about 2-10, of about 2-5, about 2-4, and/or about 2. In related embodiments, the non-reducing end de-N-acetyl sialic acid residue is linked through a glycosidic bond to an N-acetyl sialic acid residue. In related embodiments, the mixture comprises de-N-acetyl sialic residues in an amount of about 10%-60%. In further related embodiments, the isolated polysialic derivative has about 1 de-N-acetyl sialic residue per polysialic acid derivative chain. In other embodiments, the isolated polysialic acid derivative comprises a conjugate. In certain embodiments, the de-N-acetyl sialic acid is neuraminic acid, and said N-acetyl sialic acid is N-acetyl neuraminic acid, and can be such that at least one of said neuraminic acid and said N-acetyl neuraminic acid comprises at least one O-acetylated group. In related embodiments, the isolated polysialic acid derivative is derivable from a capsular polysaccharide homopolymer of a bacterium selected from the group consisting of *Escherichia coli* K1, *Neisseria meningitidis* Serogroup B, and *Neisseria meningitidis* Serogroup C. In certain embodiments, the composition comprises an aggregate of the polysialic acid derivative, where the aggregate can comprise a microscopic particle.

In another aspect, the present disclosure provides methods of producing an aggregate comprising a polysialic acid derivative comprising placing a substantially unoxidized and purified polysialic acid derivative under aggregating conditions so as to form an aggregate, said polysialic acid derivative comprising (i) a mixture of N-acetyl and de-N-acetyl residues, said de-N-acetyl residues comprising about 10%-80% of said mixture, and (ii) a non-reducing end resistant to degradation by exoneuraminidase. In related embodiments, the aggregating condition is heating (e.g., heating is from about 30° C. to 70° C.) or the addition of an aggregating excipient (e.g., aluminum hydroxide). In related embodiments, the aggregate is a particle, e.g., a microscopic particle.

DESCRIPTION OF EXEMPLARY EMBODIMENTS

Figure 1:
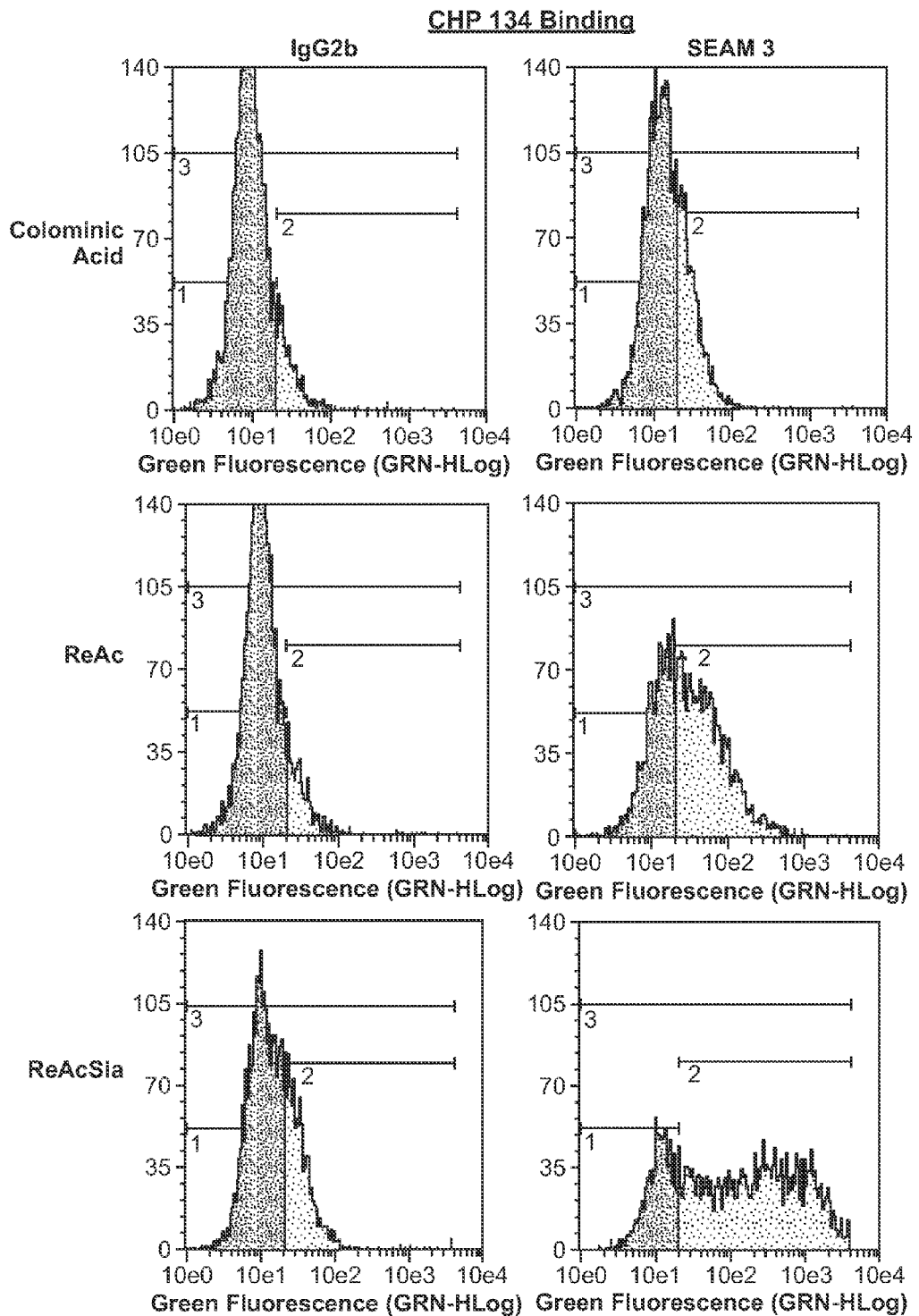
FIG. 1 shows flow cytometry results for an irrelevant, isotype-matched control mAb IgG2b and SEAM 3 binding to CHP-134 neuroblastoma cells exogenously exposed to a polysialic acid (colominic acid), a re-N-acetylated polysialic acid derivative (re-N-acetylated colominic acid (ReAc)), and a polysialic acid derivative that is resistant to exoneuraminidase (re-N-acetylated colominic acid that has been selected for resistance to exoneuraminidase (ReAcSia)).
Figure 2:
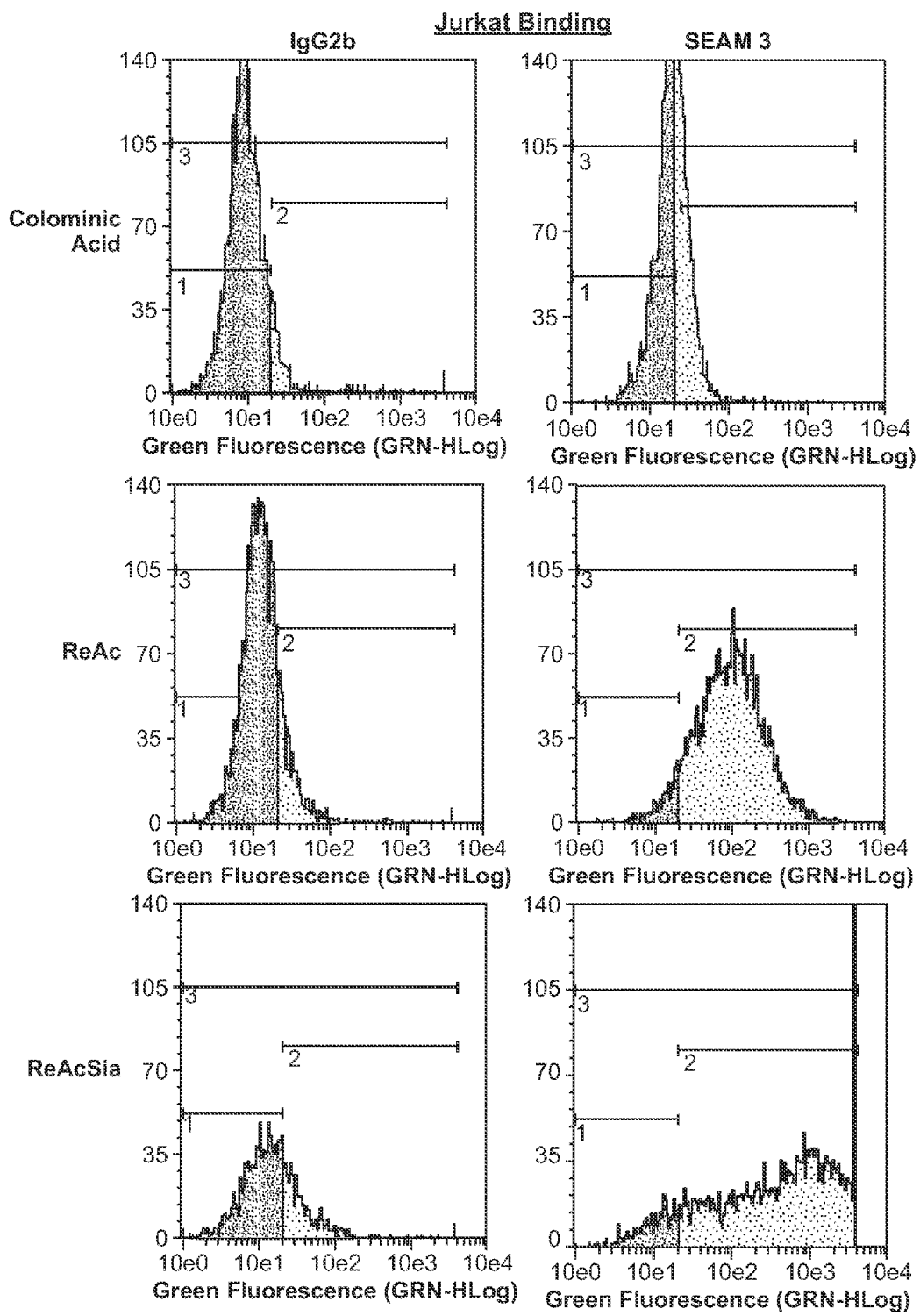
FIG. 2 shows flow cytometry results for an irrelevant, isotype-matched control mAb IgG2b and SEAM 3 binding to Jurkat leukemia cells exogenously exposed to a polysialic acid (colominic acid), a re-N-acetylated polysialic acid derivative (re-N-acetylated colominic acid (ReAc)), and a polysialic acid derivative that is resistant to exoneuraminidase (re-N-acetylated colominic acid that has been selected for resistance to exoneuraminidase (ReAcSia)).
Figure 3:
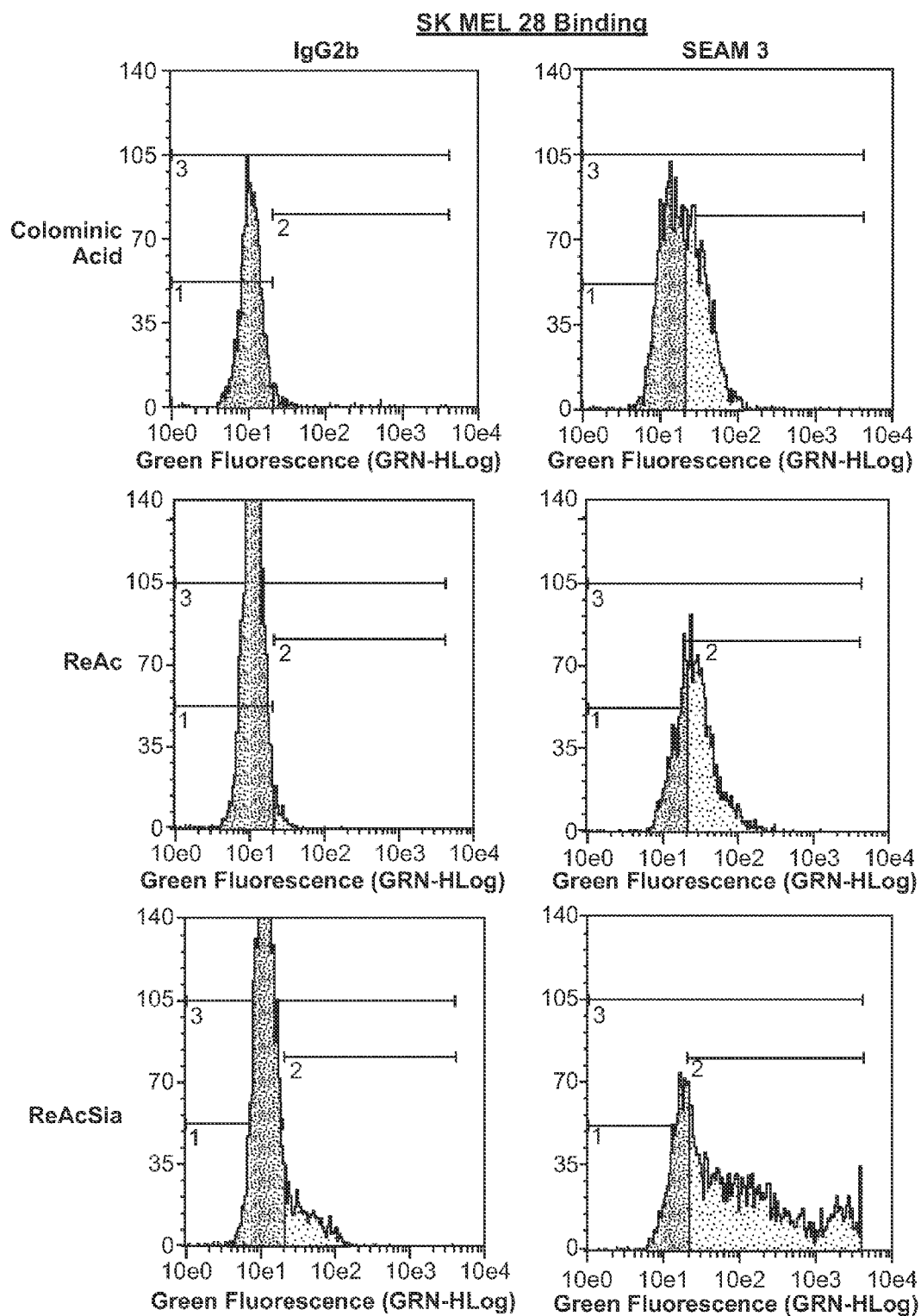
FIG. 3 shows flow cytometry results for an irrelevant, isotype-matched control mAb IgG2b and SEAM 3 binding to SK-MEL 28 melanoma cells exogenously exposed to a polysialic acid (colominic acid), re-N-acetylated polysialic acid derivative (re-N-acetylated colominic acid (ReAc)), and a polysialic acid derivative that is resistant to exoneuraminidase (re-N-acetylated colominic acid that has been selected for resistance to exoneuraminidase (ReAcSia)).

The present disclosure is based on the discovery that a de-N-acetylated sialic acid cancer cell antigen can be greatly increased in cancer cells by externally providing a synthetic neuraminic acid-containing polysialic acid (PSA) that is resistant to degradation by exoneuraminidase and that has been enriched for neuraminic acid residues. The antigen, a poly alpha (2→8) or alpha (2→9) N-acetyl neuraminic acid (PSA), contains a mixture of N-acetyl and de-N-acetyl residues (that is, neuraminic acid-containing PSA). Rather than being hydrolyzed to monomers by the cells, it appears that the neuraminic acid-containing PSA derivatives are taken up by cells and transferred as an intact polymeric molecule to produce a surface expressed glycoconjugate. There is no known mechanism for this to occur in human cells. The antigen also accumulates in the nucleoli of cells to a significant degree. Regardless of mechanism, the PSA derivatives are taken up by the cells and processed in a manner so as to render the cell less viable and present a de-N-acetyl sialic acid antigen on the cell surface. The disclosure also is based on the discovery that aggregates of the neuraminic acid-containing PSA derivatives are more readily taken up by cells and expressed on the cell surface as compared to the corresponding non-aggregated derivative. Further, the disclosure is based on the discovery that internalization by cells of an antibody, SEAM 3, that recognizes the neuraminic acid-containing PSA epitope is greatly increased by the increased surface expressed neuraminic acid-containing PSA antigen resulting from externally providing the synthesized antigen. The disclosure is also based on the discovery that shorter chain length PSA derivatives which are substantially unoxidized and purified, and which possess a non-reducing end de-N-acetyl residue, are significantly more active than corresponding PSA derivatives lacking such features. The disclosure is further based on such PSA derivatives and methods of their production.

Thus, the discovery provides compositions and methods for increasing the expression of a sialic acid antigen that is observed on cancer cells but not on normal cells. This can be useful to render these cells more immunogenic, reduce viability of the cells in general, and/or to facilitate binding of antibodies specific for a de-N-acetyl sialic acid antigen.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antigen" includes a plurality of such antigens and reference to "the peptide" includes reference to one or more peptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

When describing the compositions, pharmaceutical formulations containing such, and methods of producing and using such compositions, the following terms have the following meanings unless otherwise indicated. It should also be understood that any of the moieties defined forth below may be substituted with a variety of substituents, and that the respective definitions are intended to include such substituted moieties within their scope.

The term "amino sugar" refers to a sugar or saccharide that contains an amino group in place of a hydroxyl group. Derivatives of amino containing sugars, such as N-acetyl-glucosamine, N-acetyl mannosamine, N-acetyl galactosamine, N-acetyl neuraminic acid and sialic acids in general are examples of amino sugars.

The term "analog" or "analogue" refers to without limitation any compound which has structural similarity to the compounds of the present disclosure and would be expected, by one skilled in the art, to exhibit the same or similar utility as the claimed and/or referenced compounds.

The term "carrier" as used in the context of a carrier conjugated to a polysialic acid derivative generally refers to a peptide or protein carrier, such as an antibody or antibody fragment. "Carrier" encompasses peptides or proteins that enhance immunogenicity of a compound.

The term "cell surface antigen" (or "cell surface epitope") refers to an antigen (or epitope) on surface of a cell that is extracellularly accessible at any cell cycle stage of the cell, including antigens that are predominantly or only extracellularly accessible during cell division. "Extracellularly accessible" in this context refers to an antigen that can be bound by an antibody provided outside the cell without need for permeabilization of the cell membrane.

The term "chemotherapy" as used herein refers to use of an agent (e.g., drug, antibody, etc.), particularly an agent(s) that is selectively destructive to a cancerous cell, in treatment of a disease, with treatment of cancer being of particular interest.

The term "conjugated" generally refers to a chemical linkage, either covalent or non-covalent, usually covalent, that proximally associates one molecule of interest with second molecule of interest.

The term "de-N-acetyl sialic acid antigen" (which may also be referred to as "de-N-acetylated sialic acid antigen" or "deNAc SA antigen") refers to a compound having or mimicking a deNAc sialic acid epitope (deNAc SA epitope), which epitope is minimally defined by a dimer of residues of sialic acid or sialic acid derivative, where the dimer contains at least one de-N-acetylated sialic acid residue adjacent an N-acylated (e.g., acetylated or propionylated) sialic acid residue or a sialic acid derivative residue. Examples of de-N-acetyl sialic acid antigens are provided in the present disclosure, and include, without limitation, de-N-acetylated polysaccharide derivatives ("PS derivatives"), de-N-acetylated gangliosides, and de-N-acetylated derivatives of a sialic-acid modified protein, particularly a sialic-acid modified protein that is accessible at an extracellular surface of a mammalian cell, particularly a human cell, more particularly a cancer cell, particularly a human cancer cell. deNAc SA epitopes are also present in polysaccharide capsules of *Neisseria*, especially *N. meningitidis*, particularly *N. meningitidis* Groups B and C, and *E. coli* K1. It should be noted that description of a deNAc SA antigen as a derivative of a starting molecule (e.g., PS derivative or ganglioside derivative) is not meant to be limiting as to the method of production of the de-N-acetyl sialic acid antigen, but rather is meant as a convenient way to describe the structure of the exemplary deNAc SA antigen.

The term "derivative" refers to without limitation any compound which has a structure derived from the structure of the compounds of the present disclosure and whose structure is sufficiently similar to those disclosed herein and based upon that similarity, would be expected, by one skilled in the art, to exhibit the same or similar activities and utilities as the claimed and/or referenced compounds.

The term "effective amount" of a compound as provided herein is intended to mean a non-lethal but sufficient amount of the compound to provide the desired utility. For instance, for eliciting an immune response in a subject to generate anti-deNAc SA antibodies, the effective amount is the amount which elicits a useful antibody response, e.g., so as to provide for production of antibodies that can be subsequently isolated (e.g., as in monoclonal antibody production) or to provide for a clinically meaningful immune response in a subject against a bacteria (e.g., as in the context of prophylactic or therapeutic immunization against a disease caused by *Neisseria* or *E. coli* K1) or by a cancer characterized by a deNAc SA epitope. For imparting a reduction in viability of a target cell in general, the effective amount is the amount which reduces viability or killing of the cell or provides for a clinically meaningful reduction in viable target cells in a subject, regardless of mechanism. As will be pointed out below, the exact amount required will vary from subject to subject, depending on the species, age, and general condition of the subject, the severity of the condition or disease that is being treated, the particular compound used, its mode of administration, and the like. Thus, it is not possible to specify an exact "effective amount." However, an appropriate effective amount may be determined by one of ordinary skill in the art using only routine experimentation.

The term "enriched" as used herein refers to a compound or composition that has an increase in the proportion of a desirable property or element. For example, an alpha (2→8) oligosialic acid derivative that is "enriched" for de-N-acetylation at a non-reducing end is an alpha (2→8) oligosialic acid derivative in which the de-N-acetylated residues are primarily present, including only present, at a non-reducing end, including the non-reducing terminal end. A composition is "enriched" for alpha (2→8) oligosialic acid derivatives having de-N-acetylated non-reducing ends where the majority of alpha (2→8) oligosialic acid derivatives in the composition (e.g., more than 50%, 55%, 60%, 65%, 70%, 75%, 80%, 85%, 90%, 95% or more up to 100%) have a de-N-acetylated residue at a non-reducing end, particularly at a non-reducing terminal end.

The term "immunotherapy" refers to treatment of disease (e.g., *Neisseria* or *E. coli* K1 bacterial infection, cancer) by modulating an immune response to a disease antigen. In the context of the present application, immunotherapy refers to providing an antibacterial and/or anti-cancer immune response in a subject by administration of an antibody (e.g., a monoclonal antibody) and/or by administration of an antigen the elicits an anti-tumor antigen immune response in the subject.

The term "inactivation" of a cell is used herein to indicate that the cell has been rendered incapable of cell division to form progeny. The cell may nonetheless be capable of response to stimulus and/or biosynthesis for a period of time, e.g., to provide for production of a cell surface molecule (e.g., cell surface protein or polysaccharide).

The term "in combination with" as used herein refers to uses where, for example, a first therapy is administered during the entire course of administration of a second therapy; where the first therapy is administered for a period of time that is overlapping with the administration of the second therapy, e.g. where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

The term "isolated" is intended to mean that a compound is separated from all or some of the components that accompany it in nature. "Isolated" also refers to the state of a compound separated from all or some of the components that accompany it during manufacture (e.g., chemical synthesis, recombinant expression, culture medium, and the like).

The term "monoclonal antibody" refers to an antibody composition having a homogeneous antibody population. The term is not limited by the manner in which it is made. The term encompasses whole immunoglobulin molecules, as well as Fab molecules, F(ab')2 fragments, Fv fragments, single chain fragment variable displayed on phage (scFv), fusion proteins comprising an antigen-binding portion of an antibody and a non-antibody protein, and other molecules that exhibit immunological binding properties of the parent monoclonal antibody molecule. Methods of making polyclonal and monoclonal antibodies are known in the art and described more fully below.

The term "non-reducing end" of an oligo or polysaccharide chain is intended the end portion of the chain bearing the non-reducing glycosyl residue.

The term "reducing end" of an oligo or polysaccharide chain is intended the end portion of the chain bearing the reducing glycose residue. This is the end of the chain which can be in equilibrium with the open chain aldehyde or ketone form of the saccharide.

The term "pharmaceutically acceptable" refers to a material that is not biologically or otherwise undesirable, i.e., the material is of a medically acceptable quality and composition that may be administered to an individual along with the selected active pharmaceutical ingredient without causing any undesirable biological effects or interacting in a deleterious manner with any of the other components of the pharmaceutical composition in which it is contained.

The term "pharmaceutically acceptable excipient" as used herein refers to any suitable substance which provides a pharmaceutically acceptable vehicle for administration of a compound(s) of interest to a subject. "Pharmaceutically acceptable excipient" can encompass substances referred to as pharmaceutically acceptable diluents, pharmaceutically acceptable additives and pharmaceutically acceptable carriers.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, $\beta$-galactosidase, luciferase, etc.; and the like. Polypeptides may be of any size, and the term "peptide" refers to polypeptides that are 8-50 residues (e.g., 8-20 residues) in length.

The term "purified" is intended to mean a compound of interest has been separated from components that accompany it in nature and provided in an enriched form. "Purified" also refers to a compound of interest separated from components that can accompany it during manufacture (e.g., in chemical synthesis, recombinant expression, culture medium, and the like) and provided in an enriched form. Typically, a compound is substantially pure when it is at least 50% to 60%, by weight, free from organic molecules with which it is naturally associated or with which it is associated during manufacture. Generally, the preparation is at least 75%, more usually at least 90%, and generally at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a compound that binds an antibody of interest. Purity can be measured by any appropriate method, e.g., chromatography, mass spectroscopy, HPLC analysis, etc.

The term "SEAM 3-reactive antigen" refers to an antigen having an epitope that is specifically bound by the monoclonal antibody (mAb) SEAM 3 (ATCC Deposit No. HB-12170). Exemplary SEAM 3-reactive antigens are provided in the working examples.

By "degree of polymerization" or Dp is intended the number of repeat units in an average polymer chain. Chain length can be reported in monomer units, as molecular weight, or both.

The term "subject" is intended to cover humans, mammals and other animals which contain polysialic acid in any fashion. The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

In the context of cancer therapies and diagnostics described herein, "subject" or "patient" is used interchangeably herein to refer to a subject having, suspected of having, or at risk of developing a tumor, where the cancer is one associated with cancerous cells expressing a de-N-acetyl sialic acid antigen. Samples obtained from such subject are likewise suitable for use in the methods of the present disclosure.

A "cancer cell" as used herein refers to a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", and encompasses cancer cells of a solid tumor, a semi-solid tumor, a primary tumor, a metastatic tumor, and the like.

As used herein, the terms "determining," "measuring," and "assessing," and "assaying" are used interchangeably and include both quantitative and qualitative determinations.

It is further noted that the claims may be drafted to exclude any optional or alternative element. As such, this statement is intended to serve as antecedent basis for use of such exclusive terminology as "solely", "only" and the like in connection with the recitation of claim elements, or the use of a "negative" limitation.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed. To the extent a definition of a term set out in a document incorporated herein by reference conflicts with the definition of a term explicitly defined herein, the definition set out herein controls.

In further describing the invention, the methods are described first in greater detail, followed by a review of the various specific methods of production, compositions, formulations, kits and the like that may find use in the methods, as well as a discussion of representative applications in which the methods and compositions find use.

Methods of Increasing Antigen on a Cell

As summarized above, the present disclosure provides methods of increasing a de-N-acetyl sialic acid antigen on a mammalian cell. The methods find use in facilitating binding of an antibody to a mammalian cell, eliciting antibodies to a mammalian cell as well as more specific applications including use in various methods of treating a host suffering from disease or condition in need thereof (as described in greater detail below).

A featured aspect involves use of a polysialic acid derivative of the present disclosure in a method for increasing antigen on a cancer cell. This method involves contacting the cancer cell with an effective amount of a composition that includes an antigen so as to increase the amount of the antigen on the cell. The antigen comprises a polysialic acid derivative having a mixture of N-acetyl and de-N-acetyl residues and that is resistant to degradation by exoneuraminidase (as described in greater detail below). An antigen of particular interest for use in this method is one in which the composition is enriched with polysialic acid derivative having a non-reducing end that is enriched for de-N-acetyl residues. In a specific embodiment, the polysialic acid derivative is an aggregate. The aggregates can be molecular aggregates or microscopic aggregates. Aggregates of specific interest are particles, such as a microscopic particle. This includes an aggregate that is capable of being more readily taken up by the cell and expressed on the cell surface compared to the corresponding non-aggregated derivative. By "corresponding non-aggregated derivative" is intended the same derivative found in the aggregate in reference. Aggregates are described in more detail below.

In a related embodiment, the polysialic acid derivative employed in the method is, or is capable of being expressed as a substantially intact antigen on the surface of the cancer cell. This includes, for example, a poly alpha (2→8) or poly alpha (2→9) N-acetyl neuraminic acid that contains a mixture of N-acetyl and de-N-acetyl residues, and thus an antigen that comprises a de-N-acetylated sialic acid epitope. Cancer cells of interest include neuroblastoma, leukemia, and melanoma cells. In one embodiment, the cell is in a subject, such as a human, and is contacted with antigen by administering to the subject an effective amount of a composition that comprises a polysialic acid derivative of the present disclosure. Various formulations, routes of administration and dosing are described in more detail below. In a specific embodiment, the polysialic acid derivative is an aggregate, as described above and in more detail below.

Another method of the present disclosure is facilitating binding of an antibody to a mammalian cell. This method involves increasing the amount of the antigen on a cell as noted above, and then contacting the cell with an antibody that is specific for the antigen so as to facilitate binding of the antibody to the cell. This aspect includes various embodiments such as where binding of the antibody to the cell is increased, where antibody binding to the cell facilitates uptake of the antibody by the cell, and where uptake of the antibody by the cell is increased. An additional embodiment is one in which binding of the antibody to the cell is cytotoxic, i.e., toxic to cells, including arresting growth, inducing apoptosis, and/or inducing cell death. In a specific embodiment, the antibody is specific for a de-N-acetylated sialic acid epitope. An example of an antibody suitable for this purpose is SEAM 3.

Antibody employed in the methods of the present disclosure can be a conjugate of a first molecule to one or more second molecules, such as a detectable label, a cytotoxic drug, a toxin, such as an immunogenic toxin, and the like, such as described in more detail below. Here again, cells of interest include cancer cells such as neuroblastoma, leukemia, and melanoma cells, and where the cell can be in vitro or in vivo.

For instance, when in vitro, the cell can be in a format isolated or separated from its normal environment, such as a cultured cell line and the like. When the cell is in vitro, an effective amount of the antigen can be exogenously applied to the cell so as to facilitate expression of the antigen on the cell surface, and then the antibody can be brought into contact with the cell using an effective amount so as to facilitate binding of the antibody to the cell. It will also be appreciated that the conditions under which in vitro binding is facilitated can be adjusted and are routine, for example, in various cell culture assays and diagnostic procedures (e.g., such as the flow cytometry, ELISA and Western Blot assays described herein), affinity purification schemes and the like.

When in vivo, the cell is in a subject, such as a human, and is contacted with antigen by administering to the subject an effective amount of a composition that comprises a polysialic acid derivative of the present disclosure. In some embodiments, contacting with the antibody may also be in vitro or in vivo. For instance, when the antibody is exogenously applied to a cell in a subject, the method may involve administering to the subject an effective amount of the antibody so as to affect binding of the antibody to the cell. Alternatively, the antibody may be one that is elicited by the subject, such as described below, or a combination of exogenously applied and internally elicited and thus brought into contact with antigen on the surface of a cell in vivo in this manner. Various formulations, routes of administration and dosing for in vivo applications are described in more detail below.

The present disclosure also includes methods of eliciting antibody to a cell in a subject. This method involves administering to the subject an effective amount of an immunogenic composition that includes an antigen so as to increase expression of the antigen by the cell in the subject. This embodiment employs an antigen that comprises a polysialic acid derivative having a mixture of N-acetyl and de-N-acetyl residues and that is resistant to degradation by exoneuraminidase. A specific feature of this method is where the antigen is an aggregate of the polysialic acid derivative, as described above and in more detail below. The administering is effective to elicit production of an antibody in the subject that specifically binds to the cell. In one embodiment, binding of the elicited antibodies to the cell can be cytotoxic, and thus arrest cell growth, induce apoptosis, and/or induce cell death. Typically, the antibody is specific for a de-N-acetylated sialic acid epitope, and thus the antigen comprises de-N-acetylated sialic acid epitope. In a specific embodiment, the antigen is expressed on the surface of a cancer cell such as neuroblastoma, leukemia, or melanoma cell.

An additional method is for reducing the viability of a cancer cell. This method involves contacting a cancer cell with an effective amount of a composition comprising a polysialic acid derivative of the present disclosure so as to reduce the viability of the cell. In this embodiment, the polysialic acid derivative has a reducing end and a non-reducing end, and is a substantially unoxidized and purified oligosaccharide. The substantially unoxidized and purified oligosaccharide comprises (i) a mixture of N-acetyl sialic acid and de-N-acetyl sialic acid residues, and (ii) a de-N-acetyl sialic acid residue at the non-reducing end that is resistant to degradation by exoneuraminidase. In a particular embodiment, intracellular uptake by the cancer cell of the polysialic acid derivative is cytotoxic to the cancer cell. The effective amount of the polysialic acid derivate as applied to be cytotoxic to the cell is generally a concentration higher than is required to elicit antibody against the antigen generated by application of the polysialic acid derivative, and is usually at a concentration that forms an aggregate, such as a cooperatively formed high molecular weight complex. Cells of particular interest include cancer cells, such as neuroblastoma, leukemia, and melanoma cells, and the cell can be in vitro or in vivo.

Methods of Production and Compositions

As summarized above, the disclosure provides methods of producing isolated poly alpha (2→8) N-acetyl neuraminic acid compositions that contain a mixture of N-acetyl and de-N-acetyl residues (that is, neuraminic acid-containing polysialic acid) suitable for use in the methods. This includes polysialic acid derivatives having a mixture of N-acetyl and de-N-acetyl residues and that are resistant to degradation by exoneuraminidase, as well as those that additionally bear a non-reducing end enriched for de-N-acetyl residues, as well as compositions enriched with such polysialic acid derivatives. As used herein and unless specified otherwise, the term "polysialic acid" refers to alpha (2→8) and alpha (2→9) polysialic acid. Thus, for example, a polysialic acid derivative of the invention includes those that comprise a polymer of sialic and neuraminic acid monomers joined essentially through alpha (2→8) or alpha (2→9) glycosidic linkages. One or more of the sialic and neuraminic acid monomers of a polysialic acid may be modified or conjugated to a second molecule, such as a partially or fully O-acetylated monomer of sialic and/or neuraminic acid. The compositions also include aggregates of the polysialic acid derivatives, as well methods of their production.

One feature of the methods of production is that, unlike approaches which typically focus on incorporation non-native moieties such as N-propionyl groups, the present methods are exploited to generate derivatives with mixtures of natural N-acetyl (e.g., as found in sialic acid) and de-N-acetyl (e.g., as found in neuraminic acid) moieties to resemble antigens that are uniquely expressed on the surface of various bacterial and cancer cells. Another feature of the methods is that they yield polysialic acid derivatives resistant to degradation by exoneuraminidase, and can be exploited in particular embodiments to impart non-reducing ends enriched with de-N-acetyl groups. Another aspect of the methods is that aggregates of the polysialic acid derivatives are more readily taken up by cells and expressed on the cell surface compared to the corresponding non-aggregated derivative. It is believed that these various structural properties of the compositions described herein can uniquely translate into the functional properties observed upon their exogenous application to cells, including their ability to be readily taken up by a cell and presented on the cell surface as a substantially intact antigen. For instance, the appearance of substantially intact antigen on the cell surface following exogenous exposure of the cells to a polysialic acid derivative of the present disclosure was observed relative to controls by various techniques as illustrated in the Examples.

In particular, a specific method contemplated herein for the production of an isolated polysialic acid derivative involves: (i) providing a first composition comprising de-N-acetylated polysialic acid; (ii) re-N-acetylating said de-N-acetylated polysialic acid to generate a second composition comprising partially re-acetylated polysialic acid having a mixture of N-acetyl and de-N-acetyl residues; and then (iii) isolating from the second composition polysialic acid derivative resistant to degradation by exoneuraminidase.

Polysialic acid precursors of particular interest are homopolymers, such as a homopolymer of sialic acid, for example, colominic acid, and can be derived from natural sources or synthetic. In another embodiment, the polysialic acid precursors can be obtained from polysialic acid of $N.$ $meningitidis$ or $E.$ $coli$ K1, or other suitable source of bacterial polysialic acid. Thus, depending on the precursor material selected, the N-acetyl and de-N-acetyl residues can be advantageously selected. For example, in one embodiment, the de-N-acetyl residue is neuraminic acid. In another embodiment the N-acetyl residue is sialic acid. In another embodiment, the polysialic acid derivative is a homopolymer of neuraminic acid and sialic acid. In other embodiments, the N-acetyl and/or de-N-acetyl neuraminic acid is O-acetylated at one or more positions, such as for a polysialic acid precursor obtained from polysialic acid of $N.$ $meningitidis$ Serogroup C in which C7 and C8 are O-acetylated in the naturally occurring material. In this regard, the present disclosure provides for control of the level of acylation of the final product, and in particular, the ability to generate polysialic acid derivative that contains the desired mixture of de-N-acetyl and N-acetyl residues.

This includes a related embodiment in which the polysialic acid precursor is selected so as to generate polysialic acid derivative that contains about 10% to 30% de-N-acetyl residues, about 70% to 90% N-acetyl residues, and in some instance, such as noted above, non-natural N-acyl derivatives in a proportion of about 10% to 20%. In some embodiments, the polysialic acid precursor is selected so as to generate a polysialic acid derivative containing about 10% to 80% de-N-acetyl residues, usually about 10% to about 60%, and in certain embodiments, about 1, 2, 3, 4 or 5 de-N-acetyl residues per polysialic acid chain, and in specific embodiments, about 1 de-N-acetyl residues per polysialic acid chain. The present disclosure also includes a polysialic acid precursor selected so as to generate a polysialic acid derivative that contains a non-reducing end de-N-acetyl residue linked through a glycosidic bond to a residue selected from an N-acetyl residue and an N-acylated residue other than an N-acetyl group, and where the polysialic acid derivative is substantially unoxidized and purified oligosaccharide having a degree of polymerization of about 2-10.

In a related embodiment, the polysialic acid precursor of the present disclosure can also be modified with various non-natural N-acyl groups. For instance, the polysialic acid precursor may be the product of biosynthesis of a polysialic acid in cell culture where the growth media is supplemented with a mixture of mannosamine derivatives (e.g., N-trihaloacyl mannosamine) and acyl mannosamine (e.g., N-trihaloacetyl and N-acetyl mannosame) in a desired ratio such that the precursor material expressed by the cells contains the desired mixture of de-N-acetyl and N-acetyl residues, as well as the desired amount of non-natural N-acyl groups. For example, the precursor material in a specific embodiment is selected so as to yield polysialic acid derivative to comprise about 10% to 30% de-N-acetyl residues. Another example is where the precursor material is selected to generate a polysialic acid derivative containing about 10% to 80% de-N-acetyl residues, usually about 10% to about 60% de-N-acetyl residues, and in some instances about 1, 2, 3, 4 or 5 de-N-acetyl residue per polysialic acid chain, and in specific embodiments, about 1 de-N-acetyl residues per polysialic acid chain. An additional example is where the polysialic acid precursor selected so as to generate a polysialic acid derivative containing a non-reducing end de-N-acetyl residue linked through a glycosidic bond to a residue selected from an N-acetyl residue and an N-acylated residue other than an N-acetyl group, and where the polysialic acid derivative is substantially unoxidized and purified mannosamine containing oligosialic acid having a degree of polymerization of about 2-10.

In the re-N-acylation step of the method, partial re-N-acylation provides for production of a polysialic acid derivative having fewer than 90%, fewer than 85%, fewer than 84%, fewer than 80%, fewer than 75%, fewer than 70%, fewer than 60%, or fewer than 55%, usually about 10%, about 15%, about 16%, about 20%, about 25%, about 30%, about 40%, or about 45% N-acylated residues relative to the total residues of the compound. In this regard, the methods can provide for control of the level of acylation of the final product, so as to provide polysialic acid derivative having a desired level of acylation. In general, reacylation is controlled or prevented by limiting the amount of acylating reagent. As noted above, a particular embodiment of interest is polysialic acid derivative having about 10% to 30% de-N-acetyl residues.

Other approaches are possible as well, including re-N-acylation with a mixture of amine protected group and acyl groups (e.g., trihaloacetyl and acetyl groups) in a desired ratio such that the polysialic acid derivative contains fewer than 90%, fewer than 85%, fewer than 84%, fewer than 80%, fewer than 75%, fewer than 70%, fewer than 60%, fewer than 55% amine protected residues, usually about 10%, about 15%, about 16%, about 20%, about 25%, about 30%, about 40%, or about 45% amine protected residues (e.g., N-trihaloacylated residues) relative to the total residues of the compound (where the compound generally contains at least 10 or at least 20 residues). In this regard, the present disclosure provides for control of the level of acylation of the final product after removal of the amine protecting group and avoiding undesirable side reactions with free amino groups, so as to provide a polysialic acid derivative having a desired level of acylation. Removal of the amine protecting groups for a free amine at the deprotected residue. In general, the proportion of de-N-acetyl residues is controlled by limiting the amount of amine protecting reagent (e.g, the amount of a trihaloacylting reagent). Here again, one embodiment of specific interest is the generation of polysialic acid derivative containing the desired mixture of de-N-acetyl and N-acetyl residues, as well as the desired amount of non-natural N-acyl group as noted above. CMP-N-acylated sialic acid analogs and sialyltransferases may also be used in a semi-synthetic approach (e.g., Wakarchuk et al. (2008) *Glycobiology* 18:177).

In a specific embodiment, the first composition of the method of production is provided by treating a polysialic acid precursor with a strong reducing agent (e.g., sodium borohydride) followed by a strong base (e.g., sodium hydroxide) under conditions suitable for de-N-acetylating the precursor. The strong reducing agent converts the reducing end to the un-reactive alcohol form, which is followed by treatment with strong base to de-N-acetylate the polymer.

The reaction mixture can then be purified by standard methods (e.g., dialysis in water and lyophilized followed by ion exchange) so as to isolate the desired material from byproduct, side reactions and the like. For example, the quality of the material and amount of sialic acid and de-N-acetyl sialic acid in the polysialic acid product may be determined at this point (e.g., by resorcinol assay, such as described in the Examples), and/or tested for its ability to be taken up and expressed as antigen on the surface of a cell, such as described below, for characterization, and release purposes and the like.

When coupled to the isolation of polysialic acid derivatives resistant to degradation by exoneuraminidase, the products are enriched with the desired material and particularly well suited for increasing the antigen content on the surface of a cell. A composition of particular interest generated by this method includes an isolated polysialic acid derivative having a non-reducing end that is enriched for de-N-acetyl residues and resistant to degradation by exoneuraminidase, as well as compositions that are enriched with mixtures of polysialic acid derivatives having a non-reducing end that is enriched for de-N-acetyl residues.

For instance, the method of production step of isolating polysialic acid derivative resistant to degradation by exoneuraminidase from the second composition typically involves exposing the partially re-acetylated polysialic acid to exoneuraminidase, and then purifying the desired polysialic acid derivative. Exoneuraminidase of particular interest is an exosialidase from *Arthrobacter ureafaciens* (SIALIDASE A™, Prozyme, Hayward, Calif.). In this aspect, exoneuraminidase (exosialidase) cannot degrade polysialic acid that terminates on the non-reducing end with a de-N-acetyl sialic acid residue (i.e., neuraminic acid) or one that is otherwise chemically blocked. Therefore, digestion of a preparation of a polysialic acid derivative that contains de-N-acetyl residues located throughout the polymer with an exoneuraminidase will result in degradation of the polysialic acid except when the exoneuraminidase encounters a de-N-acetyl residue. At that point, no further degradation of the polymer will occur. Also, the polysialic acid molecules that are not degraded are likely to have a de-N-acetyl sialic acid residue at the non-reducing end. Alternatively, the desired material can be isolated by standard purification of derivative under conditions that select for a terminal non-reducing end that is blocked from degradation by exoneuraminidase, such as a terminal neuraminic acid residue and the like.

Thus, in certain embodiments, the method of production can be used to directly produce a desired polysialic acid derivative resistant to degradation by exoneuraminidase from precursor material appropriate for this purpose. This method involves: (i) treating a first composition comprising polysialic acid derivative having a mixture of N-acetyl and de-N-acetyl residues with exoneuraminidase; and (ii) isolating from the first composition polysialic acid derivative resistant to degradation by said exoneuraminidase. This method is particularly suited when the precursor material is appropriately selected and/or prepared to contain a mixture of N-acetyl and de-N-acetyl residues, and then the desired product purified and isolated away from the degradation products so as to avoid unwanted side reactions such as re-acetylation, aldehyde and ketone side reactions, unwanted cross linking, as well as a wide range of other unwanted contaminants such as monomer and intermediates susceptible to exoneuraminidase degradation, or that otherwise alter the desired properties of the material. In this way the specific activity of the isolated polysialic acid derivative can be increased relative to unpurified material, and the benefits of higher specific activity exploited, including increased expression of the antigen of the surface of a cell when exogenously applied to the cell. By "specific activity" is intended the amount of antigen formed on the surface of a cell in a given amount of time under given conditions per unit (e.g., microgram) of exogenously applied polysialic acid derivative, or calculated as the concentration of polysialic acid derivative disappearing (or product produced) per unit time following exogenous administration of the polysialic acid derivative.

In a specific embodiment, the specific activity of a polysialic acid derivative having a mixture of de-N-acetyl and N-acetyl residues and that is resistant to degradation to exoneuraminidase is greater than a polysialic acid that is susceptible to exoneuraminidase degradation. In another embodiment, the specific activity of a polysialic acid derivative having a mixture of de-N-acetyl and N-acetyl residues and that is resistant to degradation to exoneuraminidase is greater than a polysialic acid that is not enriched for non-reducing end re-N-acetyl residues. In yet another embodiment, the specific activity of a polysialic acid derivative having a mixture of de-N-acetyl and N-acetyl residues and that is resistant to degradation to exoneuraminidase is greater than a polysialic acid that is susceptible to exoneuraminidase degradation and that is not enriched for non-reducing end re-N-acetyl residues. As can be appreciated, compositions produced by the present method generate polysialic acid derivatives with greater specific activity than previously observed for other derivatives, particularly with respect to the relative uptake and presentation of polysialic acid antigen on the cell surface as a substantially intact antigen.

In another specific embodiment, compositions of the present disclosure can be produced by (i) providing a solution comprising a mixture of polysialic acid derivatives each having: a different degree of polymerization, a different mixture of N-acetyl residues and de-N-acetyl residues, and a non-reducing end N-acetyl sialic acid residue; (ii) subjecting the solution to ion exchange chromatography to generate fractions; and (iii) isolating from one or more of the fractions a polysialic acid derivative having a defined degree of polymerization and a non-reducing end de-N-acetyl residue resistant to degradation by exoneuraminidase. In certain aspects, the mixture of polysialic acid derivatives further includes polysialic acid molecules having a non-reducing end N-acetyl group. In some embodiments, the polysialic acid derivative having a defined degree of polymerization is isolated in an individual fraction, or a pool of fractions formed by pooling selected fractions containing a polysialic acid derivative having a desired activity of interest. Of particular interest is an isolated polysialic acid derivative produced by the ion exchange method disclosed herein in which the isolated polysialic acid derivative (i) has a degree of polymerization in a range selected from about 2 to about 10, and (ii) decreases the viability of Jurkat T-cell leukemia cells by at least about 20% when the isolated polysialic acid derivative is exogenously applied to the cells in an aqueous solution at a concentration of about 0.01 mM to about 15 mM, usually about 0.5 mM to about 10 mM, and where the decrease in viability is relative to control Jurkat T-cell leukemia cells that are not exogenously exposed to the derivative.

In particular embodiments, ion exchange chromatography is carried out at a pH range of between about 6.5 and about 10.0. In a specific embodiment, the ion exchange chromatography is anion exchange chromatography. In some embodiments, the anion exchange chromatography is high pH anion-exchange chromatography (HPAC). In certain embodiments, the anion exchange chromatography utilizes DEAE, TMAE, QAE, or PEI. In other embodiments, the anion exchange chromatography utilizes Toyopearl Super Q 650M, MonoQ, Source Q or Fractogel TMAE. A particular ion exchange chromatography procedure of interest employs a resin such as Q Sepharose™ Fast Flow (strong anion), SP Sepharose™ Fast Flow (strong cation), CM Sepharose™ Fast Flow (weak cation), DEAE Sepharose™ Fast Flow (weak anion), and ANX Sepharose™ 4 Fast Flow (high sub) (weak anion) (e.g., available from GE Healthcare Bio-Sciences Corp., Piscataway, N.J.). Of specific interest are strong anion exchangers, such as Q Sepharose™ Fast Flow. Sample/loading buffer and elution system for such ion exchange columns and systems are generally selected for resolving the isolation of a particular compound of interest.

An example of a general buffer system for a Q Sepharose™ Fast Flow anion exchange resin is a sample/loading buffer system of 20 mM Bis-Tris buffer, pH 8, and an elution buffer system composed of a 0M to 0.2M gradient of sodium chloride in 20 mM Bis-Tris buffer, which can be eluted at different flow rates depending on column dimensions and the like. The ion exchange fractions containing a de-N-acetyl and N-acetyl sialic acid material of interest can be analyzed with great sensitivity by high pH anion-exchange chromatography with pulsed amperometric detection (HPAC-PAD) (e.g., Townsend, R. R. (1995) Analysis of glycoconjugates using high-pH anion-exchange chromatography. J. Chromatog. Library 58, 181-209; and Manzi et al., (1990) HPLC of sialic acids on a pellicular resin anion exchange column with pulsed amperometry. Anal. Biochem. 188, 20-32). The isolated material may be purified further by one or more orthogonal chromatography techniques such as gel permeation, size exclusion, RP-HPLC and the like. If desired, the isolated polysialic acid material can be subjected to one or more of further preparatory steps, such dialysis, lyophilization, crystallization, formulation and the like.

The ion exchange and purification method described above can be carried out on a mixture of polysialic acid derivative that is produced by treating a first composition comprising a polysialic acid derivative having a mixture of N-acetyl and de-N-acetyl residues with exoneuraminidase. The method may also be carried out on a mixture of re-acetylated polysialic acid derivatives, such as produced by re-acetylating a first composition comprising de-N-acetylated polysialic acid to generate a second composition, the second composition comprising partially re-acetylated polysialic acid having: a mixture of N-acetyl and de-N-acetyl residues, and which is resistant to degradation by exoneuraminidase.

In a particular embodiment of interest, the ion exchange and purification method described above is applied in the production and purification of isolated polysialic acid derivative that is substantially unoxidized and defined so as to have few side products in the initial material subjected to ion exchange purification. For instance, unwanted oxidation of polysialic acid generates multiple overlapping degradation and side reaction products that can be difficult to resolve and separate from the desired material by ion exchange chromatography. As such, "substantially unoxidized" is intended mean that the polysialic acid derivative, excepting normal isomer or tautomer equilibriums, contains less than about 20%, less than about 15%, less than about 10%, less than about 5% oxidized saccharide residues, and usually about 80%, about 85%, about 90%, about 95% or greater unoxidized sacchardide residues. Of specific interest is a total chemical synthesis method that generates an initial product containing few side reaction products, and facilitates the purification of smaller polysialic acid derivatives of defined length and composition.

In certain embodiments, the substantially unoxidized and defined polysialic acid derivative is produced by time-controlled de-N-acetylation and/or non-oxidizing acid hydrolysis of a polysialic acid precursor material of interest. A featured aspect is a chemical synthesis method for the production of a substantially unoxidized and defined polysialic acid derivative, where the method involves either (i) non-oxidizing acid hydrolysis of partially de-N-acetylated polysialic acid prepared by reduced time-controlled alkaline hydrolysis, or (ii) partial de-N-acetylation of polysialic acid by reduced time-controlled alkaline hydrolysis followed by non-oxidizing acid hydrolysis.

Partial de-N-acetylation of polysialic acid by time-controlled alkaline hydrolysis involves (i) treating a polysialic acid precursor with a strong reducing agent in a strong base under conditions suitable for partially de-N-acetylating the precursor, where the treating is for a period of time effective to generate a minimally degraded product of partially de-N-acetylated polysialic acid. In certain embodiments, the period of time for treatment is about 1 hour or less, generally ranging from about 5-55 minutes in one minute increments, such as ranging from about 10-50 minutes, 15-45 minutes, 20-40 minutes, and usually about 40 minutes. Thus, the reaction time can be selected to provide for minimally degraded product, generating desired fractions of partially de-N-acetylated polysialic acid separatable by ion exchange chromatography. An example of a suitable strong reducing agent for this procedure is sodium borohydride, sodium cyanogen borohydride and the like (i.e., reagents that easily lose (or donate) electrons, such as in approximate increasing order of strength: sodium cyanogen borohydride~sodium triacetoxyborohydride, sodium borohydride, lithium tri-sec-butylborohydride, and lithium aluminum hydride). An example of a suitable strong base is sodium hydroxide (i.e., a base which hydrolyzes completely, raising the pH of the solution towards 14, and thus a base having a pKa of more than about 13, such as in approximate increasing order of strength: potassium hydroxide, barium hydroxide, cesium hydroxide, sodium hydroxide, strontium hydroxide, calcium hydroxide, lithium hydroxide, and rubidium hydroxide). The reaction may also be aided by selecting an appropriate temperature, usually ranging from about 70° C.-120° C., about 80° C.-110° C., and more typically about 90° C.-100° C. As such, alkaline de-N-acetylation can be carried out for different reaction times to generate de-N-acetyl polysialic acid containing defined amounts of de-N-acetyl sialic acid residues throughout the polymer precursor, and to generate discrete fractions with minimal overlapping degradation products. In addition, the time-controlled partial alkaline de-N-acetylation procedure can generate polysialic acid derivative containing desired amounts of de-N-acetyl residues, for example, about 25%-60% de-N-acetyl residues.

Non-oxidizing acid hydrolysis can be carried out to increase the fraction of chains containing de-N-acetyl sialic acid at the non-reducing end, since the glycosidic bond at the reducing end of a de-N-acetyl sialic acid residue in polysialic acid is resistant to hydrolysis while the bond at the non-reducing end of the residue is not. In addition, performing the acid hydrolysis reaction under such non-oxidizing conditions minimizes oxidative damage to the polysaccharide that can occur in the presence of strong acid or high concentrations (10%) of acetic acid. Furthermore, non-oxidizing acid hydrolysis facilitates the production of smaller oligosialic acid (or oligosaccharide) derivatives enriched for de-N-acetyl sialic acid residues at the non-reducing end. This aspect involves (i) exposing a polysialic acid precursor or a partially de-N-acetylated polysialic acid under acidic conditions capable of selectively hydrolyzing a glycosidic bond of the polysialic acid, where the acidic conditions include a buffer solution in which dissolved gasses have been evacuated (e.g., by alternately freezing and thawing the solution under vacuum). Anti-oxidants and free radical scavengers may also be added to the reaction mixture to further reduce the oxidizing environment of the reaction solution. In addition to the non-oxidizing conditions, the acidic buffer system generally includes those suitable for acid-based polysialic acid hydrolysis reactions, for example, 0.1 M sodium acetate buffer, pH 5.5. Additional examples of acidic conditions include hydrochloric acid (e.g., 20 mM HCl) and trifluroacetic acid (e.g., 0.1 M TFA). The non-oxidizing acid hydrolysis reaction can be carried out for different periods of time, for a given end use, which is usually about 1-30 hours, 5-25 hours, 10-20 hours, and generally about 15-18 hrs. The temperature of the reaction may also be adjusted to aid control of the reaction. Examples of suitable a temperature range is about 25° C. or greater, such as a temperature range of about 40° C. to 90° C., usually about 50° C. to 70° C. As such, the non-oxidizing acid hydrolysis method is well suited for generating shorter length polysialic acid derivatives having a non-reducing end de-N-acetyl residue and a desired degree of polymerization, including for example, products with a defined degree of polymerization of about 2-20, usually of about 2-10.

Hence the products produced by the methods include certain features useful for imparting an ability to be processed and presented on the surface of a cell as a substantially intact antigen. Among these features, as noted above, is an isolated polymer or composition enriched with isolated polymers having a mixture of de-N-acetyl and N-acetyl residues and that is resistant to degradation to exoneuraminidase. Thus one feature that can improve presentation of the antigen includes the purity of the material itself. For example, in a specific embodiment, the isolating steps of the production methods of the present disclosure can generate product that is substantially free of contaminants, and thus enriched for the desired derivative relative to non-enriched controls. This includes polysialic acid derivatives that have an increase in the proportion of a desirable property or element. For example, isolation of a desired polysialic acid derivative is where the polysialic acid of interest represents the majority of the desired material (e.g., more than 50%, 55%, 60%, 65%, 70%, 75%, 80%, 85%, 90%, 95% or more up to 100%). This of course includes mixtures of polysialic acid derivatives having variable chain lengths, provided that the majority of chains each individually contain a mixture of de-N-acetyl and N-acetyl residues and that is resistant to degradation to exoneuraminidase, as well as mixtures with these features and the additional feature of having a non-reducing end that is enriched for de-N-acetyl residues, including for instance a de-N-acetylated residue at the non-reducing terminal end (i.e., a non-reducing end de-N-acetyl sialic acid residue).

Again, depending of the specific approach, polysialic acid derivative can be produced to have various beneficial structural and related functional properties, such as a non-reducing end having one or more de-N-acetyl residues, a terminal de-N-acetyl residue and the like. As noted above, a de-N-acetyl residue of specific interest is neuraminic acid, and thus the terminus of the non-reducing end can be neuraminic acid. As also noted above, the methods can be exploited to produce polysialic acid derivative in which the non-reducing end is enriched with de-N-acetyl residues, as well as homopolymers of neuraminic and sialic acid and the like. Polysialic acid derivative may also be produced so as to comprise about 10% to 30% de-N-acetyl residues, or in certain embodiments, about 10% to 80% de-N-acetyl residues, and typically about 10% to 70%, about 25% to 65%, about 40% to 60% to a convergence of about 50% de-N-acetyl residues, as well as polysialic acid derivative that comprise a mixture of polysialic acid derivative chains of variable length. In certain embodiments, the methods of production are suitable to produce a polysialic acid having about 1, 2, 3, 4 or 5 de-N-acetyl residue per polysialic acid derivative chain, and in specific embodiments, about 1 de-N-acetyl residue per polysialic acid derivative chain. In addition, the production methods of the present disclosure may be employed to generate polysialic derivatives having a defined degree of polymerization, particularly for shorter polysialic acid derivatives, such as oligosialic acid derivatives having a degree of polymerization of about 2 to about 20, such as a degree of polymerization of about 2, 3, 4, 5, 6, 7, 8, 9, 10, 11, 12, 13, 14, 15, 16, 17, 18, 19, 20 or 21. The compositions of the present disclosure include polysialic acid derivatives with these features.

Compositions of particular interest include an isolated polysialic acid derivative that is substantially unoxidized and comprises (i) a mixture of N-acetyl sialic acid and de-N-acetyl sialic residues, and (ii) a non-reducing end de-N-acetyl residue that is resistant to degradation by exoneuraminidase, where the composition is substantially free of polysialic acid having a non-reducing end N-acetyl sialic acid residue. By composition is "substantially free of polysialic acid having a non-reducing end N-acetyl sialic acid residue" is intended to mean that the composition contains less than about 20%, less than about 15%, less than about 10%, or less than about 5% non-reducing end N-acetyl residues, and usually about 80%, about 85%, about 90%, about 95% or greater non-reducing end de-N-acetyl residues.

In some embodiments, the isolated polysialic derivative of the composition has a degree of polymerization of about 2-20, such as a degree of polymerization selected from 2, 3, 4, 5, 6, 7, 8, 9, 10, 11, 12, 13, 14, 15, 16, 17, 18, 19, 20 and 21. In specific embodiments, the isolated polysialic derivative of the composition has a degree of polymerization of about 2-10, about 2-9, about 2-8, about 2-7, about 2-7, about 2-6, about 2-5, about 2-4, about 2-3, or about 2. This includes particular embodiments where the degree of polymerization is of a range of about 3-5, about 3-6, about 3-7, about 3-8, about 4-6, about 4-8, or about 4-10.

The isolated polysialic acid derivative of the compositions disclosed herein generally contains about 10% to 80% de-N-acetyl residues, usually about 10% to about 60% de-N-acetyl residues, and in some instances about 1, 2, 3, 4 or 5 de-N-acetyl residue per polysialic acid chain, and in specific embodiments, about 1 de-N-acetyl residues per polysialic acid chain. An additional example is an isolated polysialic acid derivative of the composition can contain a non-reducing end de-N-acetyl residue linked through a glycosidic bond to a residue selected from an N-acetyl residue and an N-acylated residue other than an N-acetyl group, and where the polysialic acid derivative is substantially unoxidized and purified. Of particular interest is a composition having an isolated polysialic acid derivative that (i) has a degree of polymerization of a range selected from about 2 to about 10, and (ii) decreases the viability of Jurkat T-cell leukemia cells by at least about 20% when the isolated polysialic acid derivative is exogenously applied to the cells in an aqueous solution at a concentration of about 0.01 mM to about 15 mM, usually about 0.5 mM to about 10 mM, and where the decrease in viability is relative to control Jurkat T-cell leukemia cells that are not exogenously exposed to the derivative.

In certain embodiments, the isolated polysialic derivative of the composition can comprise at least one dimer of de-N-acetyl sialic acid and N-acetyl sialic acid linked through a glycosidic bond selected from α(2→8) and α(2→9). Aspects of the composition include a polysialic acid derivative in which the non-reducing end de-N-acetyl sialic acid residue is linked through a glycosidic bond to an N-acetyl sialic acid residue. A featured aspect is where the de-N-acetyl sialic acid is neuraminic acid, and the N-acetyl sialic acid is N-acetyl neuraminic acid. A related embodiment is where at least one of the neuraminic acid and N-acetyl neuraminic acid residues comprises at least one O-acetylated group. In a particular embodiment of interest, the isolated polysialic acid derivative is derivable from a capsular polysaccharide homopolymer of a bacterium selected from *Escherichia coli* K1, *Escherichia Coli* K92, *Neisseria meningitidis* Serogroup B, *Neisseria meningitidis* Serogroup C, *Haemophilus ducreyi*, *Campylobacter jejuni*, *Moraxella catarrhalis*, *Streptococcus algalactiae*, and *Paterurella multocidae*. Additional suitable polysialic acid materials may be employed (Troy, F., *Sialobiology and the Polysialic Acid Glycotype: Occurrence, Structure, Function, Synthesis, and Glycopathology*, Chpt. 4, pp. 95-133, In Biology of Sialic Acids, Abrahman Rosenburg, Ed., Springer, 1995). Aggregates the compounds, and compositions containing same, are also of interest.

Another embodiment is a method of producing a composition comprising an aggregate of one or more polysialic acid derivatives, as well as the compositions produced by the methods. This method involves exposing a polysialic acid derivative to an aggregating condition so as to form an aggregate. Thus the methods of production described above may further include the step of forming an aggregate of the isolated polysialic acid derivative. Examples of the aggregating conditions include heating, addition of an excipient that facilitates aggregation, and the like.

By "aggregate" is intended a particle comprising an aggregated complex of individual monomers of a molecule and having a combined molecular weight that is a multiple of the molecular weight of an individual monomer of the complex. For example, an aggregate of one or more monomers of a polysialic acid derivative include an aggregate complex having a particle molecular weight that is 10× or more of the molecular weight of an individual monomer in the aggregated monomer complex. This includes an aggregate having a particle with a molecular weight of greater than about 50,000, to greater than about 250,000 Daltons, to greater than 500,000 Daltons, to greater than 750,000 Daltons, to greater than 1,000,000 Daltons up to a particle having a uniform particle size that is readily visible by light microscopy, e.g., under a standard low magnification light microscope (e.g., 40× magnification).

Thus, the aggregate can be a molecular or microscopic particle. For microscopic particles, the optimal aggregate can be selected by varying the mean aggregate diameter, e.g., 1 um to 20 μm, and usually about or smaller than the diameter of a cell targeted for exposure and uptake of the material of interest, e.g., cells are usually approximately 1-20 μm in diameter. For non-visible molecular particles, as well as the microscopic particles, the desired aggregate can be selected by measuring uptake and internalized by cells. In each instance, the aggregate of the polysialic acid derivative is capable of being taken up and internalized by cells better than non-aggregated derivative relative to each other, a control, and/or both.

As noted above, the aggregate can be formed by admixing a non-aggregated forms of one or more polysialic acid derivatives under aggregating conditions, by partial degradation or partial hydrolysis of a polysialic acid derivative under aggregating conditions, forming an aggregate of the polysialic acid derivative with an aggregating excipient, or a combination thereof. By "aggregating condition" is intended chemical-physical conditions that cause an otherwise soluble material to form an aggregated substance in solution. For instance, a polysialic acid derivative can be heated (e.g., 30° C.-70° C.) for an appropriate period of time (e.g., 1 hr to overnight) so as to form an aggregate. Typically, the temperature and duration of exposure are selected to reduce or inhibit microbial growth (e.g., reduce the potential for contamination) while not destroying the desired activity of the aggregate.

In another embodiment, the polysialic acid derivative comprises a non-reducing end that is a de-N-acetyl residue, such as neuraminic acid, and the aggregate is formed by exposing the derivative to aggregating conditions. Treatment with exoneuraminidase enriches for non-reducing end de-N-acetyl residues which aggregate when heated forming particles that are readily taken up by cells. This also applies to other polymers of sialic acid, including non-derivatized polysialic acid as well as derivatized polysialic acid. Accordingly, the present disclosure also provides a method of producing an aggregate of a polysialic acid or polysialic acid derivative. This method involves treating a polysialic acid or polysialic acid derivative exoneuraminidase so as to generate polysialic acid or polysialic acid derivative having a non-reducing end that is resistant to degradation by exoneuraminidase, exposing the exoneuraminidase treated material to aggregating conditions, and isolating the aggregate.

As noted above, aggregates of the present disclosure also include an aggregate of a polysialic acid derivative formed by the addition of one or more excipients that are capable of facilitating aggregation of the derivative. Of particular interest are substances capable of facilitating aggregation such as aluminum hydroxide.

Accordingly, compositions of particular interest are those enriched for polysialic acid derivative that comprises polymer chains with one or more, and in certain embodiments all, of the following characteristics: (i) a mixture of N-acetyl and de-N-acetyl residues; (ii) resistance to degradation by exoneuraminidase; (iii) non-reducing end with one or more of the de-N-acetyl residues residing therein; (iv) non-reducing end that is itself enriched with de-N-acetyl residues; and (v) terminal non-reducing end that is a de-N-acetyl residue. Compositions of specific interest are those comprising an aggregate of a polysialic acid derivative, including an aggregate of individual or a mixture of different polysialic acid derivatives, and capable of being taken up by cells and expressed on the cell surface better than the corresponding non-aggregated derivative, for example, as gauged by the amount of the polysialic acid derivative present on the cell surface relative to the appropriate control.

Thus compositions of the present disclosure can include isolated polysialic acid derivative produced according to any of the methods described herein. Of specific interest is a composition that includes an isolated polysialic acid derivative that comprises a mixture of N-acetyl and de-N-acetyl residues and that is resistant to degradation by exoneuraminidase, as well as compositions that include a polysialic acid derivative having a non-reducing end with one or more of the de-N-acetyl residues residing therein. As also noted above, other compositions of interest are those in which the polysialic acid derivative has a non-reducing end that is enriched with de-N-acetyl residues.

Additional compositions of interest include the following. One embodiment is a composition in which the polysialic acid derivative comprises a mixture of polysialic acid derivative chains of variable length. In another embodiment, the composition includes polysialic acid derivative that comprises about 10% to 30% de-N-acetyl residues. Other compositions of interest include polysialic acid derivative that is a homopolymer of neuraminic acid and sialic acid. In a specific embodiment, the homopolymer of neuraminic acid and sialic acid is produced by partial re-acetylation of a de-acetylated homopolymer of sialic acid. In these examples, a specific homopolymer of sialic acid of interest is colominic acid (i.e., capsular polysaccharide of obtainable from *N. meningitidis* Serogroup B). In another embodiment, the homopolymer of sialic acid is obtainable from capsular polysaccharide of *N. meningitidis* Serogroup C.

As noted above, conjugates of the polysialic acid derivates are of interest, and thus the production methods disclosed herein may further include the step of conjugating a second molecule. In this aspect, the isolated polysialic acid derivative is conjugated to a second molecule, such as a protecting group, amino acid, peptide, polypeptide, lipid, carbohydrate, nucleic acid, detectable label and the like. An advantage of polysialic acid derivatives that are conjugated to another molecule includes the ability to retain the desired activity, while exploiting properties of the second molecule of the conjugate to impart an additional desired characteristic. For example, the polysialic acid derivatives can be conjugated to a second molecule such as a peptide, polypeptide, lipid, carbohydrate and the like that aids in solubility, storage or other handling properties, cell permeability, half-life, controls release and/or distribution such as by targeting a particular cell (e.g., neurons, leucocytes etc.) or cellular location (e.g., lysosome, endosome, mitochondria etc.), tissue or other bodily location (e.g., blood, neural tissue, particular organs etc.). Other examples include the conjugation of a dye, fluorophore or other detectable labels or reporter molecules for assays, tracking and the like. More specifically, the polysialic acid derivatives described herein can be conjugated to a second molecule such as a peptide, polypeptide, dye, fluorophore, nucleic acid, carbohydrate, lipid and the like (e.g., at either the reducing or non-reducing end), such as the attachment of a lipid moiety, including N-fatty acyl groups such as N-lauroyl, N-oleoyl, fatty amines such as dodecyl amine, oleoyl amine, and the like (e.g., see U.S. Pat. No. 6,638,513)).

Other features of the conjugates can include one where the conjugate reduces toxicity relative to unconjugated polysialic acid derivative. In further embodiments, the conjugate targets a cancer cell relative to unconjugated material. Additional examples include a conjugate the polysialic acid derivative with one or more molecules that complement, potentiate, enhance or can otherwise operate synergistically in connection with the polysialic acid derivative. For instance, the polysialic acid derivative can optionally have attached an anti-cancer drug for delivery to a site of a cancer cell to further facilitate tumor killing or clearance, e.g., an anti-proliferation moiety (e.g., VEGF antagonist, e.g., an anti-VEGF antibody), a toxin (e.g., an anti-cancer toxin, e.g., ricin, *Pseudomonas* exotoxin A, and the like), radionuclide (e.g. 90Y, 131I, 177L, 10B for boron neutron capture, and the like), anti-cancer drugs (e.g. doxorubicin, calicheamicin, maytansinoid DM1, auristatin caupecitabine, 5-fluorouricil, leucovorin, irinotercan, and the like), and/or can optionally be modified to provide for improved pharmacokinetic profile (e.g., by PEGylation, hyperglycosylation, and the like).

Conjugates also include polysialic acid derivatives having one or more re-N-acetylated residues as noted above. For example, a re-N-acetylated residue of specific interest comprises an amino protecting group. Exemplary amino protecting groups include, but are not necessarily limited to, carbamates, amides, N-alkyl and N-aryl amines, imine derivatives, enamine derivatives, N-sulfonyls, and the like. Further exemplary amine protecting groups include, but are not necessarily limited to: acyl types such as formyl, trifluoroacetyl, phthalyl, and p-toluenesulfonyl; aromatic carbamate types such as benzyloxycarbonyl (Cbz) and substituted benzyloxy-carbonyls, 1-(p-biphenyl)-1-methylethoxy-carbonyl, and 9-fluorenylmethyloxycarbonyl (Fmoc); aliphatic carbamate types such as tert-butyloxycarbonyl (tBoc), ethoxycarbonyl, diisopropylmethoxycarbonyl, and allyloxycarbonyl; cyclic alkyl carbamate types such as cyclopentyloxycarbonyl and adamantyloxycarbonyl; alkyl types such as triphenylmethyl and benzyl; trialkylsilane such as trimethylsilane; and thiol containing types such as phenylthiocarbonyl and dithiasuccinoyl. Amine protecting groups and protected amine groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

A particular embodiment of interest is where the second molecule is an immunomodulator. By "immunomodulator" is intended a molecule that directly or indirectly modifies an immune response. A specific class of immunomodulators includes those that stimulate or aid in the stimulation of an immunological response. Examples include antigens and antigen carriers such as a toxin or derivative thereof, including tetanus toxoid. Another embodiment includes a polysialic acid derivative composition that contains one or more immunogenic excipients; in this embodiment, the polysialic acid derivative can be conjugated or not. Other examples include pharmaceutical compositions for use as vaccines, anti-cancer therapeutics that contain a polysialic acid derivative of the present disclosure, as well as use of the derivatives for the generation of antibodies and the like.

Accordingly, the non-conjugated and conjugated polysialic acid derivatives disclosed herein have many uses. For example, the polysialic acid derivatives of the present disclosure find use in generating antigen on the surface of a cell, which can be exploited in various ways for treatment of a subject, including inhibiting the growth of cancerous cells in a subject that bears a de-N-acetylated sialic acid (deNAc SA) epitope. By a "deNAc SA epitope" is intended a molecule that has (i) maximal cross-reactivity with an antibody against polysialic acid in which one or more residues is a de-N-acetyl neuraminic acid residue, and (ii) has minimal to no cross-reactivity with an antibody against normal polysialic acid, especially as presented on a non-cancerous mammalian, e.g., human, cell surface. Thus the minimal deNAc SA epitope is a disaccharide of sialic acid residues in which one or both residues contain a free amine at the C5 amino position; when one of the two residues is de-N-acetylated, the second residue contains an N-acetyl group (but, in some embodiments, not an N-propionyl group). The disaccharide unit defining this minimal epitope may be at the reducing end, the non-reducing end, or within a polymer of sialic acid residues (e.g., within a polysaccharide). A deNAc SA epitope of specific interest is a disaccharide of sialic acid residues in which one residue contains a free amine at the C5 amino position (i.e., a de-N-acetyl sialic acid residue), the second residue contains an N-acetyl group (i.e., a N-acetyl sialic acid residue), and the de-N-acetyl sialic acid residue of the disaccharide is at the non-reducing end.

De-N-acetylated residues in the context of PSA containing N-acylated residues are immunogenic and elicit antibodies that are reactive with the deNAc SA epitope, but are minimally reactive or not detectably reactive with human PSA antigens. For example, the de-N-acetylated NmB polysaccharide epitope was identified using a murine anti-N-propionyl *Neisseria meningitidis* group B (N—Pr NmB) polysaccharide mAb (monoclonal antibodies), SEAM 3, described in Granoff et al., 1998, J Immunol 160:5028 (anti-N—Pr NmB PS mAbs); U.S. Pat. No. 6,048,527 (anti-NmB antibodies); and U.S. Pat. No. 6,350,449 (anti-NmB antibodies).

As noted above, another embodiment is a composition comprising an aggregate of a polysialic acid derivative of the present disclosure. This includes compositions that include an aggregate complex of a polysialic acid derivative having a particle molecular weight that is 10× or more of the molecular weight of an individual polysialic acid derivative in the aggregated monomer complex. This includes a composition comprising an aggregate having a particle with a molecular weight of greater than about 50,000, to greater than about 250,000 Daltons, to greater than 500,000 Daltons, to greater than 750,000 Daltons, to greater than 1,000,000 Daltons up to a particle having a uniform particle size that is readily visible under a standard low magnification light microscope (e.g., 40× magnification). Of specific interest is a composition comprising an aggregate can be a molecular or microscopic particle. This includes a composition comprising a microscopic particle having a particle diameter of about 1 um to 20 µm. This also includes a composition comprising a microscopic particle having a particle diameter that is about or smaller than the diameter of a cancer cell. Thus, the aggregate compositions contain an aggregate of polysialic acid derivative capable of being taken up and internalized by cells better than non-aggregated derivative relative to each other, a control, and/or both, including as measured by inhibition of cell growth following exposure to anti-de-N-acetyl sialic acid antigen antibody. The aggregate compositions can be formulated as described in more detail below, including as liquids, powders and the like.

In the methods of treatment of cancer, administering of polysialic acid derivative or an immunogenic composition that includes such derivative facilitates a reduction in viability of cancerous cells exposed to the polysialic acid derivative. Advantages of these methods are that the polysialic acid derivatives can directly or indirectly facilitate delivery of antibodies that are cytotoxic to cancer cells containing a deNAc SA epitope, for example, by increasing the amount of the deNAc SA epitope on the cell surface. This in turn can be a target for the subject's own immune system and/or an antibody-based therapy such as SEAM 3. Another advantage is that the cytotoxicity of the polysialic acid derivative of the present disclosure can be dose dependent, and thus adjustable. Specific examples of cancerous cells amenable to treatment include melanoma, leukemia, or neuroblastoma cells.

In a related embodiment, the subject being treated possesses a deNAc SA epitope. The epitope can be present inside a cell or expressed on the cell surface, such as a cancer cell. This aspect can be beneficial in that cells expressing or presenting a deNAc SA epitope can be more amenable to treatment with a polysialic acid derivative of the present disclosure. For example, the cells can be contacted with polysialic acid derivative to increase de-N-acetyl sialic acid antigen on their surface, making them "visible" to the host immune system or immunotherapy. Of course the derivatives can be administered to a subject that is naïve with respect to a de-N-acetyl sialic acid antigen, for example, where therapy is initiated at a point where presence of the epitope is not detectable, and thus is not intended to be limiting. It is also possible to initiate polysialic acid derivative therapy prior to the first sign of disease symptoms, at the first sign of possible disease, or prior to or after diagnosis of a primary cancer and/or metastases of a cancer having a detectable deNAc SA epitope (e.g., a ganglioside or other glycoconjugate that is at least partially de-N-acetylated).

Another embodiment involves screening for the deNAc SA epitope in combination with polysialic acid derivative therapy. In this method, cells from a subject undergoing treatment, or being tested for susceptibility to treatment, with polysialic acid derivative are screened for the presence of a deNAc SA epitope. This can be accomplished using an antibody or antibody fragment that binds to the epitope (e.g., an antibody specific for an polysialic acid derivative of the present disclosure, or a SEAM 3 monoclonal antibody (ATCC Deposit No. HB-12170)). As with cancer therapies in general, an advantage of this approach is the ability to select individuals with a cellular proliferation disorder or stage of disorder likely to be more responsive to polysialic acid derivative therapy compared to those that are not. Another advantage of targeting a subject with cells bearing a deNAc SA epitope is that progress over the treatment course can be monitored, and therapy, including dosing regimens, amounts and the like can be adjusted accordingly.

Routes of administration (path by which the polysialic acid derivative is brought into contact with the body) may vary, where representative routes of administration for the polysialic acid derivative are described in greater detail below. In certain embodiments, the polysialic acid derivative is administered by infusion or by local injection. For example, where the tumor is a solid tumor, the polysialic acid derivative can be administered to a site adjacent or in the tumor bed. The polysialic acid derivative also can be administered prior, at the time of, or after other therapeutic interventions, such as surgical intervention to remove cancerous cells. The polysialic acid derivative can also be administered as part of a combination therapy, in which at least one of an immunotherapy, a cancer chemotherapy or a radiation therapy is administered to the subject (as described in greater detail below).

In general the methods disclosed herein can involve administration of an effective amount of a polysialic acid derivative to a subject in need thereof. In particular, polysialic acid derivatives of specific interest are those that increase the amount of intact antigen on the surface of a cancer cell in a host when the compounds are administered in an effective amount according to the present disclosure. The amount administered varies depending upon the goal of the administration, the health and physical condition of the individual to be treated, age, the taxonomic group of individual to be treated (e.g., human, non-human primate, primate, etc.), the degree of resolution desired, the formulation of the polysialic acid derivative composition, the treating clinician's assessment of the medical situation, and other relevant factors. It is expected that the amount will fall in a relatively broad range that can be determined through routine trials.

For example, the amount of polysialic acid derivative employed to increase the amount of intact antigen on the surface of a cancer cell in a host is not more than about the amount that could otherwise be irreversibly toxic to the subject (i.e., maximum tolerated dose). In other cases the amount is around or even well below the toxic threshold, but still in a desired concentration range, or even as low as threshold dose. Thus in embodiments involving use of the polysialic acid derivatives to elicit an immunoprotective and/or immunotherapeutic immune response against a cancer cell and/or a bacterial infection (e.g., *Neisseria* and/or *E. coli* K1), the amount of polysialic acid derivative administered is an amount effective to elicit an immunoprotective or immunotherapeutic immune response in the subject against a cancer cell and/or bacterial infection, where the amount to effect such immune response may vary according to a variety of subject-specific factors, such as those exemplified above. Where the polysialic acid derivative is administered to effect an anti-deNAc SA antibody response, the antibodies elicited can provide for specific binding of deNAc SA epitopes on a target antigen with little or no detectable binding to host-derived polysialic acid.

Individual doses are typically not less than an amount required to produce a measurable effect on the subject, and may be determined based on the pharmacokinetics and pharmacology for absorption, distribution, metabolism, and excretion ("ADME") of the polysialic acid derivative, and thus based on the disposition of the composition within the subject. This includes consideration of the route of administration as well as dosage amount, which can be adjusted for topical (applied directly where action is desired for mainly a local effect), enteral (applied via digestive tract for systemic or local effects when retained in part of the digestive tract), or parenteral (applied by routes other than the digestive tract for systemic or local effects) applications. For instance, administration of the polysialic acid derivative is typically via injection and often intravenous, intramuscular, intratumoral, or a combination thereof, so as to avoid hydrolysis in the stomach.

Disposition of the polysialic acid derivative and its corresponding biological activity within a subject can be gauged against the fraction of polysialic acid derivative present at a target of interest. For example, a polysialic acid derivative once administered can accumulate as a component of a glycoconjugate or other biological target that concentrates the material in a target cells and tissue, such as a cancer cell and cancerous tissue. Thus dosing regimens in which the polysialic acid derivative is administered so as to accumulate in a target of interest over time can be part of a strategy to allow for lower individual doses. This can also mean that the dose of polysialic acid derivative that are cleared more slowly in vivo can be lowered relative to the concentrations calculated from in vitro assays (e.g., effective amount in vitro approximates mM concentration, versus less than mM concentrations in vivo).

As an example, the effective amount of a dose or dosing regimen can be gauged from the IC50 of a given polysialic acid derivative for binding of SEAM 3 to the cell surface antigen (i.e., SEAM 3 binding and inhibition of cell growth proportional to the polysialic acid antigen present on the cell surface). By "IC50" is intended the concentration of a drug required for 50% inhibition in vitro. Alternatively, the effective amount can be gauged from the EC50 of a given polysialic acid derivative. By "EC50" is intended the plasma concentration required for obtaining 50% of a maximum effect in vivo.

In general, with respect to the polysialic acid derivatives disclosed herein, an effective amount is usually not more than 200× the calculated IC50. Typically, the amount of a polysialic acid derivative that is administered is less than about 200×, less than about 150×, less then about 100× and many embodiments less than about 75×, less than about 60×, 50×, 45×, 40×, 35×, 30×, 25×, 20×, 15×, 10× and even less than about 8× or 2× than the calculated IC50. In one embodiment, the effective amount is about 1× to 50× of the calculated IC50, and sometimes about 2× to 40×, about 3× to 30× or about 4× to 20× of the calculated IC50. In other embodiments, the effective amount is the same as the calculated IC50, and in certain embodiments the effective amount is an amount that is more than the calculated IC50.

In other embodiments, an effect amount is not more than 100× the calculated EC50. For instance, the amount of polysialic acid derivative that is administered is less than about 100×, less than about 50×, less than about 40×, 35×, 30×, or 25× and many embodiments less than about 20×, less than about 15× and even less than about 10×, 9×, 9×, 7×, 6×, 5×, 4×, 3×, 2× or 1× than the calculated EC50. In one embodiment, the effective amount is about 1× to 30× of the calculated EC50, and sometimes about 1× to 20×, or about 1× to 10× of the calculated EC50. In other embodiments, the effective amount is the same as the calculated EC50, and in certain embodiments the effective amount is an amount that is more than the calculated EC50.

Effective amounts can readily be determined empirically from assays, from safety and escalation and dose range trials, individual clinician-patient relationships, as well as in vitro and in vivo assays such as those described herein and illustrated in the Experimental section, below.

The polysialic acid derivative can be administered to the subject in combination with one or more other therapies. For example, a therapy or treatment other than administration of polysialic acid derivative composition can be administered anywhere from simultaneously to up to 5 hours or more, e.g., 10 hours, 15 hours, 20 hours or more, prior to or after the polysialic acid derivative. In certain embodiments, the polysialic acid derivative and other therapeutic intervention are administered or applied sequentially, e.g., where the polysialic acid derivative is administered before or after another therapeutic treatment. In yet other embodiments, the polysialic acid derivative and other therapy are administered simultaneously, e.g., where the polysialic acid derivative and a second therapy are administered at the same time, e.g., when the second therapy is a drug it can be administered along with the polysialic acid derivative as two separate formulations or combined into a single composition that is administered to the subject. Regardless of whether administered sequentially or simultaneously, as illustrated above, the treatments are considered to be administered together or in combination for purposes of the present disclosure.

Polysialic acid derivatives which find use in the present methods and may be present in the compositions include, but are not limited to those with appropriate specificity and antigenicity so as to elicit an antibody that affects the growth of a cancer cell in a subject. As such, polysialic acid derivatives with such specificity aid in achieving the intended end result of modifying cellular proliferation of a cancer cell while minimizing unwanted side effects and toxicity. Put differently, the polysialic acid derivatives employed need not be identical to those disclosed in the Examples section below, so long as the polysialic acid derivatives are able to elicit an immune response against and/or inhibit growth of the target cell. Thus, one of skill will recognize that a number of polysialic acid derivatives (described in more detail below), can be made without substantially affecting the activity of the polysialic acid derivatives. This includes compositions of pharmaceutically acceptable salts (e.g., hydrochloride, sulfate salts), solvates (e.g., mixed ionic salts, water, organics), hydrates (e.g., water). For the polysialic acid compositions, they may be provided in prodrug forms thereof (e.g., esters, acetyl forms), anomers (e.g., α/β mutarotation), tautomers (e.g., keto-enol tautomerism) and stereoisomers (e.g., β-D-isomer). It also includes various polysialic acid derivative compositions that contain one or more immunogenic excipients, such as an adjuvant, carrier and the like, as well as non-immunogenic polysialic acid derivative compositions that are essentially devoid of adjuvant or other immunogenic excipients.

The present disclosure includes prodrugs of the polysialic acid derivatives disclosed herein. Such prodrugs are in general functional derivatives of the compounds that are readily convertible in vivo into the required compounds. Thus, in the methods disclosed herein, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein suitable for the present disclosure. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

Whether or not a given polysialic acid derivative or conjugate thereof is suitable for use according to the present disclosure can be readily determined using various assays, such as those employed in the Experimental section, below. Generally, an polysialic acid derivative is suitable for use in the methods disclosed herein if it elicits an immune response in a subject that facilitates inhibition of growth of a target cell by at least about 2 to 10-fold, usually by at least about 50-fold and sometimes by at least about 100-fold to 200-fold relative to a normal control cell, as determined using the cell based assays, such as those described in the Experimental section, below. In certain embodiments, an polysialic acid derivative is one that facilitates (e.g., through eliciting an anti-polysialic acid derivative antibody and/or through increasing deNAc SA antigen on a cancer cell) reduction in viability of a target cell (such as a particular cancer cell or cell line), arrests growth and/or induces apoptosis of a target cell, and/or induces cell death, as observed in the cell-based assays described in the Experimental section below when generating an immune response against the cell (e.g., cytotoxicity from enhancing deNAc SA epitope of a cancer cell, and making it more susceptible to killing by a secondary antibody such as described herein or SEAM 3, and/or one or more aspects of the immune system).

It will also be appreciated that once isolated, some of the smaller polysialic acid derivatives can be characterized and made by other techniques, including standard chemical synthesis. For instance, such polysialic acid derivatives can be prepared conventionally by techniques known to one of skill in the art, including as described herein and in the Examples. Representative references describing various synthesis approaches, intermediates, precursors, analysis, as well as the synthesis and preparation of conjugates, diagnostics and the like, include U.S. Pat. Nos. 4,315,074; 4,395,399; 4,719,289; 4,806,473; 4,874,813; 4,925,796; 5,180,674; 5,246,840; 5,262,312; 5,278,299; 5,288,637; 5,369,017; 5,677,285; 5,780,603; 5,876,715; 6,040,433; 6,133,239; 6,242,583; 6,271,345; 6,323,339; 6,406,894; 6,476,191; 6,538,117; 6,797,522; 6,927,042; 6,953,850; 7,067,623; and 7,129,333; the disclosures of which are herein incorporated by reference. See also, the following references: "Solid Support Oligosaccharide Synthesis and Combinatorial Carbohydrate Libraries," Peter H. Seeberger Ed, Wiley-Interscience, John Wiley & Sons, Inc, NY, 2001; Plante et al., Science (2001) 291 (5508):1523; Marcaurelle et al., Glycobiology, 2002, 12(6): 69R-77R; Sears et al., Science (2001) 291:2344-2350; Bertozzi et al., Chemical Glycobiology (2001) Science 291: 2357-2364; MacCoss et al., Org. Biomol. Chem., 2003, 1:2029; and Liang et al. Science (1996) 274(5292):1520; Kayser et al J. Biol. Chem. 1992 267:16934, Keppler et al Glycobiology 2001, 11:11R; Luchansky et al Meth. Enzymol. 2003, 362:249; Oetke et al Eur. J. Biochem. 2001, 268: 4553; and WO/1997/045436; the disclosures of which are herein incorporated by reference.

Pharmaceutically acceptable salts of the polysialic acid derivatives can be prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanot, 2-diethylaminoethanol, lysine, arginine, histidine, and the like. The reaction is conducted in water, alone or in combination with an inert, water-miscible organic solvent, at a temperature of from about 0° C. to about 100° C., and can be at room temperature. The molar ratio of compounds of general structure I to base used are chosen to provide the ratio desired for any particular salts. For preparing, for example, the ammonium salts of the free acid starting material, the starting material can be treated with approximately one equivalent of pharmaceutically acceptable base to yield a neutral salt. When calcium salts are prepared, approximately one-half a molar equivalent of base is used to yield a neutral salt, while for aluminum salts, approximately one-third a molar equivalent of base will be used.

Pharmaceutical Formulations

Also provided are pharmaceutical compositions containing the polysialic acid derivatives employed in the methods of treatment disclosed herein. The term "polysialic acid derivative composition" is used herein as a matter of convenience to refer generically to compositions comprising a polysialic acid derivative of the present disclosure, including conjugated polysialic acid derivatives, or both. Compositions useful for facilitating modification of the growth of cancer cells are particularly contemplated.

The polysialic acid derivative compositions, e.g., in the form of a pharmaceutically acceptable salt, can be formulated for oral, topical or parenteral administration, as described above. In certain embodiments, e.g., where an polysialic acid derivative is administered as a liquid injectable (such as in those embodiments where they are administered intravenously or directly into a tissue), an polysialic acid derivative formulation is provided as a ready-to-use dosage form, or as a reconstitutable storage-stable powder or liquid composed of pharmaceutically acceptable carriers and excipients.

Methods for producing and formulating polysialic acid derivatives suitable for administration to a subject (e.g., a human subject) are well known in the art. For example, polysialic acid derivatives can be provided in a pharmaceutical composition comprising an effective amount of a polysialic acid derivative and a pharmaceutical excipients (e.g., saline). The pharmaceutical composition may optionally include other additives (e.g., buffers, stabilizers, preservatives, and the like). An effective amount of polysialic acid derivative can be an amount effective to provide for enhancing a de-N-acetyl sialic acid antigen on a cancer cell and/or eliciting an immune response against such de-N-acetyl sialic acid antigen-enhanced cancer cells. In other embodiments, an effective amount of polysialic acid derivative is an amount that, particularly when administered with an adjuvant, provides for an anti-polysialic acid derivative immune response so as to provide for an anti-bacterial or anti-cancer response in a subject for a desired period. A therapeutic goal (e.g., reduction in bacterial or tumor load, or immunization) can be accomplished by single or multiple doses under varying dosing regimen.

By way of illustration, the polysialic acid derivative compositions can be admixed with conventional pharmaceutically acceptable carriers and excipients (i.e., vehicles) and used in the form of aqueous solutions, tablets, capsules, elixirs, suspensions, syrups, wafers, patches and the like, but usually the polysialic acid derivative will be provided as an injectable. Such pharmaceutical compositions contain, in certain embodiments, from about 0.1 to about 90% by weight of the active compound, and more generally from about 1 to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in formulations include croscarmellose, microcrystalline cellulose, corn starch, sodium starch glycolate and alginic acid. Preservatives and the like may also be included.

The polysialic acid derivative compositions can be provided in a pharmaceutically acceptable excipient, which can be a solution such as an aqueous solution, often a saline solution, or they can be provided in powder form. The polysialic acid derivative compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of polysialic acid derivative in the pharmaceutical formulations can vary from less than about 0.1%, usually at or at least about 2% to as much as 20% to 50% or more by weight, and will be selected primarily by fluid volumes, viscosities, etc., in accordance with the particular mode of administration selected and the patient's needs. The resulting compositions may be in the form of a solution, suspension, tablet, pill, capsule, powder, gel, cream, lotion, ointment, aerosol or the like.

In general, administration of a polysialic acid derivative composition is accomplished by any suitable route, including administration of the composition orally, bucally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 18th ed., Mack Publishing Company, NY (1995).

It is recognized that when administered orally, polysialic acid derivatives should be protected from digestion. This is typically accomplished either by complexing the polysialic acid derivative with a composition to render it resistant to acidic and enzymatic hydrolysis or by packaging in an appropriately resistant carrier such as a liposome. Means of protecting a compound of interest from digestion are well known in the art.

In order to enhance serum half-life, polysialic acid derivative preparations that are injected may also be encapsulated, introduced into the lumen of liposomes, prepared as a colloid, or other conventional techniques may be employed which provide an extended serum half-life. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms for release and administration of the polysialic acid derivative compositions as a mixture or in serial fashion.

A liquid composition will generally be composed of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

The compounds of the present disclosure and their pharmaceutically acceptable salts that are active when given parenterally can be formulated for intramuscular, intrathecal, or intravenous administration. A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetracetic acid, and an anti-oxidant, for example, sodium metabisulphite may be included in the formulation. Alternatively, the solution can be freeze dried and then reconstituted with a suitable solvent just prior to administration.

The compounds of the present disclosure and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of the present disclosure and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. No. 5,023,252, herein incorporated by reference in its entirety. Such patches may be constructed for continuous, pulsatile, or on demand delivery of pharmaceutical agents.

In certain embodiments of interest, the polysialic acid derivative composition is administered as a single pharmaceutical formulation. It also may be administered with an effective amount of another agent that includes other suitable compounds and carriers, and also may be used in combination with other active agents. The present disclosure, therefore, also includes pharmaceutical compositions comprising pharmaceutically acceptable excipients. The pharmaceutically acceptable excipients include, for example, any suitable vehicles, adjuvants, carriers or diluents, and are readily available to the public. The pharmaceutical compositions of the present disclosure may further contain other active agents as are well known in the art.

One skilled in the art will appreciate that a variety of suitable methods of administering a formulation of the present disclosure to a subject or host, e.g., patient, in need thereof, are available, and, although more than one route can be used to administer a particular formulation, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting.

The formulations of the present disclosure can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more polysialic acid derivatives. Similarly, unit dosage forms for injection or intravenous administration may comprise the polysialic acid derivative(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host.

Those of skill in the art will readily appreciate that dose levels can vary as a function of the specific compound, the nature of the delivery vehicle, and the like. Suitable dosages for a given compound are readily determinable by those of skill in the art by a variety of means.

Optionally, the pharmaceutical composition may contain other pharmaceutically acceptable components, such a buffers, surfactants, antioxidants, viscosity modifying agents, preservatives and the like. Each of these components is well-known in the art. See, e.g., U.S. Pat. No. 5,985,310, the disclosure of which is herein incorporated by reference.

Other components suitable for use in the formulations can be found in Remington's Pharmaceutical Sciences, Mack Pub. Co., 18th edition (June 1995). In an embodiment, the aqueous cyclodextrin solution further comprise dextrose, e.g., about 5% dextrose.

UTILITY

Exemplary Applications & Related Embodiments

The compounds and methods disclosed herein find use in a variety of applications, where in many applications the methods are modulating at least one cellular function, such as increased expression of the antigen/polysialic acid derivative on the surface of a cell, or are modulating an immune response, such in immunization of a subject to elicit antibodies that bind a deNAc SA epitope such as may be borne on a cancerous or bacterial cell (e.g., *Neisseria* or *E. coli* K1).

In the context of modulating at least one cellular function as well as in the context of eliciting anti-cancer cell antibodies, the methods and compositions disclosed herein find use in treating cellular proliferation disorders. Thus, a representative therapeutic application is the treatment of cellular proliferative disease conditions in general, e.g., cancers and related conditions characterized by abnormal cellular proliferation concomitant. Such disease conditions include cancer/neoplastic diseases and other diseases characterized by the presence of unwanted cellular proliferation, e.g., hyperplasias, and the like. As indicated, cellular proliferation disorders include those that abnormally express the deNAc SA epitope, which can be determined using anti-deNAc SA antibody or derivatives thereof.

In the context of modulating an immune response to elicit anti-bacterial antibodies, the methods and compositions disclosed herein find use in eliciting immunoprotective and/or immunotherapeutic immune response against bacteria that bear a deNAc SA, as in capsular polysaccharide of a deNAc SA epitope-bearing *Neisseria* (e.g., *N. meningitidis*, e.g., *N. meningitidis* Group B) or *E. coli* K1. In this context the polysialic acid derivative is administered in a form that provides for eliciting an antibody response, e.g., administered in an immunogenic amount, administered in conjunction with an adjuvant, and/or administered as a conjugate with a carrier peptide or protein.

Of particular interest are antibodies that have antigen binding specificity for the polysialic acid derivatives described herein or the antigen binding specificity of mAb SEAM 3. Of particular interest are antibodies that specifically bind a deNAc SA epitope with little or no detectable binding to human polysialic acid. Examples of such antibodies include those having a light chain polypeptide comprising CDR1, CDR2 and CDR3 of the variable region of a SEAM 3 light chain polypeptide and a heavy chain polypeptide comprising CDR1, CDR2, and CDR3 of the variable region of the heavy chain polypeptide. Such antibodies include chimeric antibodies, humanized antibodies, and the like.

By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease, e.g., so as to decrease tumor load, which decrease can include elimination of detectable cancerous cells; and/or (iii) relief, that is, causing the regression of clinical symptoms.

A variety of hosts are treatable according to the methods disclosed herein. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans. In the context of anti-bacterial vaccination methods, of interest are hosts that are susceptible to disease that can be caused by infection by a deNAc SA epitope-bearing bacteria, such as *Neisseria* (e.g., *N. meningitidis*, e.g., *N. meningitidis* Group B) or *E. coli* K1.

The methods disclosed herein can find use in, among other applications, the treatment of cellular proliferative disease conditions in which an effective amount of the polysialic acid derivative composition is administered to the subject in need thereof. Treatment is used broadly as defined above, e.g., to include prevention or at least an amelioration in one or more of the symptoms of the disease, as well as a complete cessation thereof, as well as a reversal and/or complete removal of the disease condition, e.g., cure.

Compositions of the present disclosure can comprise a therapeutically effective amount of a polysialic acid derivative composition, as well as any other compatible components, as needed. By "therapeutically effective amount" is meant that the administration of that amount to an individual, either in a single dose, as part of a series of the same or different polysialic acid derivative compositions, is effective to enhance de-N-acetyl sialic acid antigen of a cancer cell and/or elicit an anti-de-N-acetyl sialic acid antigen antibody response, particularly one effective to inhibit the growth of a cancerous cell in a subject. Such therapeutically effective amount of polysialic acid derivative composition and/or anti-polysialic acid derivative antibodies includes cooperative and/or synergistic inhibition of cell growth in conjunction with one or more other therapies (e.g., immunotherapy, chemotherapy, radiation therapy etc.). As noted below, the therapeutically effective amount can be adjusted in connection with dosing regimen and diagnostic analysis of the subject's condition (e.g., monitoring for the present or absence of a cell surface epitopes using a SEAM 3 antibody or antibody specific for an polysialic acid derivative) and the like.

As discussed above, the amount administered to an animal, particularly a human, in the context of the methods disclosed herein should be sufficient to affect a prophylactic or therapeutic response in the animal over a reasonable time frame, and varies depending upon the goal of the administration, the health and physical condition of the individual to be treated, age, the taxonomic group of individual to be treated (e.g., human, non-human primate, primate, etc.), the degree of resolution desired, the formulation of the polysialic acid derivative composition, the treating clinician's assessment of the medical situation, and other relevant factors. One skilled in the art will also recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Thus it is expected that the amount will fall in a relatively broad range, but can nevertheless be routinely determined through various features of the subject such as note above.

The polysialic acid derivative compositions (which may be optionally conjugated) can be used alone or in combination with other therapies (e.g., antibacterial agents, other anti-cancer agents, and the like). When used in combination, the various compositions can be provided in the same or different formulations. Where administered in different formulations, the compositions can be administered at the same or different dosage regimen (e.g., by the same or different routes, at the same or different time (e.g., on the same or different days)), and the like). In general, administration of the polysialic acid derivative composition can be performed serially, at the same time, or as a mixture, as described in more detail below. Administration can be serial, with repeated doses of polysialic acid derivative composition. Exemplary dosage regimens are described below in more detail.

The compositions also can be administered to subject that is at risk of disease to prevent or at least partially arrest the development of disease and its complications. A subject is "at risk" where, for example, the subject exhibits one or more signs or symptoms of disease, but which are insufficient for certain diagnosis and/or who has been or may be exposed to conditions that increase the probability of disease. For example, the polysialic acid derivative compositions can also be administered to subject that is at risk of a cancer, has a cancer, or is at risk of metastasis of a cancer having a cell surface deNAc SA epitope (e.g., a cell surface ganglioside that is at least partially de-N-acetylated).

Polysialic acid derivative compositions can be administered serially or overlapping to maintain a therapeutically effective amount as believed needed for the desired end result (e.g., enhancing de-N-acetyl sialic acid antigen of a cancer cell, inhibition of cancerous cell growth through antibody binding and/or production). Typically, each dose and the timing of its administration is generally provided in an amount that is tolerated by the health of the subject, and can be based on IC50 and/or the EC50 as noted above. Thus amounts can vary widely for a given treatment.

Therapeutic response to the dose or treatment regime may be determined by known methods (e.g. by assessing an increase in de-N-acetyl sialic acid antigen presentation by a cell; by obtaining serum from the individual before and after the initial immunization, and demonstrating a change in anti-de-N-acetyl sialic acid antigen antibodies; or the like). The dosing may include washout periods to allow for clearance of the initial material, followed by halting or resumption of treatment. Thus dosage strategies can be modified accordingly.

In one embodiment, the polysialic acid derivative composition is administered at least once, usually at least twice, and in some embodiments more than twice. In a related embodiment, the polysialic acid derivative composition is administered in combination along a dosing schedule and course in conjunction with chemotherapy. In another embodiment, the polysialic acid derivative composition is administered in combination with a dosing schedule and course in conjunction with immunotherapy. In yet another embodiment, the polysialic acid derivative composition is administered in combination with a dosing schedule and course in conjunction with radiation therapy. Each individual dose of the polysialic acid derivative composition may be administered before, during or after the complementary therapy such as immunotherapy, chemotherapy, or radiation therapy. As can be appreciated, combination therapies using a polysialic acid derivative composition may be adjusted for a given end need.

Exemplary Cancer Therapies

The polysialic acid derivative compositions find use in a variety of cancer therapies (including cancer prevention and post-diagnosis cancer therapy) in a mammalian subject, particularly in a human. Subjects having, suspected of having or at risk of developing a tumor are contemplated for therapy and diagnosis described herein. Samples obtained from such subject are likewise suitable for use in the methods of the present disclosure.

More particularly, polysialic acid derivative compositions described herein can be administered to a subject (e.g. a human patient) to, for example, facilitate an increase in de-N-acetyl sialic acid antigen of a cancer cell, e.g., an increase in total de-N-acetyl sialic acid antigen, which may be present on a cell surface, e.g., as during cell division. This can be accomplished by administering a polysialic acid derivative to the subject as described herein so as to provide for an increase in de-N-acetyl sialic acid antigen in a cancer cell as compared to prior to such administering.

In the context of cancer therapies, as well as other therapies in which it is desirable to increase de-N-acetyl sialic acid antigen of a cell, it may be desirable to avoid administration of polysialic acid derivative in a manner that would elicit anti-polysialic acid derivative antibodies. Thus, in some embodiments it may be desirable to administer polysialic acid derivative in a compositions that does not contain an adjuvant and/or to administer the polysialic acid derivative non-immunogenic form.

The increased de-N-acetyl sialic acid antigen of the cell can be exploited in therapy using anti-de-N-acetyl sialic acid antigen antibody that is cytotoxic to the cell (e.g., as a result of properties of the antibody per se (e.g., as in induction of apoptosis of the cell by antibody binding) and/or by delivery of a cytotoxin conjugated to the antibody. For example, by increasing de-N-acetyl sialic acid antigen of the cell, the cell can be enhanced for anti-de-N-acetyl sialic acid antigen antibody binding (e.g., SEAM 3 binding), thus enhancing antibody-mediated cancer cell therapy (e.g., as a result of increased delivery of cytotoxic antibodies to the cancer cell. Such therapies can be useful in cancer therapy to, for example, reduce tumor size, reduce tumor load, and/or improve the clinical outcome in patients.

The polysialic acid derivative compositions thus may be advantageously used in an anti-cancer therapy, particularly where the cancerous cells present a deNAc SA epitope on an extracellularly accessible cell surface (e.g., a deNAc SA epitope on an at least partially de-N-acetylated ganglioside or other glycoconjugate). In one embodiment, the cancer is one that presents a SEAM 3-reactive antigen. Cancers that present a SEAM 3-reactive antigen can be identified by methods known in the art. Exemplary methods of detection and diagnosis are described below.

In some embodiments, the anti-cancer therapy can be particularly directed to dividing (replicating, proliferating) cancerous cells. As shown in the Examples below, antibody raised against polysialic acid derivatives were particularly effective against cancerous cells bearing the epitope specifically bound by SEAM 3 antibody. Also, the level of extracellularly accessible antigen bound by SEAM 3 is increased during cell division as compared to non-dividing cells, and binding of SEAM3 drives the cell toward anaphase (into pre-GO). Since most cancers are more rapidly dividing than normal cells of the same type, cells that possess a SEAM 3-reactive antigen are attractive for polysialic acid derivative-based cancer therapy. Also, the antibodies identified herein to the polysialic acid derivatives of the present disclosure can exhibit enhanced binding as compared to SEAM 3, and thus may have clinical benefits that may be greater than SEAM 3.

Thus the present disclosure particularly provides anti-cancer therapy directed toward cancerous cells involving administration of polysialic acid derivative compositions having an epitope recognized by a SEAM 3 mAb. Cancers particularly amenable to polysialic acid derivative therapy can be identified by examining markers of cellular proliferation (e.g., Ki-67 antigen) and/or by examining the presence/accessibility of the deNAc SA epitope bound by SEAM 3 in dividing cells or by the antibodies specific for the polysialic acid derivatives of the present disclosure (e.g., as in an in vitro assay).

Cancers having a cell surface-accessible deNAc SA epitope include those having an at least partially de-N-acetylated ganglioside and/or a protein having a sialic acid modification that contains a deNAc SA epitope. Cancers having de-N-acetylated gangliosides have been described.

The presence of de-N-acetyl sialic acid residues in normal human tissue appears to be transient and very low abundance, being found only in a few blood vessels, infiltrating mononuclear cells in the skin and colon, and at moderate levels in skin melanocytes. It is prevalent only in abnormal cells, such as melanomas, leukemias and lymphomas. Since expression of high levels of deNAc SA antigens (e.g., de-N-acetyl gangliosides) occurs predominantly in cancer cells, treatment with polysialic acid derivative compositions can be used to induce cytotoxicity, and can block tumor growth. In addition, polysialic acid derivative compositions can be used therapeutically to effect/prevent adhesion and invasion of cancer cells in other tissues. For example, expression of SEAM 3-reactive antigens can be detected in very low levels in normal tissue includes epithelial cells of skin, bladder (urothelial), kidney (tubular epithelial), stomach glandular epithelium, lung macrophages, peripheral nerve endothelium and weak staining of skeletal muscle. In contrast, SEAM 3-reactive antigen can be detected at significantly higher levels in tumors, in addition to those above, such as nephroblastoma, and adenocarcinomas of the stomach, uterus, and ovaries.

Exemplary cancers presenting a deNAc SA epitope include cancer cells presenting a de-N-acetyl ganglioside containing a de-N-acetyl sialic acid residue (e.g. GM2alpha, GM1alpha, GD1beta, GM1b, GD1c, GD1alpha, GM3, GM2, GM1, GD13, GT13, GT1halpha, GD3, GD2, GD1b, GT1b, GQ1b, Gomega1halpha, GT3, GT2, GT1c, GQ1c, and GP1c). Of particular interest are gangliosides that contain two or more sialic acid residues linked by alpha 2-8 glycosidic bonds (e.g., GD1c, GT13, GD3, GD1b, GT1b, GQ1b, Gomega1halpha, GT3, GT1c, GQ1c, and GP1c) in which at least one residue is de-N-acetylated. In some embodiments, the ganglioside that contains two or more sialic acid residues linked by alpha 2-8 glycosidic bonds is a ganglioside other than GD3 and/or other than GM3. In some embodiments, the target of the cancer is a deNAc SA epitope other than one present on a de-N-acetylated ganglioside (e.g., a de-N-acetylated residue of a sialic acid-modified protein).

In one embodiment polysialic acid derivative compositions can be used to treat cancers that present a SEAM 3 reactive antigen on a cell surface, including cancers that exhibit an extracellularly accessible SEAM 3-reactive antigen during cell division.

In another embodiment polysialic acid derivative compositions can be used to treat cancers that present deNAc SA epitope on a cell surface, including cancers that exhibit an extracellularly accessible reactive antigen during cell rest.

It should be noted that while deNAc SA epitopes and/or SEAM 3-reactive antigens may be expressed at higher levels on a cancer cell compared to a non-cancerous cell, this is not a limitation of the therapies disclosed herein. For example, where the cancer involves a cell type that can be replenished (e.g., B cell, T cell, or other cell of hematopoietic origin, as in leukemias and lymphomas), inhibition of normal cell growth can be acceptable since damage to a subject by depleting such cells can be treated (e.g., with drugs to stimulate repopulation of normal cells, e.g., GM-CSF, EPO, and the like).

The methods relating to cancer contemplated herein include, for example, use of polysialic acid derivative therapy alone or in combination with deNAc SA antigens as a anticancer vaccine or therapy, as well as use of antibodies generated using deNAc SA antigens in anti-cancer vaccines (e.g., by passive immunization) or therapies. The methods are useful in the context of treating or preventing a wide variety of cancers, including carcinomas, sarcomas, leukemias, and lymphomas.

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be amenable to therapy by a method disclosed herein include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated according to the treatment methods disclosed herein include, but are not limited to, B-cell lymphomas (e.g., Burkitt's lymphoma); Hodgkin's lymphoma; non-Hodgkin's lymphoma, and the like.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Further exemplary cancers that can be amenable to treatment using a methods disclosed herein include, but are not limited to, cancers of neuroectodermal and epithelial origin. Examples of cancers of neuroectodermal origin include, but are not limited to, Ewings sarcoma, spinal tumors, brain tumors, supratenbrial primative neuroectodermal tumors of infancy, tubulocystic carcinoma, mucinous tubular and spindle cell carcinoma, renal tumors, mediastinum tumors, neurogliomas, neuroblastomas, and sarcomas in adolescents and young adults. Examples of epithelial origin include, but are not limited to, small cell lung cancer, cancers of the breast, eye lens, colon, pancreas, kidney, liver, ovary, and bronchial epithelium. In some embodiments, the treatment methods disclosed herein do not include treatment of melanoma (i.e., the cancer is other than melanoma). In other embodiments, the treatment methods disclosed herein do not include treatment of lymphoma (i.e., the cancer is other than lymphoma). In certain embodiments, the methods of the present disclosure are used to treat cancer cells known to express de-N-acetyl gangliosides include melanomas and some lymphomas. As noted above, cancers that overexpress the precursor gangliosides GM3 and GD3 are likely to also express the greatest amount of de-N-acetyl gangliosides on the cell surface.

Combinations with Other Cancer Therapies

Therapeutic administration of the polysialic acid derivative compositions can include administration as a part of a therapeutic regimen that may or may not be in conjunction with additional standard anti-cancer therapeutics, including but not limited to immunotherapy, chemotherapeutic agents and surgery (e.g., as those described further below).

In addition, therapeutic administration of the polysialic acid derivative compositions can also be post-therapeutic treatment of the subject with an anti-cancer therapy, where the anti-cancer therapy can be, for example, surgery, radiation therapy, administration of chemotherapeutic agents, and the like. Use of monoclonal antibodies, particularly monoclonal antibodies that can provide for complement-mediated killing, and/or antibody-dependent cellular cytotoxicity-mediated killing, of a target cell are of particular interest (e.g., treatment with an anti-deNAc SA epitope antibody (e.g., SEAM 3 or an antibody specific for an polysialic acid derivative of the present disclosure) after identification of a primary tumor composed of cells expressing a deNAc SA epitope (e.g., a de-N-acetyl ganglioside)). Cancer therapy using polysialic acid derivative compositions of the present disclosure in combination with immunotherapy that employs PSA antigen/anti-deNAc SA epitope antibodies is of particular interest (U.S. Ser. No. 11/645,255 and PCT Application No. US2006/048850; incorporated herein by reference).

For example, the polysialic acid derivative compositions can be administered in combination with one or more chemotherapeutic agents (e.g., cyclophosphamide, doxorubicin, vincristine and prednisone (CHOP)), and/or in combination with radiation treatment and/or in combination with surgical intervention (e.g., pre- or post-surgery to remove a tumor). Where the polysialic acid derivative is used in connection with surgical intervention, the polysialic acid derivative compositions can be administered prior to, at the time of, or after surgery to remove cancerous cells, and may be administered systemically or locally at the surgical site. The polysialic acid derivative compositions alone or in combinations described above can be administered systemically (e.g., by parenteral administration, e.g., by an intravenous route) or locally (e.g., at a local tumor site, e.g., by intratumoral administration (e.g., into a solid tumor, into an involved lymph node in a lymphoma or leukemia), administration into a blood vessel supplying a solid tumor, etc.).

Any of a wide variety of cancer therapies can be used in combination with the polysialic acid derivative-based therapies described herein. Such cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, X-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (CYTOXAN™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (TAXOL®), docetaxel (TAXOTERE®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (TAXOL®), TAXOL® derivatives, docetaxel (TAXOTERE®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and ZOLADEX®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); IRESSA® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL, TAXOTERE (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., TAXOTERE™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

In the treatment of some individuals with the compounds of the present present disclosure, it may be desirable to use a high dose regimen in conjunction with a rescue agent for non-malignant cells. In such treatment, any agent capable of rescue of non-malignant cells can be employed, such as citrovorum factor, folate derivatives, or leucovorin. Such rescue agents are well known to those of ordinary skill in the art. Rescue agents include those which do not interfere with the ability of the present inventive compounds to modulate cellular function.

Particular applications in which the methods and compositions disclosed herein find use include those described in U.S. Pat. Nos. 2,512,572; 3,892,801; 3,989,703; 4,057,548; 4,067,867; 4,079,056; 4,080,325; 4,136,101; 4,224,446; 4,306,064; 4,374,987; 4,421,913; 4,767,859; 3,981,983; 4,043,759; 4,093,607; 4,279,992; 4,376,767; 4,401,592; 4,489,065; 4,622,218; 4,625,014; 4,638,045; 4,671,958; 4,699,784; 4,785,080; 4,816,395; 4,886,780; 4,918,165; 4,925,662; 4,939,240; 4,983,586; 4,997,913; 5,024,998; 5,028,697; 5,030,719; 5,057,313; 5,059,413; 5,082,928; 5,106,950; 5,108,987; 4,106,488; 4,558,690; 4,662,359; 4,396,601; 4,497,796; 5,043,270; 5,166,149; 5,292,731; 5,354,753; 5,382,582; 5,698,556; 5,728,692; and 5,958,928; the disclosures of which are herein incorporated by reference.

Production of Anti-Polysialic Acid Derivative Antibody Response

Polysialic acid derivatives, including conjugates thereof, as described herein can be used in eliciting an anti-bacterial antibody response, as well as in eliciting an anti-cancer cell antibody response. In general immunization is accomplished by administration by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

It is recognized that polysialic acid derivatives and related compounds described herein (e.g., conjugates), when administered orally, should be protected from digestion. This is typically accomplished either by complexing the polysialic acid derivative with a composition to render it resistant to acidic and enzymatic hydrolysis or by packaging in an appropriately resistant carrier such as a liposome. Means of protecting a compound of interest from digestion are well known in the art.

In order to enhance serum half-life, the antigenic preparations that are injected may also be encapsulated, introduced into the lumen of liposomes, prepared as a colloid, or other conventional techniques may be employed which provide an extended serum half-life of the peptides. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms for release and administration of the antigen preparations as a mixture or in serial fashion.

The compositions are administered to suitable subject, e.g., a subject that is at risk from acquiring a Neisserial disease or at risk of developing a cancer bearing a deNAc SA epitope (e.g., as present in a SEAM 3-reactive antigen) to prevent or at least partially arrest the development of disease and its complications. An amount adequate to accomplish this is defined as a "therapeutically effective dose." Amounts effective for therapeutic use will depend on, e.g., the antigen composition, the manner of administration, and a variety of subject-specific parameters such as the weight and general state of health of the subject, any or all of which may be modified according to the judgment of the clinician.

Single or multiple doses of the antigen compositions may be administered depending on the dosage and frequency required and tolerated by the patient, and route of administration. In general, immunization is provided to as to elicit an immune response in the subject, where the such immunization may be advantageous in that it does not elicit detectable antibodies that significantly cross-react with polysialic acid in the subject (stated differently, elicits no clinically relevant autoantibody response directed against host sialic acid), and can include production of antibodies bactericidal for *N. meningitidis* as well as for *E. coli* K1 and/or production of antibodies that inhibit cancer cell proliferation.

In particular embodiments, the antigen compositions described herein are administered serially. First, an immunogenically effective dose of a polysialic acid derivative (which may be conjugated to a carrier, and may be with or without excipients) is administered to a subject. The first dose is generally administered in an amount effective to elicit an immune response (e.g., activation of B and/or T cells). Amounts for the initial immunization generally range from about 0.001 mg to about 1.0 mg per 70 kilogram patient, more commonly from about 0.001 mg to about 0.2 mg per 70 kilogram patient, usually about 0.005 mg to about 0.015 mg per 70 kilogram patient. Dosages from 0.001 up to about 10 mg per patient per day may be used, particularly when the antigen is administered to a secluded site and not into the blood stream, such as into a body cavity or into a lumen of an organ. Substantially higher dosages (e.g. 10 to 100 mg or more) are possible in oral, nasal, or topical administration.

After administration of the first antigen composition of polysialic acid derivative, a therapeutically effective dose of a second antigen composition (e.g. polysialic acid derivative, optionally conjugated and with or without excipients) is administered to the subject after the subject has been immunologically primed by exposure to the first dose. The booster may be administered days, weeks or months after the initial immunization, depending upon the patient's response and condition.

The presence of a desired immune response may be determined by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like) and/or demonstrating that the magnitude of the immune response to the second injection is higher than that of a control subject immunized for the first time with the composition used for the second injection (e.g. immunological priming). Immunologic priming and/or the existence of an immune response to the first antigen composition may also be assumed by waiting for a period of time after the first immunization that, based on previous experience, is a sufficient time for an immune response and/or priming to have taken place—e.g. 2, 4, 6, 10 or 14 weeks. Boosting dosages of the second antigen composition are typically from about 0.001 mg to about 1.0 mg of antigen, depending on the nature of the immunogen and route of immunization.

In certain embodiments, a therapeutically effective dose of a third antigen composition prepared from is administered to the subject after the individual has been primed and/or mounted an immune response to the second antigen composition. The methods disclosed herein also contemplate administration of a fourth, fifth, sixth or greater booster immunization, using either a fourth, fifth or sixth antigen composition.

The subject may be immunologically naïve with respect to *Neisseria meningitidis* or *E. coli* K1 or a deNAc SA epitope-bearing cancer. For immunoprevention, the polysialic acid derivative can be administered prior the first sign of disease symptoms, or at the first sign of possible or actual exposure to infection or disease (e.g., due to exposure or infection by *Neisseria* or *E. coli* K1).

Passive Immunization and Other Antibody-Based Therapies

In addition, antibodies generated against polysialic acid derivative or SEAM 3 using the methods described herein can be used to provide for passive immunotherapy, e.g., to treat or prevent *N. meningitidis*-mediated or *E. coli* K1-mediated disease in mammalian subjects. Particularly, the SEAM 3 or antibodies generated using the polysialic acid derivative conjugates thereof according to the present disclosure can be provided in a pharmaceutical composition suitable for administration to a subject, so as to provide for passive protection of the subject against *N. meningitidis* of *E. coli* K1 disease, or for treatment of cancer.

More particularly, immunoprotective antibodies such as SEAM 3 that recognize Neisserial PS or *E. coli* K1 epitopes can be administered to a subject (e.g. a human patient) to induce passive immunity against a Neisserial disease, either to prevent infection or disease from occurring, or as a therapy to improve the clinical outcome in patients with established disease (e.g. decreased complication rate such as shock, decreased mortality rate, or decreased morbidity, such as deafness). Where the antibodies are administered to effect a cancer therapy, the antibodies can optionally have attached a drug for targeting to the cancer cell to effect tumor killing or clearance, e.g., a toxin (e.g., ricin), radionuclide, and the like.

Diagnostics

The polysialic acids derivatives disclosed herein may be used in various diagnostic settings. In particular, they may be used to increase the amount of a detectable antigen on the surface of a cancer cell for secondary detection, or by use of conjugates of the derivatives comprising a detectable label. Also, to facilitate the identification of a subject more amenable to therapy with the compositions of the present disclosure, antibodies such as SEAM 3 that are reactive with a deNAc SA epitope can be used to detect deNAc SA antigens in a biological sample obtained from a subject having or suspected of having bacterial infection or cancerous cells having a cell surface accessible deNAc SA epitope (e.g., a de-N-acetylated cell surface ganglioside or glycoconjugate) using anti-deNAc SA epitope antibodies in immunodiagnostic techniques as described in (See U.S. Ser. No. 11/645,255 and PCT Application No. US2006/048850; incorporated herein by reference). Such diagnostics can be useful to identify patients amenable to the therapies disclosed herein, and/or to monitor response to therapy. Further, such diagnostics can have antibodies that exhibit little or no detectable binding to host (e.g., mammalian, especially human) polysialic acid, thereby providing for decreased risk of false positive results. The diagnostics aspect of the present disclosure can also be exploited for clinical trials and the like, as well as manufacturing and release assays in the product of the compositions of the present disclosure.

Briefly, the antigen binding specificity of anti-deNAc SA epitope antibodies can be exploited in this context, to facilitate detection of deNAc SA epitopes on a cancerous or bacterial cell in a sample with little or no detectable binding to host-derived PSA, thereby reducing the incidence of false positive results. Such detection methods can be used in the context of diagnosis, identification of subject suitable to polysialic acid derivative-based therapy where the antibody specifically binds an deNAc SA epitope and/or a SEAM 3-reactive antigen, monitoring of therapy (e.g., to follow response to therapy), and the like.

Suitable immunodiagnostic techniques include, but are not necessarily limited to, both in vitro and in vivo (imaging) methods. Where the methods are in vitro, the biological sample can be any sample in which a deNAc SA antigen may be present, including but not limited to, blood samples (including whole blood, serum, etc.), tissues, whole cells (e.g., intact cells), and tissue or cell extracts. Assays can take a wide variety of forms, such as competition, direct reaction, or sandwich type assays. Exemplary assays include Western blots; agglutination tests; enzyme-labeled and mediated immunoassays, such as ELISAs; biotin/avidin type assays; radioimmunoassays; immunoelectrophoresis; immunoprecipitation, and the like. The reactions generally include detectable labels such as fluorescent, chemiluminescent, radioactive, enzymatic labels or dye molecules, or other methods for detecting the formation of a complex between antigen in the sample and the antibody or antibodies reacted therewith.

The assays can involve separation of unbound antibody in a liquid phase from a solid phase support to which antigen-antibody complexes are bound. Solid supports which can be used in the practice of the present disclosure include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Where a solid support is used, the solid support is usually first reacted with a solid phase component (e.g., an anti-deNAc SA epitope antibody) under suitable binding conditions such that the component is sufficiently immobilized to the support. Sometimes, immobilization to the support can be enhanced by first coupling the antibody to a protein with better binding properties, or that provides for immobilization of the antibody on the support with out significant loss of antibody binding activity or specificity. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind antibodies the support include polysaccharides, polylactic acids, polyglycolic acids, polymeric amino acids, amino acid copolymers, and the like, with the proviso that the molecule used to immobilize the antibody does not adversely impact the ability of the antibody to specifically bind antigen. Such molecules and methods of coupling these molecules to the antigens, are well known to those of ordinary skill in the art. See, e.g., Brinkley, M. A. Bioconjugate Chem. (1992) 3:2-13; Hashida et al., J. Appl. Biochem. (1984) 6:56-63; and Anjaneyulu and Staros, International J. of Peptide and Protein Res. (1987) 30:117-124.

After reacting the solid support with the solid phase component, any non-immobilized solid-phase components are removed from the support by washing, and the support-bound component is then contacted with a biological sample suspected of containing deNAc SA epitopes under suitable binding conditions. After washing to remove any non-bound ligand, a secondary binder moiety is added under suitable binding conditions, wherein the secondary binder is capable of associating selectively with the bound ligand. The presence or absence of the secondary binder can then be detected using techniques well known in the art.

An ELISA method can be used, wherein the wells of a microtiter plate are coated with anti-deNAc SA epitope antibody according to the present disclosure. A biological sample containing or suspected of containing a deNAc SA antigen (e.g., a tumor antigen having a deNAc SA epitope, such as a de-N-acetylated ganglioside), is then added to the coated wells. After a period of incubation sufficient to allow antibody binding, the plate(s) can be washed to remove unbound moieties and a detectably labeled secondary binding molecule added. The secondary binding molecule is allowed to react with any captured antigen, the plate washed and the presence or absence of the secondary binding molecule detected using methods well known in the art.

Where desired, the presence or absence of bound deNAc SA antigen from a biological sample can be readily detected using a secondary binder comprising an antibody directed against the antibody ligands. For example, a number of anti-murine immunoglobulin (Ig) molecules are known in the art, which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antibodies and deNAc SA antigen form complexes under precipitating conditions. For example, the antibody can be attached to a solid phase particle (e.g., an agarose bead or the like) using coupling techniques known in the art, such as by direct chemical or indirect coupling. The antibody-coated particle is then contacted under suitable binding conditions with a biological sample suspected of containing deNAc SA antigen to provide for formation of particle-antibody-deNAc SA antigen complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

The test sample used in the diagnostics assays can be any sample in which a deNAc SA antigen may be present, including but not limited to, blood samples (including whole blood, serum, etc.), tissues, whole cells (e.g., intact cells), and tissue or cell extracts containing cells (e.g., tissue, isolated cells, etc.), a cell lysate (i.e., a sample containing non-intact cells), where each type of sample can contain elements of both types (e.g., a sample of cells can contain cell lysates, and vice versa). In some embodiments, particularly as in embodiments involving detection of cancer cells, it may be desirable to conduct the assay using a sample from the subject to be diagnosed that contains intact, living cells. deNAc SA antigen detection can then be assessed on an extracellular surface of the cells, and can further be assessed during cell division.

Diagnostic assays can also be conducted in situ. For example, anti-deNAc SA epitope antibodies can be detectably labeled, administered to a subject suspected of having a cancer characterized by cell surface expression of a deNAc SA epitope, and bound detectably labeled antibody detected using imaging methods available in the art.

The diagnostic assays described herein can be used to determine whether a subject has a bacterial infection or cancer that is more or less amenable to therapy using polysialic acid derivative-based therapy, as well as monitor the progress of treatment in a subject. It also may be used to assess the course of other combination therapies (e.g., deNAc SA antigen vaccine and/or anti-deNAc SA antigen antibody therapy as described in (U.S. Ser. No. 11/645,255 and PCT Application No. US2006/048850; incorporated herein by reference). Thus, the diagnostic assays can inform selection of therapy and treatment regimen by a clinician.

Where the methods are in vitro, the biological sample can be any sample in which a SEAM 3-reactive antigen may be present, including but not limited to, blood samples (including whole blood, serum, etc.), tissues, whole cells (e.g., intact cells, i.e., cells that have not been subjected to permeabilization), or cell lysates (e.g., as obtained from treatment of a tissue sample). For example, the assay can involve detection of a SEAM 3-reactive antigen on cells in a histological tissue sample. For example, the tissue sample may be fixed (e.g., by formalin treatment) and may be provided embedded in a support (e.g., in paraffin) or frozen unfixed tissue.

The SEAM 3-reactive antigen can be detected by detection of specific binding of an antibody, usually a monoclonal antibody (mAb), that has the antigen-binding specificity of SEAM 3. In this embodiment, the SEAM 3-reactive antigen may be present on the cell surface at any stage of the cell cycle, including during cell division. Of note is that in some instances, cancers that present a SEAM 3-reactive antigen during cell division may present a lower or no detectable level of SEAM 3-reactive antigen when the cell is quiescent (i.e., not undergoing cell division). However, as illustrated in the examples below, SEAM 3-reactive antigen can be detected in non-dividing cells by detecting SEAM 3-reactive antigen in a permeabilized test cell. A test cancer cell that exhibits a pattern of staining with a SEAM 3 antibody (or an antibody having the antigen binding specificity of SEAM 3) that is distinct from a pattern of antibody staining in a normal cell is identified as a cancerous cell that exhibits a SEAM 3-reactive antigen. Such cancers are thus amenable to therapy with an antibody that specifically binds the SEAM 3-reactive antigen (e.g., the mAb SEAM 3).

The above-described assay reagents, including the antibodies generated by immunization with a deNAc SA antigen according to the methods described in U.S. Ser. No. 11/645, 255 and PCT Application No. US2006/048850, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Kits & Systems

Also provided are kits and systems that find use in practicing the methods of the present disclosure, as described above. For example, kits and systems for practicing the methods of the present disclosure may include one or more pharmaceutical formulations that include polysialic acid derivative. As such, in certain embodiments the kits may include a single pharmaceutical composition present as one or more unit dosages. In yet other embodiments, the kits may include two or more separate pharmaceutical compositions.

Thus the kits can include one or more of, depending upon the intended use of the kit, the compositions described herein, such as: a polysialic acid derivative and/or antibody specific thereto, cells suitable related for assays or screening, an anti-deNAc SA epitope antibody, and the like. Other optional components of the kit include: buffers, etc., for administering a polysialic acid derivative and/or antibody specific thereto, and/or for performing a diagnostic assay. The various components of the kit may be present in separate containers or certain compatible components may be pre-combined into a single container, as desired.

In addition to the above components, the kits may further include instructions for practicing the methods disclosed herein. These instructions may be present in the kits in a variety of forms, one or more of which may be present in or on the kit. One form in which these instructions may be present is as printed information on a suitable medium or substrate, e.g., a piece or pieces of paper on which the information is printed, in or on the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

In a specific embodiment, a kit is provided for use in treating a host suffering from a cellular proliferative disease condition. This kit includes a pharmaceutical composition comprising an polysialic acid derivative, and instructions for the effective use of the pharmaceutical composition in a method of treating a host suffering from a cancerous condition by enhancing de-N-acetyl sialic acid antigen of a cancer cell so as to facilitate an immune response against the cancer cell and/or facilitate binding of an anti-de-N-acetyl sialic acid antigen to the cancer cells, and/or by providing for administration of an immunogenic form of a polysialic acid derivative to elicit an anti-de-N-acetyl sialic acid antigen immune response, e.g., to elicit antibodies that bind a cancer cell bearing a deNAc SA epitope. Such instructions may include not only the appropriate handling properties, dosing regiment and method of administration, and the like, but can further include instructions to optionally screen the subject for a de-N-acetylated sialic acid (deNAc SA) epitope. This aspect can assist the practitioner of the kit in gauging the potential responsiveness of the subject to treatment with a polysialic acid derivative and/or antibody specific thereto, including timing and duration of treatment relative to the type and growth stage of the cancer. Thus in another embodiment, the kit may further include an antibody or other reagent for detecting a de-N-acetylated sialic acid (deNAc SA) epitope on an extracellularly accessible surface of a cancer cell, such as SEAM 3 (ATCC Deposit No. HB-12170). In another embodiment, the kit includes one or more polysialic acid derivatives that comprise a conjugate with a detectable label, such as a fluorophore. Such polysialic acid derivatives can be useful in labeling cancer cells either in vitro (e.g., as in a biopsy) or in vivo (e.g., as in in situ imaging methods), where the cancer cells incorporate the detectably labeled polysialic acid derivative to as to provide for an increase in a detectable signal in cancerous cells (e.g., as compared to non-cancerous cells into which little or no detectable polysialic acid derivative is incorporated).

In another specific embodiment, a kit is provided for use in immunizing a host at risk of, or having, a disease or disease symptom of infection by a bacteria bearing a deNAc SA epitope, e.g., a deNAc SA epitope on a bacterial polysaccharide capsule (e.g., *Neisseria* (e.g., *N. meningitidis*, especially Group B *N. meningitidis*), *E. coli* K1). This kit includes a pharmaceutical composition comprising a polysialic acid derivative and/or antibody specific thereto, and instructions for the effective use in immunization or treatment of a host having, or at risk of, bacterial infection. Such instructions may include not only the appropriate handling properties, dosing regiment and method of administration, and the like, but can further include instructions to optionally screen the subject for a de-N-acetylated sialic acid (deNAc SA) epitope. This aspect assists the practitioner of the kit in gauging the potential responsiveness of the subject to immunization with a polysialic acid derivative and/or antibody specific thereto. Thus in another embodiment, the kit may further include an antibody or other reagent for detecting a de-N-acetylated sialic acid (deNAc SA) epitope on an extracellularly accessible surface of a cancer cell, such as SEAM 3 (ATCC Deposit No. HB-12170).

The term "system" as employed herein refers to a collection of an polysialic acid derivative and/or antibody specific thereto and one or more second therapeutic agents, present in single or disparate compositions that are brought together for the purpose of practicing the methods disclosed herein. For example, separately obtained polysialic acid derivative and/or antibody specific thereto and chemotherapy dosage forms brought together and co-administered to a subject are a system according to the present invention.

The following examples further illustrate the present invention and should not be construed as in any way limiting its scope.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Preparation of a synthetic de-N-acetyl sialic acid antigen (poly alpha (2→8) N-acetyl neuraminic acid) that is enriched in non-reducing end de-N-acetyl residues and resistant to exoneuraminidase degradation is described in Examples 1-3. Testing of the material against other polysialic acid materials not-enriched or resistant to exoneuraminidase degradation, and their ability to be taken up and presented on the cell surface without being substantially degraded following exogenous exposure to various cancer cells is described in Examples 4-5. Example 6 describes the ability of the synthetic antigen to facilitate not only binding of antibody, but its uptake into the cell. Examples 7 and 8 describe the preparation of N-propionyl PSA antigen and SEAM 3 inhibitor assay, respectively. Example 9 describes an exemplary method for determining N-acetyl sialic acid and de-N-acetyl sialic acid content in polysialic acid (PSA) derivatives (and shorter chain length PSA derivatives referred to as oligosialic acid or oligosaccharide (OS) derivatives). Example 10 describes production of defined OS derivatives containing de-N-acetyl sialic acid residues by time controlled alkaline de-N-acetylation. Example 11 describes the effect of OS produced in accordance with Example 10 on the viability of Jurkat T-cell leukemia cells. Example 12 describes production of defined OS derivatives enriched for non-reducing end de-N-acetyl residues by time controlled de-N-acetylation and non-oxidizing acid hydrolysis of PSA materials. Example 13 describes the purification of OS derivatives produced in accordance with Example 12 that are cytotoxic to Jurkat leukemia cells.

Example 1

De-N-Acetylation of Colominic Acid

Colominic acid (100 mg, Sigma-Aldrich Chemical Company, Saint Louis, Mo.) and 10 mg of sodium borohydride (Sigma-Aldrich) were dissolved in 8.8 ml of water. A solution of 50% (weight/weight) of sodium hydroxide (1.2 ml) was added, the solution was mixed, placed in a glass hydrolysis tube fitted with a Teflon closure (Pierce Chemical Company, Rockford, Ill.), and heated to 90° C. to 100° C. for 2 hrs. The solution was allowed to cool to ambient temperature and 2M HCl was added to lower the pH of the solution to approximately 8. The solution was dialyzed (1 kDa cutoff) twice in 4 L of water and lyophilized.

Example 2

Partial Re-N-Acetylation of De-N-Acetylated Colominic Acid

The lyophilized de-N-acetylated colominic acid (approximately 80 mg) was resuspended in 5 ml of water and the pH adjusted to 8-9 with 2M NaOH. Acetic anhydride (Sigma-Aldrich) was added in five aliquots of 0.1 ml over a period of several hours with stirring. The pH of the solution was monitored with a pH meter and 2M NaOH was added as necessary to maintain the pH between 8 and 9. At the completion of the reaction, the solution was dialyzed and lyophilized as before. The re-N-acetylated colominic acid typically contains 10% to 30% de-N-acetylated residues as determined by resorcinol assay (see Example 9).

Example 3

Enrichment for PSA Containing Non-Reducing End De-N-Acetyl Residues

The PSA material of Example 2 was enriched for non-reducing end de-N-acetyl residues by treatment with the exoneuraminidase SIALIDASE A™ (Prozyme, San Leandro, Calif.). Lyophilized re-N-acetylated colominic acid powder (50 mg) from Example 2 was resuspended in 2.5 ml of 50 mM sodium phosphate buffer, pH 7. SIALIDASE A™ (10 µl, 1 U/ml, Prozyme) was added and the solution was transferred to dialysis tubing (1 kDa cutoff) then placed in 1 L of 50 mM sodium phosphate buffer, pH 7 at 37° C. for 3-4 days. N-acetyl neuraminic acid released by the enzyme passes through the dialysis membrane, whereas enzyme and PSA terminating at the non-reducing end in a de-N-acetyl residue is retained.

Alternatively, the PSA material was resuspended in 5.0 ml of 50 mM sodium acetate buffer, pH 6.5. Sialidase A (25 ul, 1 U/ml) was added and the reaction placed at 37° C. for 2 days. Afterwards, 0.1 M NaOH was added for 1 hr at room temperature to terminate the reaction, then neutralized with glacial AcOH. N-acetyl neuraminic acid released by the enzyme was removed by dialysis (1 kDa cutoff) against 4 L water, two times.

Example 4

Increasing Expression of Seam 3-Reactive Antigens in Cancer Cells

The effect of exogenous PSA derivatives from Example 3 was tested on the expression of PSA antigens that contained neuraminic acid (that is, de-N-acetyl neuraminic acid residues in PSA). CHP-134 neuroblastoma, Jurkat T-cell leukemia, and SK-MEL 28 melanoma cells were examined for binding to SEAM 3 exposed to the PSA derivatives by flow cytometry after culturing the cells in the presence of the derivatives. SEAM 3 specifically recognizes PSA containing neuraminic acid residues (U.S. Ser. No. 11/645,255 and PCT Application No. US2006/048850; incorporated herein by reference).

Cells (approximately $10^5$ per well) were plated onto a flat bottom 96-well tissue culture plate (Nunc, Thermo-Fisher) and incubated with growth medium supplemented with 10 mM (based on a residue mass of 290 Da) colominic acid (i.e. PSA capsular polysaccharide from *E. coli* K1 bacteria, Sigma-Aldrich), re-N-acetylated colominic acid ("ReAc") that had not been treated with SIALIDASE A™, and SIALIDASE A™-treated re-N-acetylated PSA ("ReAcSia") for 24 hrs before measuring binding. Prior to adding to the cell cultures, the colominic acid derivatives were heated to 56° C. for 1 hr to inactivate any contaminating microorganisms.

After incubation, cells were detached from the plate (Jurkat cells are non-adherent) by either trypsin (SK-MEL-28) or Cell Dispersal Reagent (CDR, Guava Technologies, Hayward, Calif.) (CHP-134) before being collected into a 96-round bottom plate (Falcon), spun at 1000×g for 5 minutes and fixed with ice-cold 1% (v/v) formaldehyde. After 20 minutes cells were pelleted by centrifugation (above) and incubated in a blocking solution of 3% (v/v) goat serum for 1 hour. After blocking, the primary antibodies were added and incubated overnight at 4° C. The cells were washed twice by pelleting and resuspension in ice-cold PBS. Secondary antibody (FITC-conjugated goat anti-mouse IgG (Fab)$_2$, Jackson Immunoresearch, West Grove, Pa.) was incubated with the cells for at least 1 hour at 4° C. in the dark. After another series of spins and washes (3 times) binding was analyzed by a Guava EastCyte flow cytometer (Guava Technologies). Control samples were treated with an isotype matched irrelevant antibody (Southern Biotech, Birmingham, Ala.), which were used to create baseline fluorescence, or positive control mAbs that are reactive with antigens specifically expressed by the cells (i.e. anti-GD3 mAb R24 (MEL-1 from Axxora LLC, San Diego, Calif.) for SK-MEL 28 cells.

Figure 4:
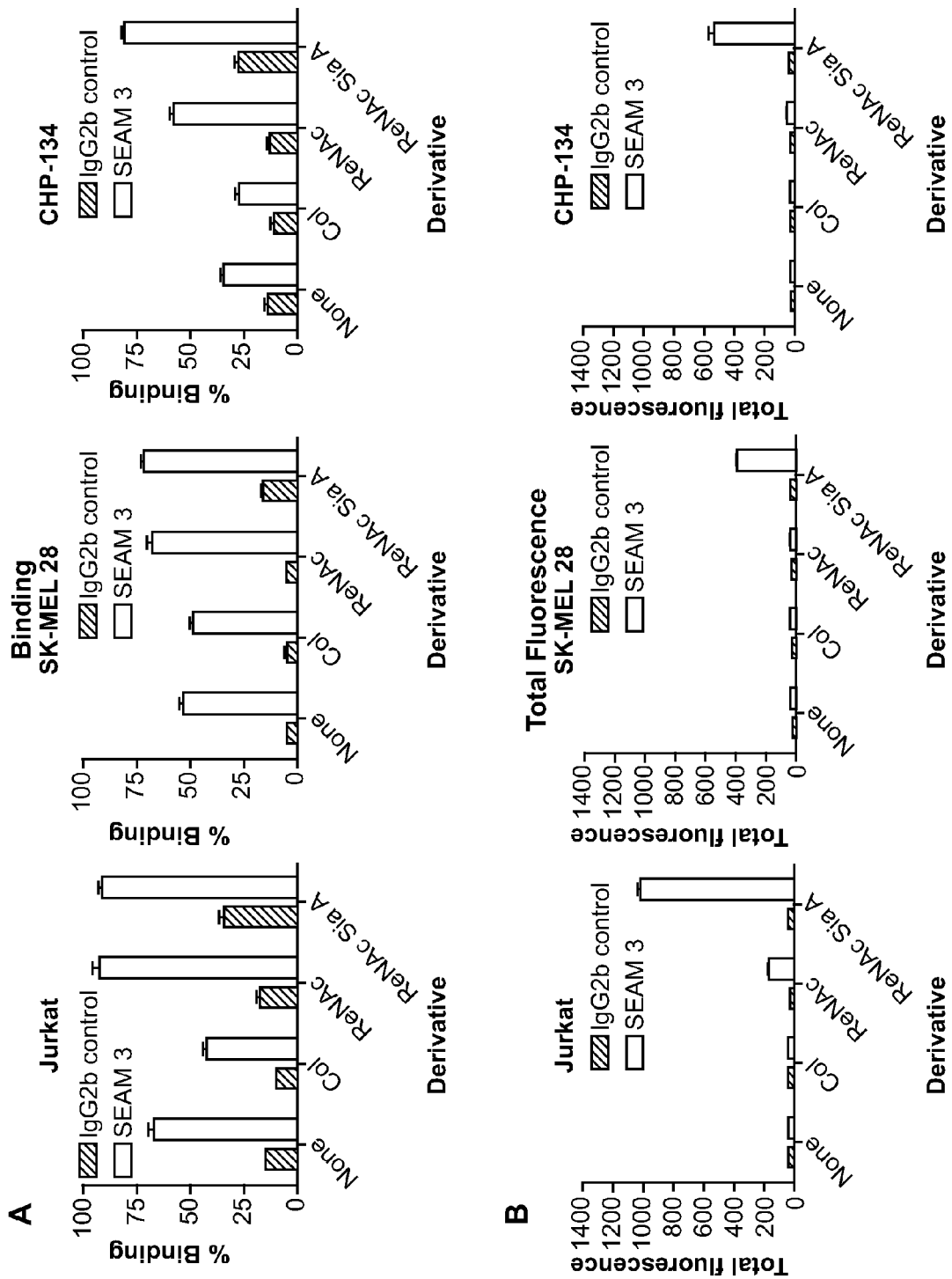
FIG. 4 shows results in histogram format for an irrelevant, isotype-matched control mAb IgG2b and SEAM 3 binding (FIG. 4, Panel A) and total fluorescence of cells (FIG. 4, Panel B) for Jurkat, SK-MEL 28 melanoma and CHP-134 neuroblastoma cells exogenously exposed to no derivative (None), a polysialic acid (colominic acid (Col)), a re-N-acetylated polysialic acid derivative (re-N-acetylated colominic acid (ReAc)), and a polysialic acid derivative that is resistant to exoneuraminidase (re-N-acetylated colominic acid that has been selected for resistance to exoneuraminidase (ReAcSia)).

As shown in FIGS. 1-4, SEAM 3 binds to the surface of all three cell lines. The percent of cells positive for SEAM 3 binding increases when the cells were incubated with either re-N-acetylated colominic acid ("ReAc") or SIALIDASE A™-treated re-N-acetylated PSA ("ReAcSia") compared to no derivative (None) or colominic acid (Col) as shown in FIG. 4. In fact, incubation with colominic acid decreases the percentage of cells that are positive for SEAM 3 binding (FIG. 4 upper panels). Importantly, the fluorescence of cells incubated with sialidase-treated re-N-acetylated colominic acid (ReAcSia) increases 10- to 30-fold (FIG. 4 lower panels) compared to no derivative, colominic acid, or re-N-acetylated colominic acid (ReAc) demonstrating that the amount of SEAM 3-reactive PSA containing neuraminic acid on the cell surface is greatly increase by providing the derivative exogenously.

Example 5

Confocal Microscopy

To show that the exogenously supplemented SIALIDASE A™-treated re-N-acetylated PSA ("ReAcSia") is taken up by cells and incorporated into glycoconjugate, binding of SEAM 3 to SK-MEL 28 cells incubated with colominic acid or ReAcSia prepared as described in Example 3 was analyzed by confocal microscopy. SK-Mel-28 cells (approximately $10^5$ cells) were cultured on multi-well microscope slides that had been treated with ploy-L-lysine (Nunc). After an overnight incubation with the indicated colominic acid derivative (2.5 mg/ml), cells were gently washed with PBS buffer and fixed with ice-cold 1% (v/v) formaldehyde. After 20 minutes cells were washed with PBS before blocking non-specific binding with a solution of 5% goat serum for 1 hour. To observe the presence of SEAM 3-reactive antigen that is present inside the cells, the cells were treated Triton X-100 (0.5% weight/volume; Sigma) in 5% goat serum for 1 hour. After removing the Triton by pelleting the cells and washing, he primary antibodies were added and incubated for overnight at 4° C. Cells were gently washed by a series (at least twice) with ice-cold PBS before isotype-specific secondary antibody (produced in goat) conjugated with either Alexa Fluor 488, Alexa Fluor 546, or Alexa Fluor 633 was applied for at least 1 hour at 4° C. in the dark (all secondary antibodies conjugated to fluorophores were obtained from Invitrogen, Carlsbad, Calif.). After another series of gentle washes, a hardening mounting medium containing DAPI (Vectrashield™, Vector Laboratories, Burlingame, Calif.) was applied.

Confocal images were obtained using a Zeiss Meta510 CLSM microscope at the Biological Imaging Facility, University of California, Berkeley, Calif. and were analyzed using ImageJ Software (NIH). Control antibodies and secondary antibodies applied alone were routinely used to assess background fluorescence. The positive control mAb that is specific for the ganglioside GD3, R24 was positive for binding to SK-MEL-28 melanoma cells (data not shown).

Figure 5:
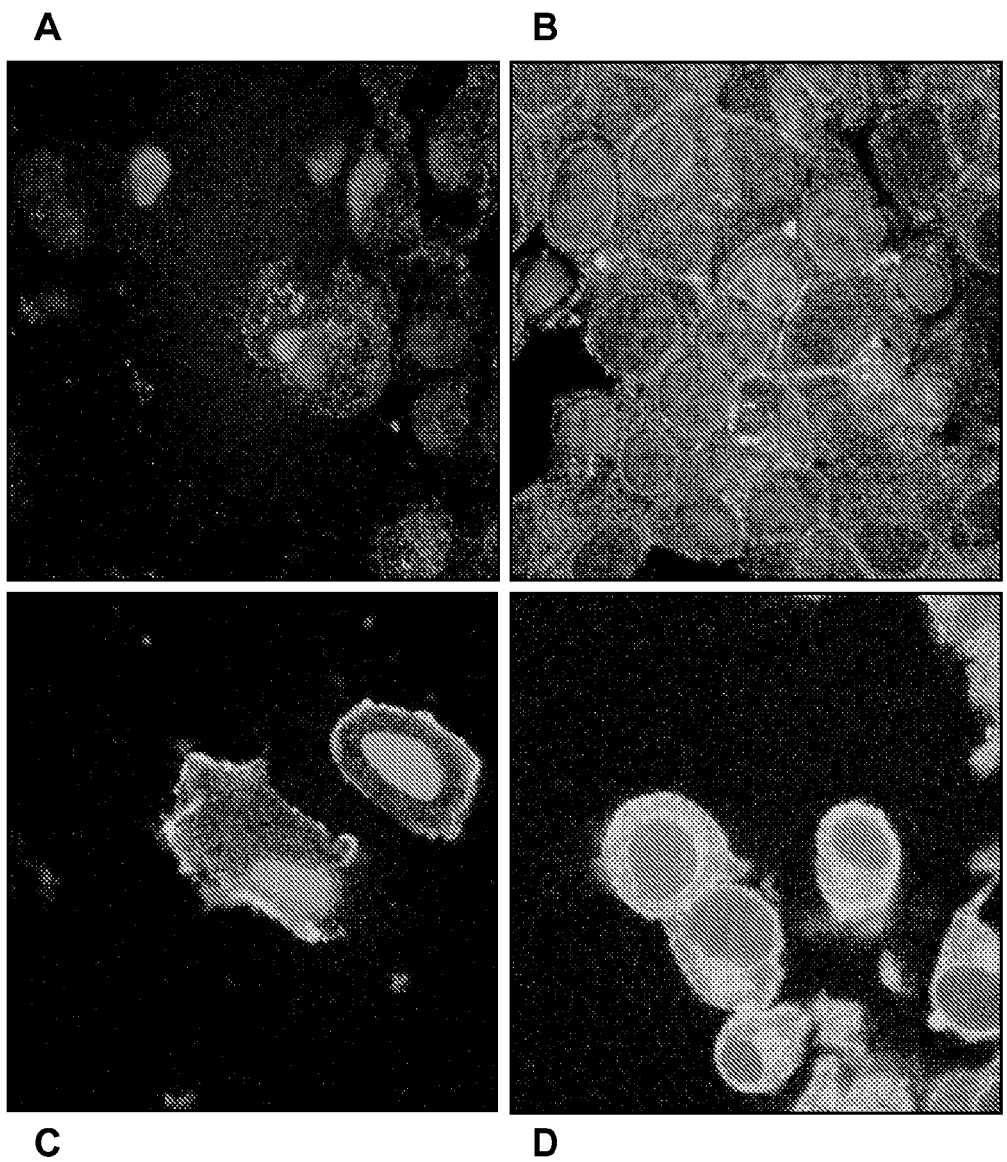
FIG. 5 shows the fluorescence on the cell surface (indicated y red staining, represented in the gray scale figure by light gray surrounding a darkly stained nucleus), as measured by confocal microscopy, resulting from SEAM 3 binding to SK-MEL-28 melanoma cells exogenously exposed to a polysialic acid derivative (FIG. 5, Panels A and C, colominic acid) or to a polysialic acid derivative that is resistant to exoneuraminidase (FIG. 5, Panels B and D, re-N-acetylated colominic acid that has been selected for resistance to exoneuraminidase ReAcSia) in the absence (FIG. 5, Panels A and B) or presence (FIG. 5, Panels C and D) of Triton X-100.

FIG. 5 shows the fluorescence on the cell surface (red staining in the gray scale figure represented by light gray surrounding a dark nucleus) resulting from SEAM 3 binding to SK-MEL-28 melanoma cells as measured by confocal microscopy. The fluorescence is uniform over the cell surface and all cells in the visual field show bright fluorescence associated with SEAM 3 binding. FIG. 5, Panel A shows cells incubated with colominic acid alone, FIG. 5, Panel B shows the large increase in SEAM 3 binding when cells were incubated with re-N-acetylated colominic acid treated with sialidase ("ReAcSia"). FIG. 5, Panels C and 5D show the presence of intracellular SEAM 3-reactive antigens in cells incubated with colominic acid or ReAcSia, respectively, made permeable to the mAb by treatment with the detergent Triton X-100. The increased presence of SEAM 3-reactive antigens inside the cells revealed by confocal microscopy shows that contacting the cells with the ReAcSia derivative results in cellular uptake of the derivative and incorporation into glycoconjugates present in intracellular vesicles, the golgi complex, and the nuclear membrane.

Example 6

Measuring Monoclonal Antibody Uptake—Internalization of Seam 3 by SK-MEL 28 Cells The purpose of this experiment was to determine whether SEAM 3 bound to antigens expressed on the cell surface results in SEAM 3 being taken up by the cells through endocytosis. SK-MEL 28 cells were cultured on 6 well tissue culture plates (Nunc) as described above in Example 5. SEAM 3 (1 µg/ml), anti-GD3 mAb R24 (10 µg/ml), and irrelevant mouse IgG2b and IgG3 isotype control mAbs (10 µg/ml, Southern Biotech, Birmingham, Ala.) were incubated with the cells for 48 hrs. The adherent cells were then gently washed 3× with PBS buffer and finally suspended in RIPA cell lysis and extraction buffer (250 µl, Pierce Chemical Company, Rockford, Ill.) using the plunger from a 1 ml plastic syringe to mix the cells and buffer. The cell/RIPA suspension was mixed with an equal volume of 2×SDS-PAGE sample buffer, boiled for 5 min and the proteins were separated on a 4% to 15% SDS-PAGE gradient gel (Bio-Rad, Richmond, Calif.).

Figure 6:
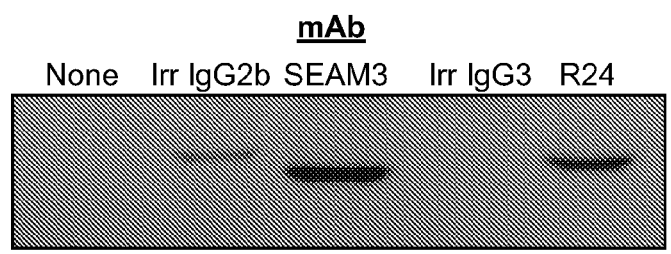
FIG. 6 is a Western blot detecting the presence of mouse immunoglobulin light chains in soluble SK-MEL 28 melanoma cytosolic cell proteins separated on a SDS-PAGE gel after culturing the cells for 48 hrs in the presence of SEAM 3 or control mAbs.
Figure 7:
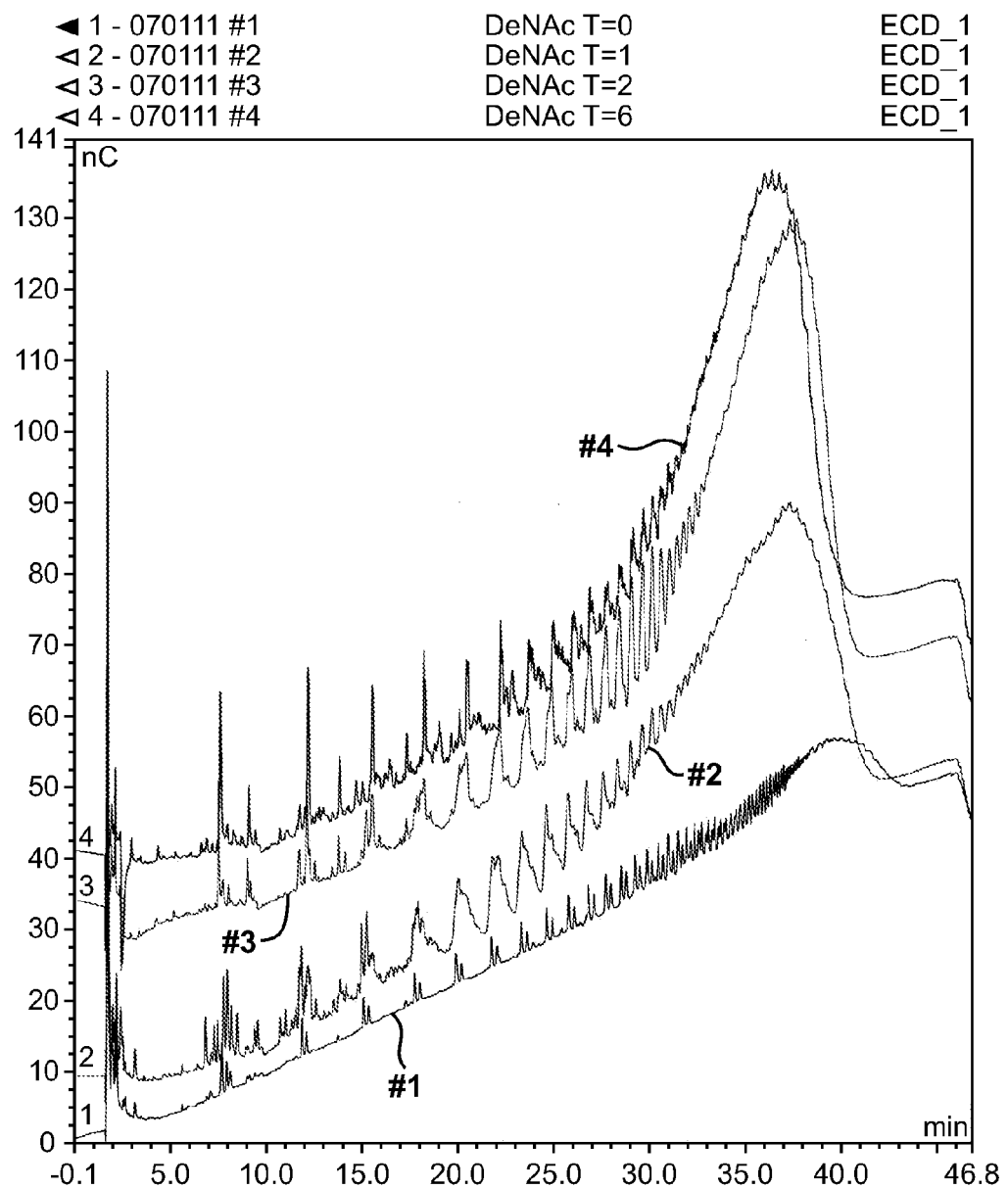
FIG. 7 shows HPAC-PAD chromatograms of colominc acid 0, 1, 2, and 6 hours of alkaline hydrolysis.

The separated proteins were transferred to a nitrocellulose membrane for Western blot using a Bio-Rad semi-dry transfer apparatus. After blocking the membrane for 1 hour with 5% non-fat dry milk in PBS buffer, HRP-conjugated rabbit anti-mouse IgG, A, M secondary antibody (Zymed, South San Francisco, Calif.) was added in the same PBS/5% milk blocking buffer. The membrane was washed and developed with Western Lighting chemiluminescence reagents (PerkinElmer, Waltham, Mass.). The region of the gel having an apparent molecule mass range of about 15 kDa to about 35 kDa where the IgG light chain is located is shown in FIG. 6.

The Western blot shows that there was either a small amount (IgG2b) or no (IgG3) uptake of the negative control irrelevant mAbs. In contrast, endocytosis of R24, which has been shown to be internalized by SK-MEL 28 cells (Iglesia- Bartolome et al, FEBS J, 2006, 273:1744) and especially SEAM 3 was greatly increased. Thus, SEAM 3 binding to antigens expressed on the surface of SK-MEL 28 cells facilitate entry of the mAb into cells and provide a means of delivering cytotoxic drugs and toxins attached to the mAb.

Example 7

Preparation of Dodecylamine N-Propionyl Polysialic Acid (NPr PSA)

deNAc PSA (50 mg) prepared as described in Example 1, was suspended in water (5 ml) and the pH adjusted to 8-9 with 2M NaOH. Propionic anhydride (Sigma-Aldrich) was added to the stirred solution in 5 0.1 ml aliquots over a period of 1 hr. The pH was maintained between 8 and 9 by adding 2 M NaOH. The reaction mixture was dialyzed in water and lyophilized as described above.

A solution of NPr PSA (10 mg/ml) was oxidized by with 1 mM sodium periodate (Sigma-Aldrich) in sodium acetate buffer, pH 6.5 for 30 minutes at ambient temperature in the dark. Excess periodate was destroyed by adding a solution of ethylene glycol (Sigma-Aldrich) in water to a final concentration of 1% (volume/volume) and incubating the solution for an additional 30 minutes. The solution was dialyzed in water and lyophilized.

Twenty (20) mg of oxidized NPr PSA prepared as described above was combined in water (5 ml) with 5 µl of dodecylamine (Thermo-Fisher). The pH was adjusted to 8 with 2M HCl and the mixture stirred for 3 hrs. Sodium cyanoborohydride (5 mg, Sigma-Aldrich) was added and the mixture was stirred at ambient temperature for 24 hours then dialyzed in water for 3 to 5 days to remove excess dodecylamine. The dodecylamine NPr derivatives (~1 mg/ml in PBS buffer) was stored at 4° C.

Example 8

Seam 3 Inhibitor Assay

ELISA plates for testing inhibitors of SEAM 3 binding were prepared by diluting a selected dodecylamine NPr derivative of Example 7 above 1:200 in PBS buffer and adding 100 µl per well of a 96 well microtiter plate (Immulon II HB, Dynatech, Chantilly, Va.). The plates were stored overnight at 4° C. before use in assays. The plates were washed with PBS buffer (5×) and blocked with PBS buffer containing 1% (weight/volume) of bovine serum albumin (Sigma; blocking buffer) for 1 hour at ambient temperature. The PSA and OS derivatives were diluted in blocking buffer on the plate then SEAM 3 was added in blocking buffer (100 μl total per well). After incubating the plate overnight at 4° C., the plates were washed with PBS buffer (5×) and rabbit anti-mouse-alkaline phosphatase conjugate antibody (Zymed, South San Francisco, Calif.) diluted in blocking buffer was added. After incubating an additional hour, the plates were washed (5×) with PBS buffer and the bound antibody was detected by adding p-nitrophenyl phosphate substrate (Sigma-Aldrich) in 50 mM sodium carbonate buffer, pH 9, containing 1 mM $MgCl_2$. The absorbance at 405 nm after 60 minutes incubation at ambient temperature was measured using a BioRad Model 550 microtiter plate reader (Richmond, Calif.).

Example 9

Determination of N-Acetyl and De-N-Acetyl Sialic Acid Content in PSA and OS

The concentration of sialic acid and de-N-acetyl sialic acid in PSA or OS derivative stock solutions or column fractions was determined by the Svennerholm resorcinol reaction (Svennerholm, L. (1957) Biochim. Biophys. Acta 24:604) modified as follows. Resorcinol working reagent was prepared by combining 9.75 ml of water, 0.25 ml of 0.1 M CuSO4.5H2O, 10 ml of 20 milligram per ml solution of resorcinol in water, and 80 ml of concentrated HCl. The resorcinol working reagent (100 μl) was combined with the sialic acid or de-N-acetyl sialic acid sample solution (up to 50 micrograms of sialic acid) or standard stock solution in water (100 μl) in a polypropylene deep well (2 ml) microtiter plate. The plate was sealed with a plate cover and heated in a boiling water bath for 30 minutes. After cooling to ambient temperature, isoamyl alcohol (200 μl) was added and mixed using a pipette. The phases were allowed to separate and the upper isoamyl alcohol layer was removed to a clean microtiter plate. 100 μl of the isoamyl alcohol extract and the lower aqueous solution were transferred separately to a polystyrene microtiter plate and the absorbance at 495 nm and 580 nm was measured.

The amount of N-acetyl sialic acid was determined from the absorbance of the isoamyl alcohol fraction at 585 nm and the amount of de-N-acetyl sialic acid was determined from the absorbance of the aqueous fraction at 495 nm in comparison to a standard curve for each. The N-acetyl sialic acid standard was N-acetyl neuraminic acid (Sigma) and the de-N-acetyl sialic acid standard was prepared as described in Example 1 except that the alkaline hydrolysis reaction was 6 hours instead of 2 hours. The amount of de-N-acetyl sialic acid was corrected for the amount of de-N-acetylation that occurs during the acid hydrolysis step of the assay by measuring the amount of de-N-acetylation that occurs in the sialic acid standard.

Example 10

Production of Os Derivatives by Time-Controlled De-N-Acetylation

Synthesis of a mixture of PSA and OS derivatives enriched at the non-reducing end for de-N-acetyl sialic acid residues is described in Example 3 and employs an enzymatic step. The chemical synthesis method described below does not require the use of enzymes, generates products containing few side products, and facilitates the purification of defined OS derivatives.

Colominic acid (100 mg) was combined with 10 mg of sodium borohydride in 2M sodium hydroxide and heated to 90° C. to 100° C. in a glass hydrolysis tube as described in Example 1. Aliquots of 1 ml were removed for analysis by high performance anion exchange chromatography with pulsed ampermetric detection (HPAC-PAD) using a CarboPac PA200 column (column, GP40 pump and ED40 electrochemical detector were from Dionex, Sunnyvale, Calif.) at T=0, 1, 2, and 6 hrs. The column was eluted with a gradient of 93% buffer A (0.1 M sodium hydroxide) 7% buffer B (0.1 M sodium hydroxide containing 1 sodium acetate) to 0% buffer A and 100% buffer B over 40 minutes at a flow rate of 0.5 ml/minute. FIG. 7 shows HPAC-PAD chromatograms of the reaction mixture for each time point (1: t=0; 2: t=1 hr; 3: t=2 hrs; 4: t=6 hrs). Smaller oligosaccharides elute early and longer polysaccharides later. Each oligomer appears as a doublet at T=0 (chromatogram 1) since the sodium borohydride reduction of the C2 ketone produces two enantiomers. The progress of de-N-acetylation with increasing time is indicated by the appearance of multiple peaks for each oligomer after 1 hour which eventually convert to a single peak for each oligomer with complete de-N-acetylation. After 2 hrs, an increasing number of degradation products are produced that appear as peaks between oligomer peaks.

Figure 8:
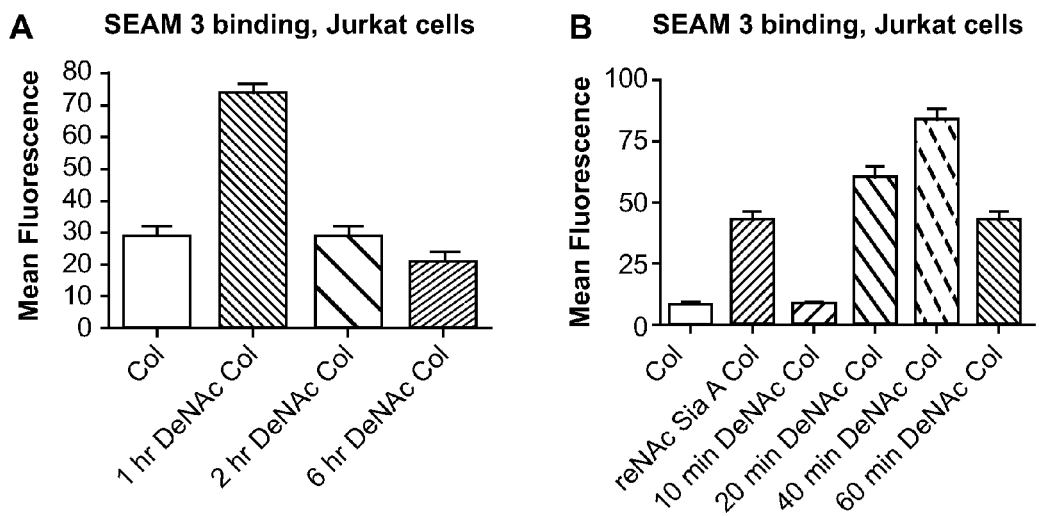
FIG. 8 contains bar graphs showing the effect on SEAM 3 binding to Jurkat cells after contacting the cells with colominic acid derivatives produced by alkaline hydrolysis for 1, 2, or 6 hours (panel A) or 10, 20, 40, or 60 minutes compared to the ReAcSia derivative (panel B).

To determine the optimal time for alkaline de-N-acetylation, the oligosaccharides in each aliquot were tested for their ability to increase binding of SEAM 3 to Jurkat cells using the flow cytometric binding assay described in Example 4. Before use in the binding assay, the pH of the aliquots was adjusted to 8 with 2M HCl, they were dialyzed in water, lyophilized and solutions (2.5 mg/ml) were sterilized by heating to 56° C. as described above. FIG. 8, Panel A is a bar graph showing the mean fluorescence of Jurkat cells resulting from SEAM 3 binding detected with a fluorescently labeled secondary antibody. Based on the data presented in FIG. 8, Panel A, the optimal time for de-N-acetylation is 1 hr or less. The same experiment was repeated with aliquots sampled after hydrolysis for 10, 20, 40, and 60 minutes and were tested for the ability to increase SEAM 3 binding (Example 4). As shown in FIG. 8, Panel B, de-N-acetylation for 40 minutes produced derivatives that are most active in increasing SEAM 3 binding. This 40 minute de-N-acetylation procedure typically generates 25%-60% de-N-acetylated residues for polysialic acid containing materials (e.g., 35% for colominic acid (NmB PSA) and 56% for NmC PSA) as determined by resorcinol assay Example 9)).

Example 11

Figure 9:
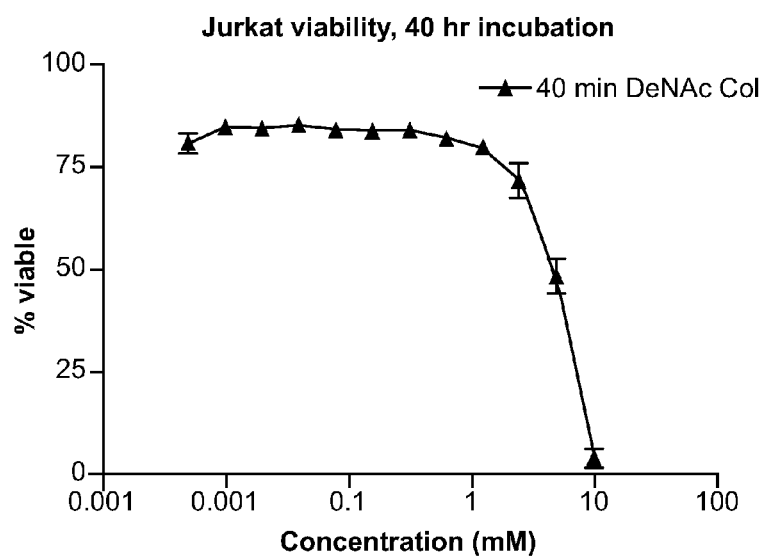
FIG. 9 shows the effect of the 40 min DeNAc col derivative concentration on the viability of Jurkat cells after 40 hours incubation.

Effect of Os Derivatives Produced by Time-Controlled De-N-Acetylation on the Viability of Jurkat T-Cell Leukemia Cells The effect of contacting the partially de-N-acetylated colominic acid derivatives (40 min deNAc col) prepared as described in Example 10 on the viability of human T-cell leukemia Jurkat cell lines in culture was measured using a cell viability assay. The 40 min deNAc col stock solution in water was first heated to 56° C. for 1 hour sterilize the solution. This is necessary since the 40 min deNAc col forms high molecular mass aggregates that do not pass through a 0.22μ filter and, thus, the stock solutions in water can not be sterilized by filtration. Jurkat cells ($2 \times 10^5$ cells/ml) were incubated with several dilutions of the derivatives as indicated in FIG. 9 for 40 hours in round-bottom 96-well plates (Falcon), 200 μl/well. Plates were then spun at 1,000×g for 5 minutes. The cells were resuspended in Guava ViaCount reagent and read on a Guava EasyCyte flow cytometer, using the Guava ViaCount assay (all from Guava Technologies).

As shown in FIG. 9, the 40 min deNAc col derivatives reduce the viability of Jurkat cells. The viability curve has an extreme concentration dependence, which is indicative of a highly cooperative process, for example, the cooperative assembly of high molecular weight complexes.

Similar results were obtained for OS derivatives made from *N. meningitidis* Serogroup C capsular polysaccharide homopolymer composed of N-acetyl neuraminic acid bearing C7-O-acetyl and C8-O-acetyl residues linked by an α(2→9) glycosidic bond.

Example 12

Production of OS Derivatives Enriched for Non-Reducing End De-N-Acetyl Sialic Acid Residues by Non-Oxidizing Acid Hydrolysis To produce smaller OS derivatives that are enriched for de-N-acetyl sialic acid at the non-reducing end, the 40 min alkaline de-N-acetylation (process described in Example 10) was followed by non-oxidizing acid hydrolysis in 0.1 M sodium acetate buffer, pH 5.5 for 18 hrs in a hydrolysis tube (Pierce) in which dissolved gasses had been evacuated by alternately freezing and thawing the solution under vacuum. Removal of dissolved gasses from the solution was found to be essential to minimize oxidative damage to the polysaccharide that can occur in the presence of strong acid or high concentrations (10%) of acetic acid. After cooling to ambient temperature, the pH was increased to 8-9 with 2M NaOH. The solution was dialyzed in water and lyophilized as described above. The resulting material is enriched for Neu residues at the non-reducing end and is substantially undamaged by oxidization Example 13

Figure 10:
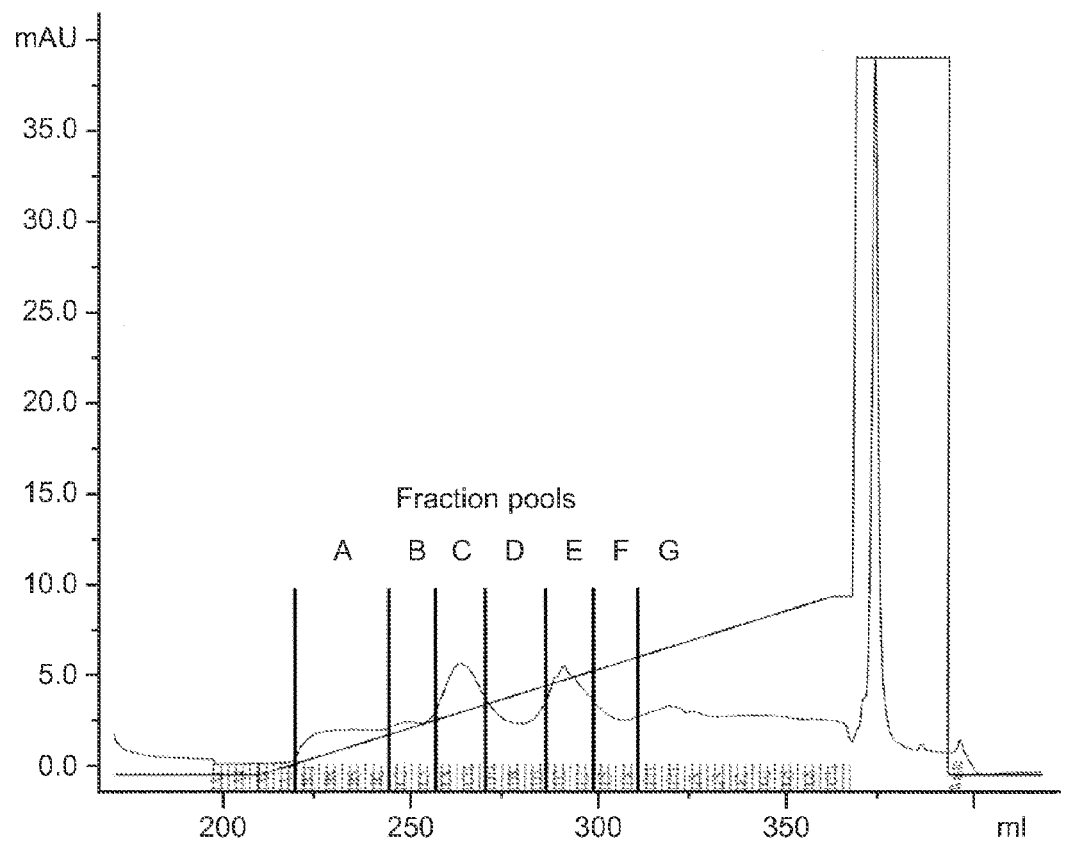
FIG. 10 shows the AEC chromatogram of acid hydrolyzed 40 min DeNAc col derivatives. The letters indicate fractions that were pooled.
Figure 11:
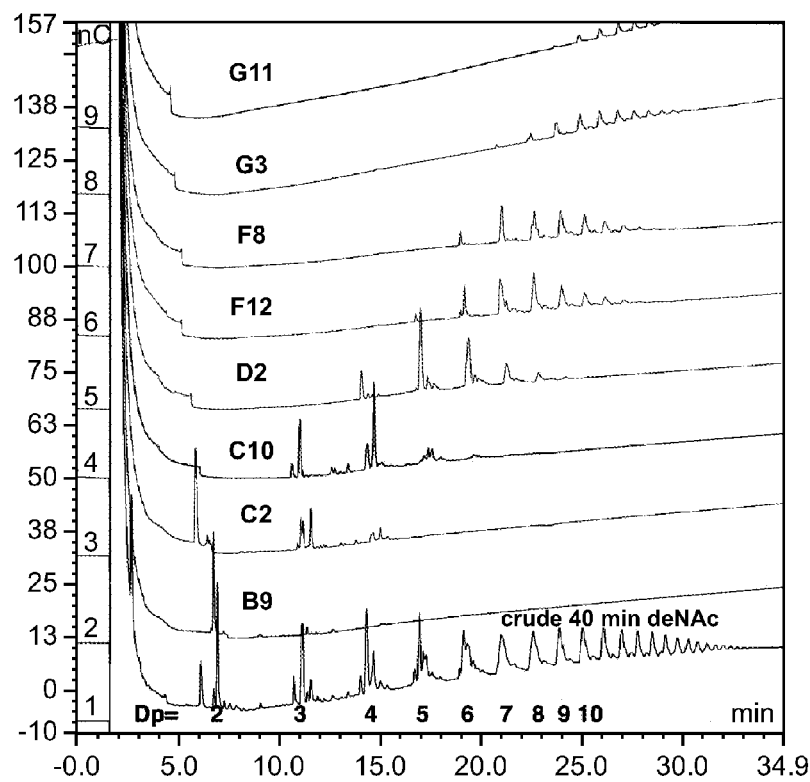
FIG. 11 shows HPAC-PAD chromatograms of selected individual fractions (microtiter plate well indicated above each chromatogram) from the AEC purification of acid hydrolyzed 40 min DeNAc col. The degree of polymerization (Dp) of oliogmers 2 through 10 are indicated below the chromatogram of the unpurified derivatives.
Figure 12:
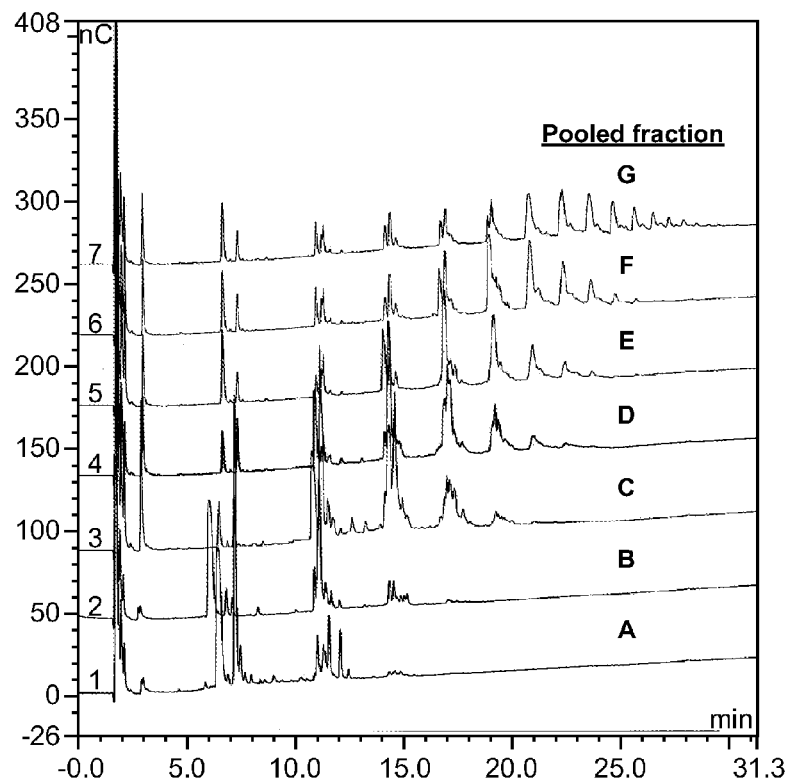
FIG. 12 shows the HPAC-PAD chromatograms of the fractions that were pooled as indicated in FIG. 10. After pooling, dialysis, and lyophilization, smaller oliogmers that were not present in the original fractions are present indicating that the longer oliomers hydrolyze to produce shorter oliogmers.

Purification of Defined OS Derivative that is Cytotoxic to Jurkat Leukemia Cells OS (prepared by 40 min alkaline de-N-acetylation followed by non-oxidizing acid hydrolysis in 0.1 M sodium acetate buffer, pH 5.5 for 18 hrs as described in Example 12) were separated by ion exchange chromatography (AEC) on an Äkta™ FPLC fitted with a 5 ml HiTrap Q FF™ anion exchange column (GE Healthcare Bio-Sciences Corp., Piscataway, N.J.). 20 mg of OS were diluted in 25 ml of 20 mM Bis-Tris buffer (Sigma-Aldrich), pH 7 and injected onto the column. OS were eluted (5 ml/minute) from the column with a 0M to 0.25M gradient of sodium chloride in 20 mM Bis-Tris buffer over a period of 30 min. Fractions (1 ml) were collected in a deep well microtiter plate (Thermo-Fisher) in alternating forward and backward rows. The gradient and elution profile are shown in FIG. 10. The ability of each fraction to inhibit binding of SEAM 3 to NPr PSA-dodecylamine (as prepared in Example 7) was determined by inhibition ELISA (as described in Example 8). Also, a portion of each fraction was analyzed by HPAC-PAD (as described in Example 10). FIG. 11 shows the HPAC-PAD chromatograms of several fractions from the AEC column. Chromatogram 1 is the unpurified 40 min deNAc col preparation. Notice in particular in chromatogram 2 how a nearly pure dimer is present in fraction B9 while another dimer (chromatogram 3 in FIG. 11) in later fraction C2 elutes from the PA20 column earlier than the dimer from fraction B9 shown in chromatogram 2. The dimer in chromatogram 3 is N-acetylated on both residues, thus it elutes with a higher concentration of salt from the AEC column. The example illustrates how AEC chromatography can be used to separate oligosaccharides containing different amounts of Neu residues and how the oligosaccharide derivatives can be identified by HPAC-PAD.

Fractions containing a narrow size range of oligomers were pooled, as indicted by the letters above delineated peaks in FIG. 10, dialyzed in water and lyophilized. Some of the individual fraction pools were then tested for their ability to decrease the viability of Jurkat cells as described in Example 11 and the amount of N-acetyl and de-N-acetyl sialic acid (Neu) was determined by resorcinol assay (Example 9). The data is summarized in Table 1.

TABLE 1

| Pooled fraction | Percent Neu | Percent decrease in Jurkat cell viability |
| --- | --- | --- |
| A | 36 | 25 |
| B | 17 | 15 |
| C | 19 | 9 |

TABLE 1-continued

| Pooled fraction | Percent Neu | Percent decrease in Jurkat cell viability |
|---|---|---|
| F | 14 | 28 |
| G | 32 | 8 |

The data presented in Table 1 shows that fractions containing the smallest Neu-containing OS (for example pool A dp=2-5) have as much cytotoxic activity as fractions containing the largest OS (pool F). All assays were done with 2.5 mg/ml (sometimes expressed as 10 mM based on a residue molecular mass of 250 g/ml)

The above results demonstrate that PSA and OS derivatives enriched for de-N-acetyl sialic acid at the non-reducing end were readily taken up by cancer cells, increased the number of cells positive for binding to SEAM 3, and increased the amount of antibody bound to the cells. The derivatives were also found capable of reducing viability of cancer cells expressing SEAM 3-reactive antigen upon exposure and internalization of antibodies directed against the antigen, and were cytotoxic to cancer cells at higher concentrations even in the absence of antibody. High molecular weight complexes/aggregates of the derivatives were found to be particularly active.

In addition, methods have been described for producing, purifying, and characterizing defined Neu-containing OS derivatives that can be used to increase expression of Neu-containing sialic acid antigens in cancer cells. Small, substantially unoxidized and purified OS derivatives having a degree of polymerization of about 2-5, particularly about 2-4, and a non-reducing end de-N-acetyl sialic acid residue were found to exhibit as much activity as longer OS derivatives (dp=5+), indicating the smallest OS derivatives bearing a non-reducing end de-N-acetyl sialic acid residue contain the minimal features necessary for effective activity.

It is evident from the above results and discussion that the PSA and OS derivatives may be used alone, as conjugates, or to increase the effectiveness of immunotherapy with SEAM 3, or other antibodies having similar antigenic specificities, as well as the uptake of antibodies that have been modified with cytotoxic drugs, toxins, or radionuclides, particularly as applied to increase a de-N-acetyl epitope of a cell, and specifically as applied to cancer therapy.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of increasing a de-N-acetylated antigen of a cancer cell, said method comprising:
    contacting a cancer cell having a de-N-acetyl sialic acid antigen with an effective amount of a composition comprising a polysialic acid derivative to increase the amount of the de-N-acetyl sialic acid antigen of said cell, wherein said polysialic acid derivative is substantially unoxidized and purified and comprises (i) a mixture of N-acetyl sialic acid and de-N-acetyl sialic acid residues, and (ii) a non-reducing end de-N-acetyl sialic acid residue that is resistant to degradation by exoneuraminidase.

2. The method of claim 1, wherein said cancer cell is a neuroblastoma cell, a leukemia cell, or a melanoma cell.

3. The method of claim 1, wherein said cell is in a subject, and said contacting comprises administering to said subject an effective amount of said composition.

4. The method of claim 3, wherein said administering is by infusion or by local injection.

5. The method of claim 3, wherein said administering is prior to surgical intervention to remove cancerous cells.

6. The method of claim 3, wherein said administering is at the time of or after surgical intervention to remove cancerous cells.

7. The method of claim 3, further comprising:
    administering at least one of an immunotherapy, a cancer chemotherapy or a radiation therapy to the subject.

8. A method of facilitating binding of an antibody to a cell having a de-N-acetyl sialic acid antigen, said method comprising:
    contacting a cell having a de-N-acetyl sialic acid antigen with an effective amount of a composition comprising a polysialic acid derivative so as to increase the amount of said antigen on said cell, wherein said polysialic acid derivative is substantially unoxidized and purified and comprises (i) a mixture of N-acetyl sialic acid and de-N-acetyl sialic acid residues, and (ii) a non-reducing end de-N-acetyl sialic acid residue that is resistant to degradation by exoneuraminidase; and
    contacting said cell with an antibody specific for said antigen to facilitate binding of said antibody to said cell.

9. The method of claim 8, wherein binding of said antibody to said cell is cytotoxic to the cell.

10. The method of claim 8, wherein said antibody comprises a conjugate.

11. The method of claim 10, wherein said conjugate comprises a detectable label or a cytotoxic drug.

12. The method of claim 8, wherein said cell is a cancer cell.

13. A method of reducing the viability of a cancer cell, said method comprising:
    contacting a cancer cell having a de-N-acetyl sialic acid antigen with an effective amount of a composition comprising a polysialic acid derivative so as to reduce the viability of said cell, wherein said polysialic acid derivative has a reducing end and a non-reducing end, and wherein said polysialic acid derivative is a substantially unoxidized and purified oligosaccharide comprising (i) a mixture of N-acetyl sialic acid and de-N-acetyl sialic acid residues, and (ii) a de-N-acetyl sialic acid residue at said non-reducing end that is resistant to degradation by exoneuraminidase.

14. The method of claim 13, wherein said cancer cell is a neuroblastoma cell, a leukemia cell, or a melanoma cell.

15. The method of claim 13, wherein said polysialic derivative comprises at least one dimer of de-N-acetyl sialic acid and N-acetyl sialic acid linked through a glycosidic bond selected from $\alpha(2\rightarrow 8)$ and $\alpha(2\rightarrow 9)$.

16. The method of claim 15, wherein said polysialic derivative has a degree of polymerization of about 2-10.

17. The method of claim 13, wherein said mixture comprises de-N-acetyl sialic residues in an amount of about 10%-60%.

18. The method of claim 13, wherein said polysialic acid derivative comprises a conjugate.

19. The method of claim 13, wherein said cell is in a subject, and said contacting comprises administering to said subject an effective amount of said composition.

* * * * *